United States Patent
Urbano et al.

(10) Patent No.: US 6,508,763 B1
(45) Date of Patent: Jan. 21, 2003

(54) MEDICAL DIAGNOSTIC ULTRASOUND SYSTEM AND METHOD

(75) Inventors: Joseph A. Urbano, Audubon, PA (US); Christopher B. Knell, Moorestown, NJ (US); Anthony P. Lannutti, Norristown, PA (US); Andrew J. Wood, Mt. Holly, NJ (US); Kevin S. Randall, Ambler, PA (US)

(73) Assignee: Ecton, Inc., Mountain View, CA (US)

(*) Notice: Subject to any disclaimer, the term of this patent is extended or adjusted under 35 U.S.C. 154(b) by 0 days.

(21) Appl. No.: 09/396,203

(22) Filed: Sep. 14, 1999

(51) Int. Cl.$^7$ ................................................. A61B 8/00
(52) U.S. Cl. ...................................................... 600/437
(58) Field of Search ....................... 600/437, 440–447, 600/459; 73/625, 626; 348/536, 571, 540; 606/1; 367/2, 7, 11

(56) References Cited

U.S. PATENT DOCUMENTS

| | | |
|---|---|---|
| 3,603,729 A | 9/1971 | Sperber |
| 4,335,427 A | 6/1982 | Hunt et al. |
| 4,337,481 A | 6/1982 | Mick et al. |
| 4,431,007 A | 2/1984 | Amazeen et al. |
| 4,444,196 A | 4/1984 | Stein |
| 4,585,008 A | 4/1986 | Jarkewicz |
| 4,729,379 A | 3/1988 | Ohe |
| 4,750,367 A | 6/1988 | Bernatets |
| 4,751,846 A | 6/1988 | Dousse |
| 4,785,818 A | 11/1988 | Hardin |
| 4,846,188 A | 7/1989 | Yoshioka |
| 4,878,115 A | 10/1989 | Elion |
| 4,887,306 A | 12/1989 | Hwang et al. |

(List continued on next page.)

FOREIGN PATENT DOCUMENTS

RU 984463 12/1982

OTHER PUBLICATIONS

"The Flexibility of Configurable Computing," Villasenor and Hutchings, IEEE Signal Processing Magazine, Sep. 1998, vol. 15, No. 5, pp. 67–84.
Declaration of Stuart Carp (1 page).
Declaration of John Williams (7 pages).
Pridham and Mucci, Digital Interpolation Beamforming for Low–Pass and Bandpass Signals Proceedings of the IEEE, vol. 67, No. 6, pp 904–919, Jun. 1979.
"System Five—Crisp. Clear. Incomparable Cardiac Images," <http://www.ge.com/medical/ultrasound/msusys5.html>, 2 pages, 1997–2000.
"System Five—A Better Way to Use Ultrasound Data," <http://www.ge.com/medical/ultrasound/msu5dat.html>, 2 pages, 1997–2000.
"Perception Ultrasound," <http://www.perceptionultrasound.com>, 2 pages, printed 2000.

Primary Examiner—Marvin M. Lateef
Assistant Examiner—Ali M. Imam

(57) ABSTRACT

The preferred embodiments described herein relate to a medical diagnostic ultrasound imaging system with at least one reprogrammable logic device, such as, for example, a field programmable gate array ("FPGA"). In one presently preferred embodiment, at least one reprogrammable logic device in the ultrasound system is reconfigured for probe changes (e.g., phased-array, curved array), for operator control changes (such as system mode changes, e.g., B-Mode, color Doppler), and/or dynamically as part of system operation (such as between ultrasonic pulse firings and/or between frames). By utilizing at least one reprogrammable logic device, the preferred embodiments reduce the size and cost of the ultrasound system without compromising the performance characteristics of the system. Further, unlike ultrasound systems that accommodate different sets of requirements by designing hardware modules to the most demanding requirements or by using separate hardware circuits for each alternative, the presently preferred embodiments provide a much less complex and costly solution.

54 Claims, 36 Drawing Sheets

U.S. PATENT DOCUMENTS

| | | |
|---|---|---|
| 4,888,694 A | 12/1989 | Chesarek |
| 5,000,182 A | 3/1991 | Hinks |
| 5,040,537 A | 8/1991 | Katakura |
| 5,060,515 A | 10/1991 | Kanda et al. |
| 5,099,847 A | 3/1992 | Powers et al. |
| 5,103,823 A | 4/1992 | Acharya et al. |
| 5,142,558 A | 8/1992 | Franciose |
| 5,152,290 A | 10/1992 | Freeland |
| 5,181,513 A | 1/1993 | Touboul et al. |
| 5,215,094 A | 6/1993 | Franklin et al. |
| 5,233,993 A | 8/1993 | Kawano |
| 5,235,985 A | 8/1993 | McMorrow et al. |
| 5,251,027 A | 10/1993 | Labeau |
| 5,255,683 A | 10/1993 | Monaghan |
| 5,325,858 A | 7/1994 | Moriizumi |
| 5,325,859 A | 7/1994 | Ishihara et al. |
| 5,345,426 A | 9/1994 | Lipschutz |
| 5,357,580 A | 10/1994 | Forestieri et al. |
| 5,388,079 A | 2/1995 | Kim et al. |
| 5,425,366 A | 6/1995 | Reinhardt et al. |
| 5,456,257 A | 10/1995 | Johnson et al. |
| 5,457,996 A | 10/1995 | Kondo et al. |
| 5,467,770 A | 11/1995 | Smith et al. |
| 5,469,851 A | 11/1995 | Lipschutz |
| 5,476,096 A | 12/1995 | Olstad et al. |
| 5,482,046 A | 1/1996 | Deitrich |
| 5,513,640 A | 5/1996 | Yamazaki et al. |
| 5,520,187 A * | 5/1996 | Snyder ...................... 600/447 |
| 5,530,681 A | 6/1996 | Bloom |
| 5,533,510 A | 7/1996 | Koch, III et al. |
| 5,544,128 A | 8/1996 | Kim et al. |
| 5,544,655 A | 8/1996 | Daigle |
| 5,555,534 A | 9/1996 | Maslak et al. |
| 5,564,428 A | 10/1996 | Soernmo et al. |
| 5,568,813 A | 10/1996 | Deitrich et al. |
| 5,570,691 A | 11/1996 | Wright et al. |
| 5,573,001 A | 11/1996 | Petrofsky et al. |
| 5,581,517 A | 12/1996 | Gee et al. |
| 5,595,179 A | 1/1997 | Wright et al. |
| 5,619,995 A | 4/1997 | Lobodzinski |
| 5,647,360 A | 7/1997 | Bani-Hashemi et al. |
| 5,653,236 A * | 8/1997 | Miller ...................... 600/447 |
| 5,666,955 A | 9/1997 | Kondo et al. |
| 5,722,412 A | 3/1998 | Pflugrath et al. |
| 5,735,797 A * | 4/1998 | Muzilla et al. ............. 600/441 |
| 5,758,649 A | 6/1998 | Iwashita et al. |
| 5,784,336 A | 7/1998 | Gopinathan et al. |
| 5,797,846 A | 8/1998 | Seyed-Bolorforosh et al. |
| 5,825,431 A * | 10/1998 | Walker ...................... 348/536 |
| 5,873,824 A | 2/1999 | Doi et al. |
| 5,893,363 A * | 4/1999 | Little et al. |
| 5,970,025 A | 10/1999 | Cole et al. |
| 5,971,928 A | 10/1999 | Dodd et al. |
| 5,993,390 A | 11/1999 | Savord et al. |
| 6,028,809 A * | 2/2000 | Schleicher et al. .... 365/230.03 |
| 6,115,626 A | 9/2000 | Whayne et al. |
| 6,120,449 A * | 9/2000 | Snyder ...................... 600/447 |
| 6,126,601 A * | 10/2000 | Gilling ...................... 600/440 |
| 6,126,608 A | 10/2000 | Kemme et al. |
| 6,231,510 B1 | 5/2001 | Negrin et al. |
| 6,241,675 B1 | 6/2001 | Smith et al. |
| 6,251,073 B1 | 6/2001 | Imran et al. |

\* cited by examiner

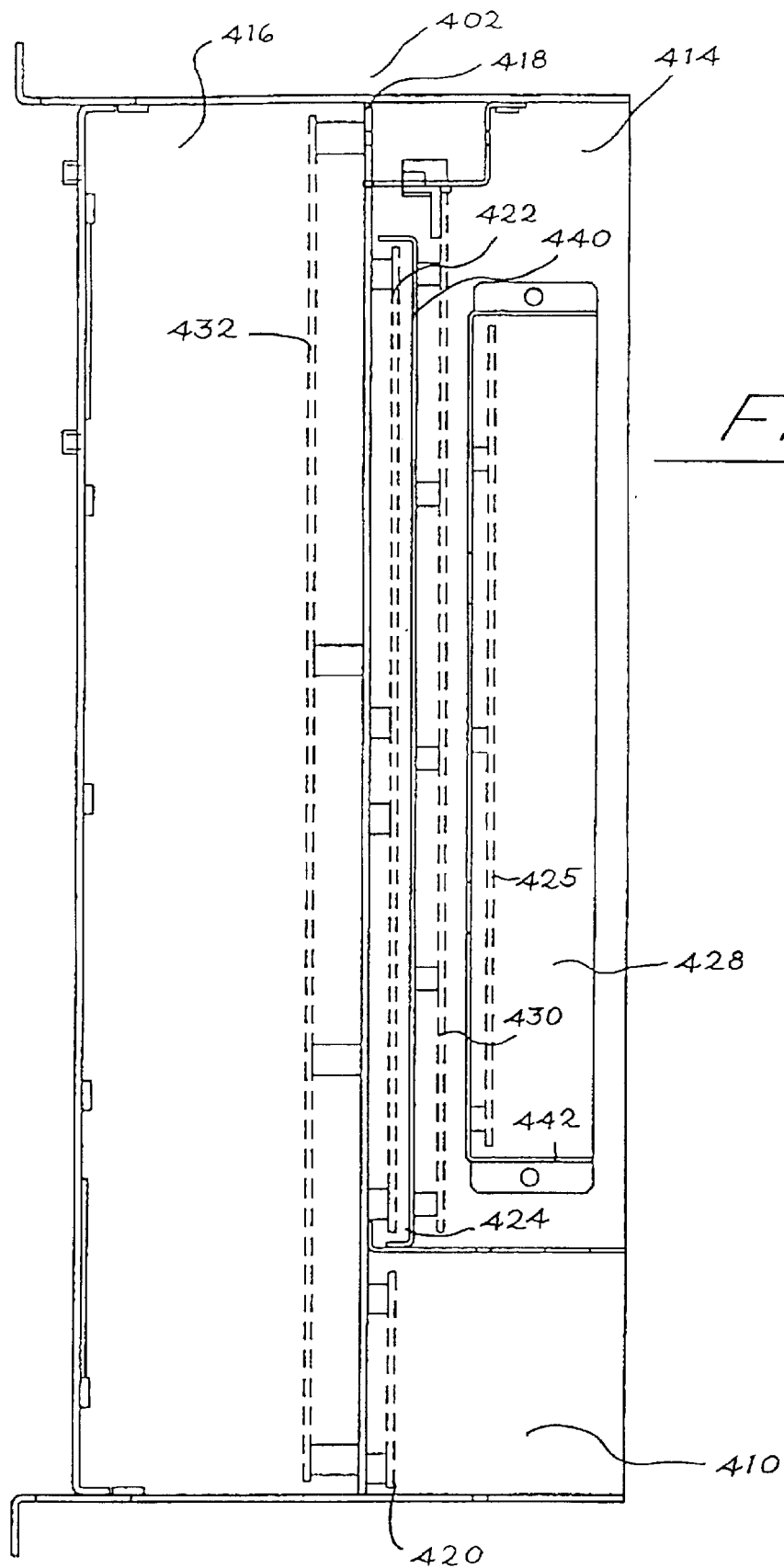

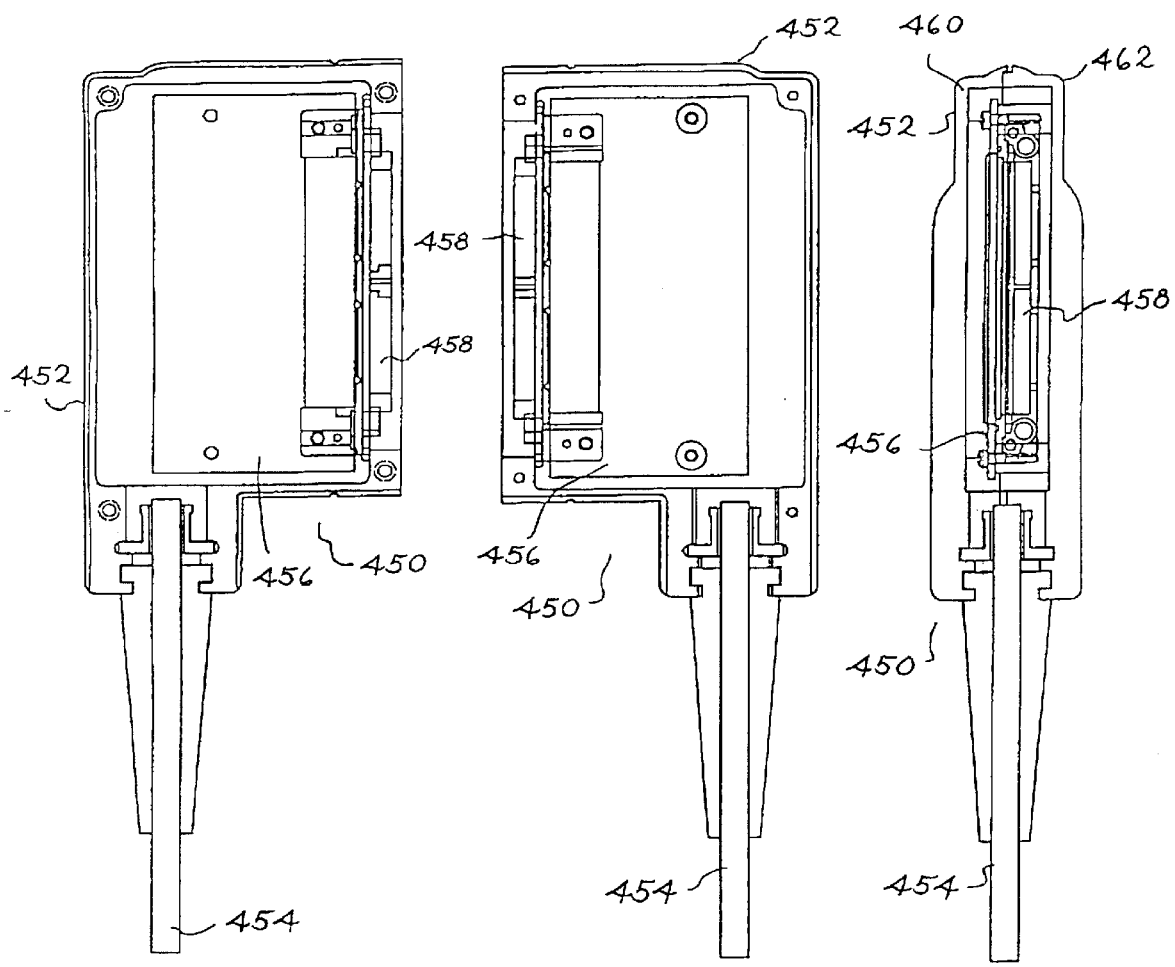
Fig. 4H   Fig. 4I
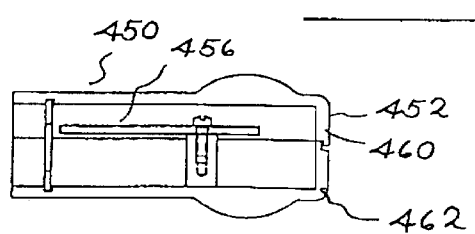
Fig. 4J
Fig. 4K

Fig. 4L

| PIN # | SIGNAL | PIN # | SIGNAL | PIN # | SIGNAL | PIN # | SIGNAL |
|---|---|---|---|---|---|---|---|
| 1 | CHAN 1 | 41 | BID_DATA | 81 | GROUND | 121 | TEMP_SENS |
| 2 | PRB_OUT 1 | 42 | GROUND | 82 | CHAN 2 | 122 | TEMP_RTN |
| 3 | CHAN 3 | 43 | BID_CLOCK | 83 | GROUND | 123 | TEMP_REF |
| 4 | GROUND | 44 | GROUND | 84 | CHAN 4 | 124 | GROUND |
| 5 | CHAN 5 | 45 | !PID_WR | 85 | GROUND | 125 | PRB_PWR |
| 6 | GROUND | 46 | future use | 86 | CHAN 6 | 126 | future use |
| 7 | CHAN 7 | 47 | future use | 87 | GROUND | 127 | future use |
| 8 | GROUND | 48 | GROUND | 88 | CHAN 8 | 128 | future use |
| 9 | CHAN 9 | 49 | CHAN 33 | 89 | GROUND | 129 | GROUND |
| 10 | GROUND | 50 | GROUND | 90 | CHAN 10 | 130 | CHAN 34 |
| 11 | CHAN 11 | 51 | CHAN 35 | 91 | GROUND | 131 | GROUND |
| 12 | GROUND | 52 | GROUND | 92 | CHAN 12 | 132 | CHAN 36 |
| 13 | CHAN 13 | 53 | CHAN 37 | 93 | GROUND | 133 | GROUND |
| 14 | GROUND | 54 | GROUND | 94 | CHAN 14 | 134 | CHAN 38 |
| 15 | CHAN 15 | 55 | CHAN 39 | 95 | GROUND | 135 | GROUND |
| 16 | GROUND | 56 | GROUND | 96 | CHAN 16 | 136 | CHAN 40 |
| 17 | CHAN 17 | 57 | CHAN 41 | 97 | GROUND | 137 | GROUND |
| 18 | GROUND | 58 | GROUND | 98 | CHAN 18 | 138 | CHAN 42 |
| 19 | CHAN 19 | 59 | CHAN 43 | 99 | GROUND | 139 | GROUND |
| 20 | GROUND | 60 | GROUND | 100 | CHAN 20 | 140 | CHAN 44 |
| 21 | CHAN 21 | 61 | CHAN 45 | 101 | GROUND | 141 | GROUND |
| 22 | GROUND | 62 | GROUND | 102 | CHAN 22 | 142 | CHAN 46 |
| 23 | CHAN 23 | 63 | CHAN 47 | 103 | GROUND | 143 | GROUND |
| 24 | GROUND | 64 | GROUND | 104 | CHAN 24 | 144 | CHAN 48 |
| 25 | CHAN 25 | 65 | CHAN 49 | 105 | GROUND | 145 | GROUND |
| 26 | GROUND | 66 | GROUND | 106 | CHAN 26 | 146 | CHAN 50 |
| 27 | CHAN 27 | 67 | CHAN 51 | 107 | GROUND | 147 | GROUND |
| 28 | GROUND | 68 | GROUND | 108 | CHAN 28 | 148 | CHAN 52 |
| 29 | CHAN 29 | 69 | CHAN 53 | 109 | GROUND | 149 | GROUND |
| 30 | GROUND | 70 | GROUND | 110 | CHAN 30 | 150 | CHAN 54 |
| 31 | CHAN 31 | 71 | CHAN 55 | 111 | GROUND | 151 | GROUND |
| 32 | GROUND | 72 | GROUND | 112 | CHAN 32 | 152 | CHAN 56 |
| 33 | future use | 73 | CHAN 57 | 113 | GROUND | 153 | GROUND |
| 34 | future use | 74 | GROUND | 114 | future use | 154 | CHAN 58 |
| 35 | future use | 75 | CHAN 59 | 115 | future use | 155 | GROUND |
| 36 | future use | 76 | GROUND | 116 | GROUND | 156 | CHAN 60 |
| 37 | future use | 77 | CHAN 61 | 117 | UNUSED | 157 | GROUND |
| 38 | P_MUX_DAT | 78 | GROUND | 118 | SW_HV- | 158 | CHAN 62 |
| 39 | P_MUX_CK | 79 | CHAN 63 | 119 | UNUSED | 159 | PRB_OUT 2 |
| 40 | P_MUX_ST | 80 | GROUND | 120 | SW_HV+ | 160 | CHAN 64 |

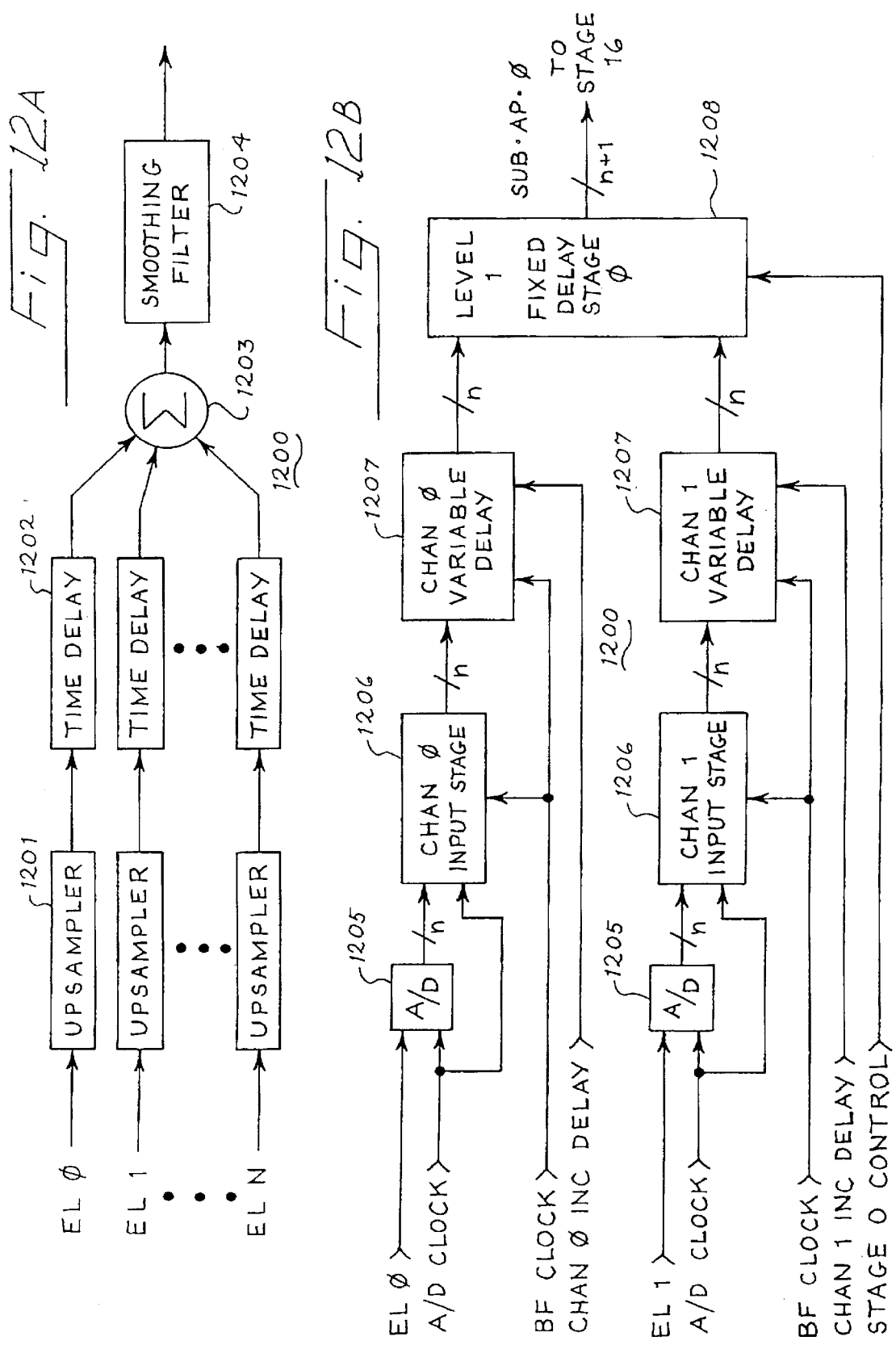

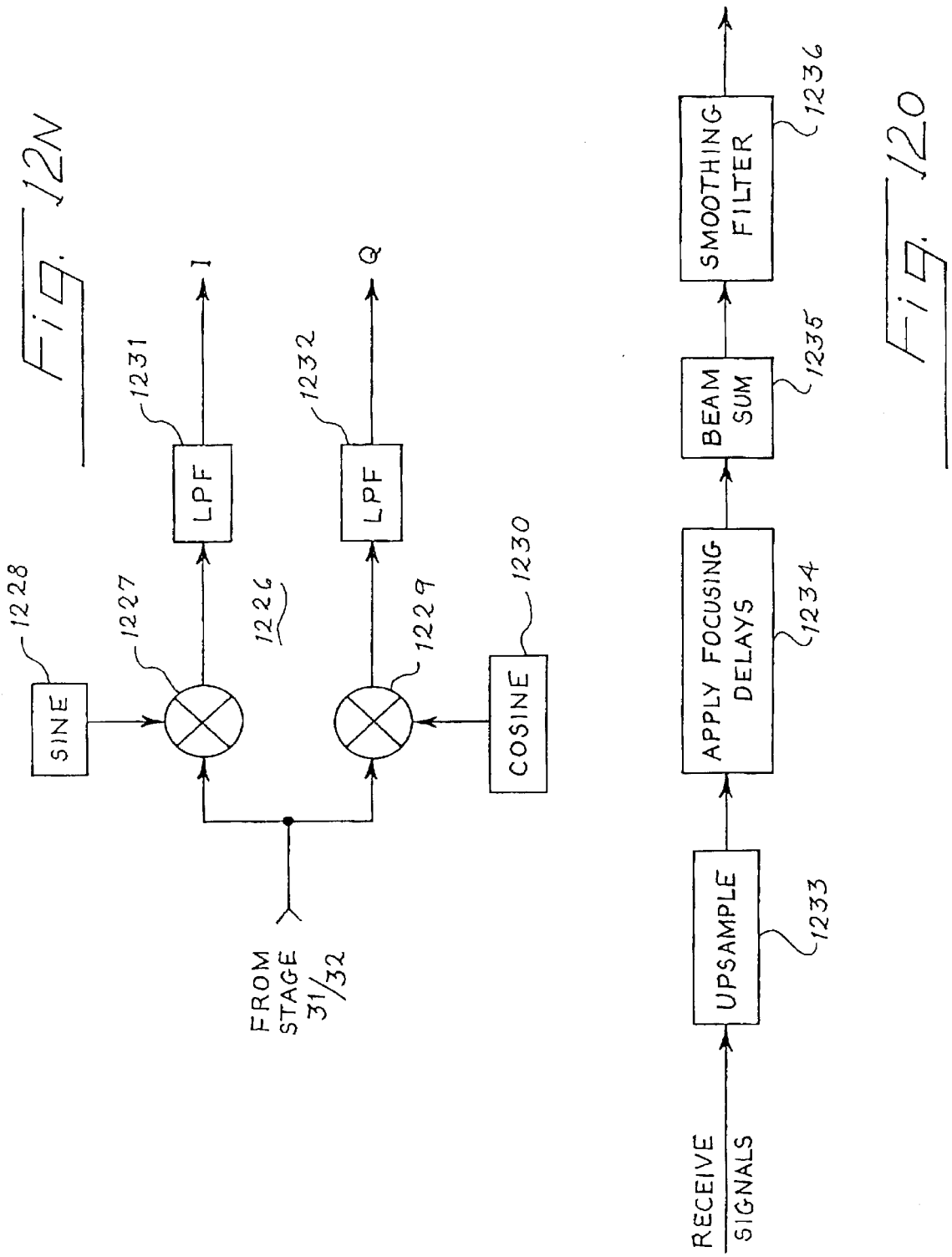

| LEVEL | MAX DELAY LENGTH (CLOCK CYCLES) | NO BITS IN | NO BITS OUT | NO STAGES |
|---|---|---|---|---|
| 1 | 3 | 8 | 9 | 32 |
| 2 | 6 | 9 | 10 | 16 |
| 3 | 12 | 10 | 11 | 8 |
| 4 | 24 | 11 | 12 | 4 |
| 5 | 48 | 12 | 13 | 2 |
| 6 | 96 | 13 | 14 | 1 |

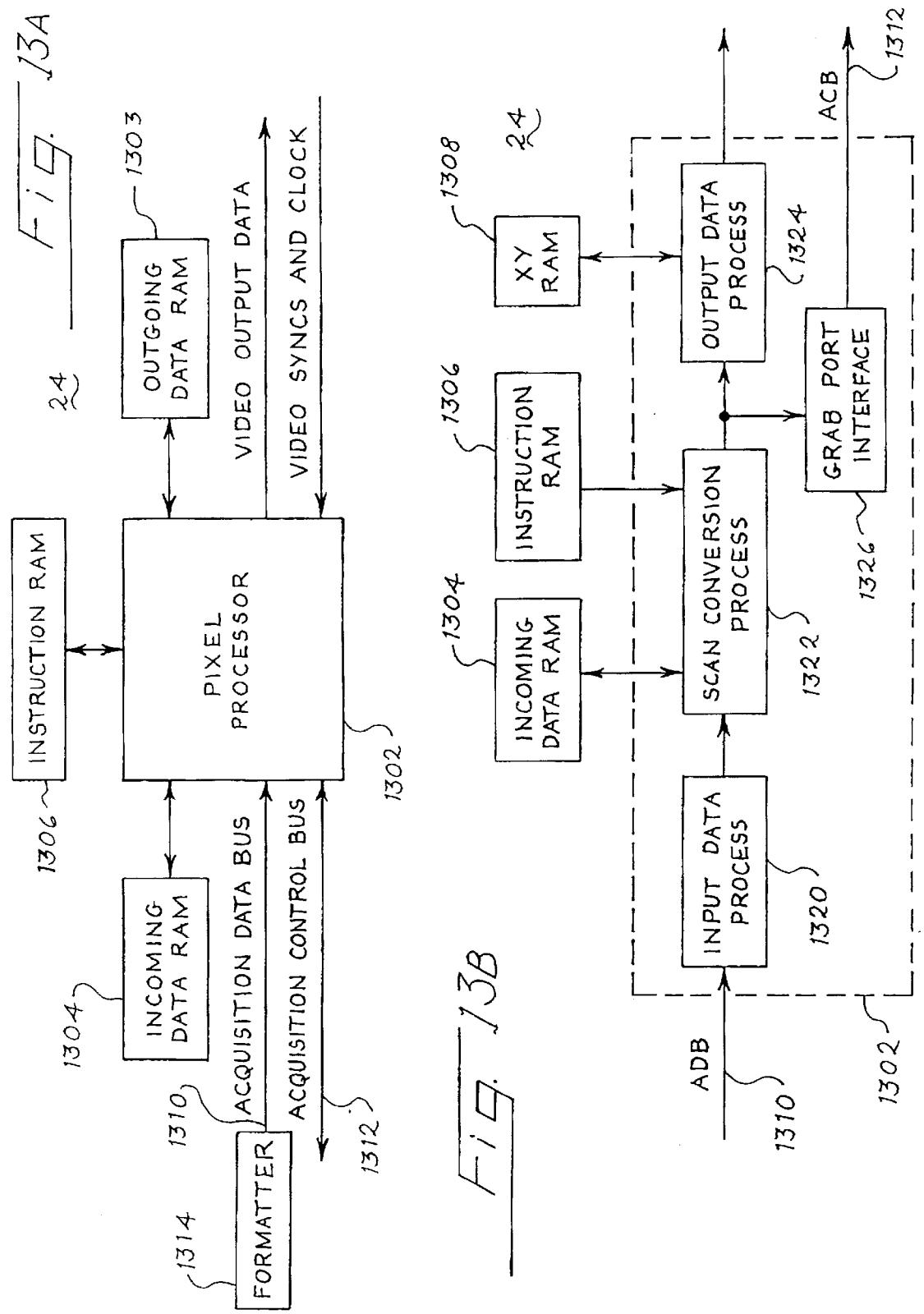

MEDICAL DIAGNOSTIC ULTRASOUND SYSTEM AND METHOD

MICROFICHE/COPYRIGHT REFERENCE

This application includes a microfiche appendix of 47 sheets of microfiche having 2,772 frames. A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND

This invention relates to a medical diagnostic ultrasound system and method. Ultrasound systems generate a sequence of images representing a region of a body. Different processes and hardware are used to generate the images. Many of the processes and hardware components are divided into ultrasound subsystems. Each subsystem is typically implemented with an ASIC. The ASIC is designed to perform a particular process. The processes are determined in part as a function of the system architecture or ASIC based design.

The subsystems are connected to a back plane or common structure to form the ultrasound system. The ultrasound system typically is mounted on a large wheeled cart.

BRIEF SUMMARY

The present invention is defined by the following claims, and nothing in this section shall be a limitation on those claims.

By way of introduction, the following preferred embodiments include a medical diagnostic ultrasound imaging system with at least one reprogrammable logic device, such as, for example, a field programmable gate array ("FPGA"). In one presently preferred embodiment, at least one reprogrammable logic device in the ultrasound system is reconfigured for probe changes (e.g., phased-array, curved array), for operator control changes (such as system mode changes, e.g., B-Mode, color Doppler), and/or dynamically as part of system operation (such as between ultrasonic pulse firings and/or between frames). By utilizing at least one reprogrammable logic device, the preferred embodiments reduce the size and cost of the ultrasound system without compromising the performance characteristics of the system. Further, unlike ultrasound systems that accommodate different sets of requirements by designing hardware modules to the most demanding requirements or by using separate hardware circuits for each alternative, the presently preferred embodiments provide a much less complex and costly solution.

The preferred embodiments will now be described in conjunction with the following drawings.

BRIEF DESCRIPTION OF THE DRAWINGS

FIG. 4C is a schematic top view of one preferred embodiment depicting the circuit boards and shielding.

FIG. 4H depicts a left side view of one preferred embodiment transducer connector.

FIG. 4I depicts a right side view transducer connector of FIG. 4H.

FIG. 4J depicts a connector end view of the transducer connector of FIG. 4H.

FIG. 4K depicts a top view of the transducer connector of FIG. 4H.

FIG. 4L shows a table of input/output connections for the transducer connector of FIG. 4H.

FIG. 12A is a high-level block diagram of a medical diagnostic ultrasonic receive beamformer included in the system 10.

FIG. 12B is a more detailed block diagram including some of the upsamplers and a portion of some of the time delay blocks of FIG. 12A.

FIG. 12N is a more detailed block diagram of the smoothing filter of FIG. 12A.

FIG. 12O is a flow chart of a method performed by the receive beamformer of FIG. 12A.

FIG. 13A is a block diagram of one preferred embodiment of a scan converter.

FIG. 13B is a block diagram representing the structure and related process of one preferred embodiment of the scan converter of FIG. 13A.

DETAILED DESCRIPTION OF THE PREFERRED EMBODIMENTS

The diagnostic ultrasound system and method described herein provide for many efficiencies for both processing techniques and mechanical costs and size. The discussion below begins with a general system description. Various components and processes related to those and other components are then further described. Any one of various features described herein may be used alone or in combination with other features.

GENERAL SYSTEM DESCRIPTION

Figure 1:
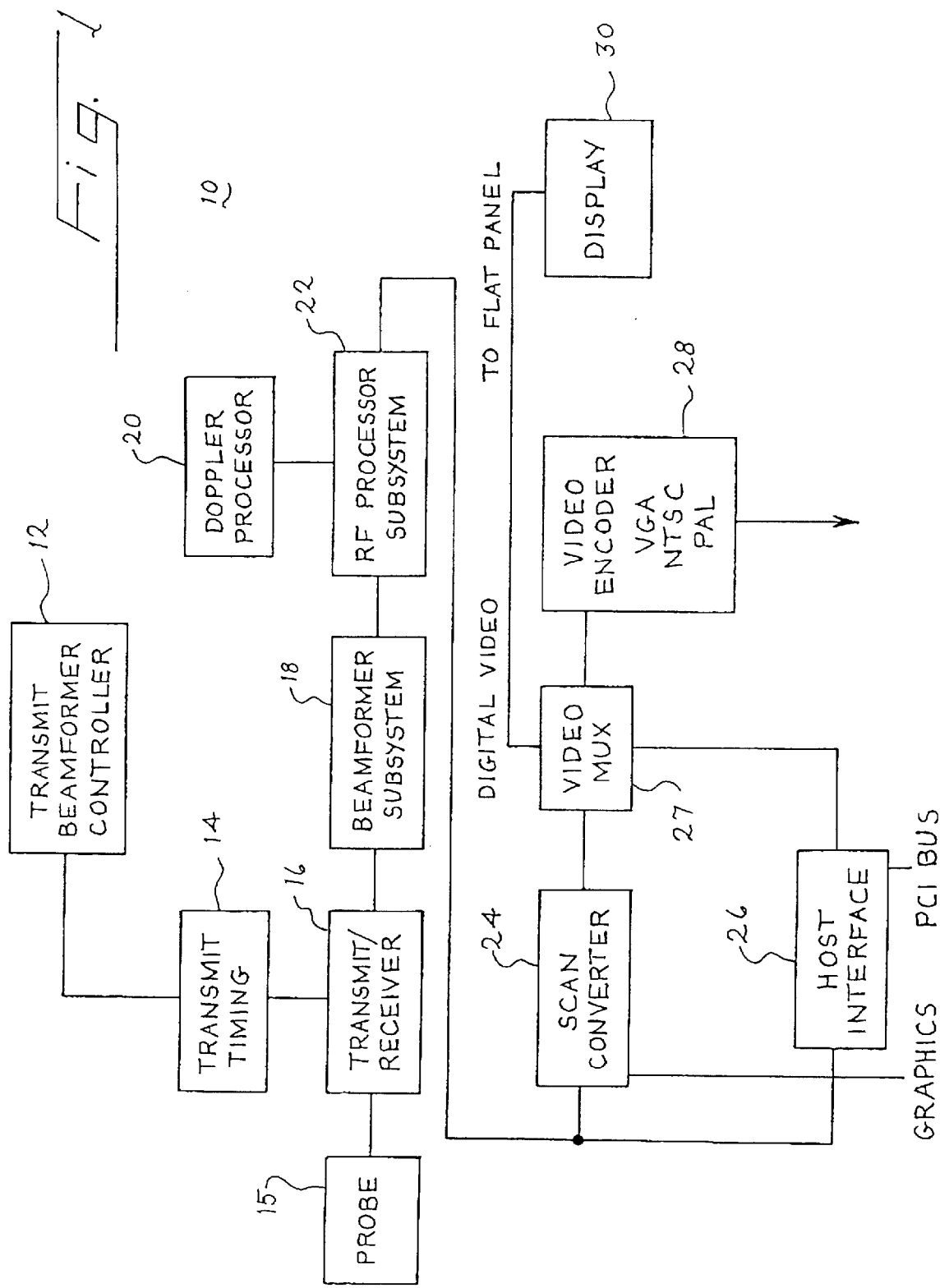
FIG. 1 is a block diagram of one preferred embodiment of a medical diagnostic ultrasound system for image generation.

FIG. 1 shows a medical diagnostic ultrasound system 10. The system includes an transmit beamformer controller 12, a transmit timer 14, a probe 15, a transmitter/receiver 16, a beamformer 18, a Doppler processor 20, an RF processor 22, a scan converter 24, a video encoder 28, a display 30 and a host interface 26 connected as shown. Different, fewer or additional components and/or connections may be provided. Preferably, the system 10 comprises a Sonnet™ ultrasound system from Ecton, Inc. Other systems, such as manufactured by Acuson or other system manufacturers may be used.

The transmit beamformer controller 12 comprises a processor, ASIC, digital signal processor, dedicated hardware, programmable logic device and/or other devices for controlling the transmission of acoustic energy along one or more scan lines. Preferably, the transmit beamformer controller 12 comprises one 10K50V field programmable gate array device and also includes an ECG signal processor function. The transmit beamformer controller 12 coordinates the timing and order of various transmit pulse types. The relative timing and characteristics of waveforms used to generate the beam of acoustic energy is set by the transmit beamformer controller 12. A sequence of such transmissions is controlled in order to scan a region of interest (i.e. scan along a plurality of scan lines). The transmit waveforms vary as a function of the imaging mode (e.g. 2D imaging mode, color flow mode or spectral Doppler mode). The transmit beamformer controller 12 also controls labeling data received in response to the transmissions as discussed below. The label includes information about their pulse type, scan line, frame number, frame period, and a pulse and line sequencing tag.

The transmit timer 14 comprises a processor, ASIC, digital signal processor, dedicated hardware, programmable logic device and/or other devices for generating the transmit waveforms. Preferably, the transmit timer 14 comprises two Altera Flex10K30A field programmable gate arrays. Timing signals to implement the timing selection from the transmit beamformer controller 12 are provided as start of waveform signals to the transmitter/receiver 14. The transmit timer 14 generates digital signals to control the timing of transmit pulses for each element of the transducer array 15. The relative timing of these signals is generally different for each scan line. Transmit beam focussing is also provided by varying the delays across all elements of the transducer array 15.

The transmitter/receiver 14 comprises digital and analog devices for generating the waveforms and pre-processing echo signals. Preferably, the transmitter/receiver 14 comprises discrete analog circuitry, including amplifiers, filters, digital to analog converters and analog to digital converters. The transmit waveforms are provided to the transducer array 15.

The transducer array 15 comprises a phased linear, a linear, a curved linear, a sector, a wide view, a single element, a 1.5 dimensional, a two-dimensional or other array of transducer elements. The transducer array 15 converts the transmit waveforms into acoustic energy. Reflections responsive to the transmissions are received and converted to electrical signals. The electrical signals are amplified, filtered and digitized by the transmitter/receiver 16. The signals are then beamformed.

The beamformer 18 comprises a processor, a digital signal processor, an ASIC, dedicated hardware and/or a programmable logic device. Preferably, the beamformer 18 comprises Altera 10K100A programmable logic devices. The beamformer 18 applies delays and sums the signals from the transducer elements to generate data representing the structure along the scan line. The output of the beamformer 18 is provided to the RF processor 22.

The RF processor 22 comprises a processor, a digital signal processor, an ASIC, dedicated hardware and/or a programmable logic device for detecting the received data amplitude, envelope and/or power. Preferably, the RF processor 22 mixes the received RF signal down to baseband in-phase and quadrature components. The in-phase and quadrature components are then passed through an envelope detector to extract the signal echo intensity (i.e. B-mode and/or M-mode data). The in-phase and quadrature components are also provided to the Doppler processor 20 to extract Doppler frequency shift information for color flow mode and PW and CW spectral Doppler modes.

The Doppler processor 20 comprises a processor, a digital signal processor, an ASIC, dedicated hardware and/or a programmable logic device for estimating Doppler parameters. For example, velocity, variance and power are estimated using auto-correlation, cross-correlation or other processes for estimating motion.

In one preferred embodiment, the RF processor 20 and the Doppler processor 22 comprise two 10K50V field programmable logic devices and one 10K100A field programmable logic array (FPGA) device along with a supporting digital signal processor integrated circuit (e.g. Analog Devices 21061). In one embodiment, one FPGA and a part of another mix, low pass filter and decimate the received signals to generate in-phase and quadrature data. The other part of the other FPGA envelope detects to generate B-mode and M-mode data. The third FPGA performs decimation, clutter filtering and auto-correlation. The subsequent digital signal processor estimates velocity, variance and energy as well as per frame spatial filtering, temporal filtering and noise/flash rejection for the Doppler data.

The intensity data and the Doppler estimates are low-pass filtered and sample rate decimated. The decimation is performed so that the data rate corresponds to the geometry of the display 30 after scan conversion.

The scan converter 24 comprises a processor, a digital signal processor, an ASIC, dedicated hardware and/or a programmable logic device for converting the received data from an acoustic grid or other acquisition format to a Cartesian coordinate format (i.e. raster) for the display 30. Preferably, the scan converter 24 comprises a 10K50V field programmable logic device and three supporting memory devices (2 SRAMs and 1 DRAM) for data buffering and instruction storage. Using interpolation and/or extrapolation, the data is reformatted.

The reformatted data is provided to a video multiplexer 27. The video multiplexer 27 merges the central processor generated graphics video with the image information from the scan converter 24. The combined information is provided to the display 30 for display of an image and annotation information.

The combined information is also provided to the video encoder 28. The video encoder 28 comprises a processor, a digital signal processor, an ASIC, dedicated hardware and/or a programmable logic device for formatting data in one or more standard formats, such as a DICOM format or for a VCR, CRT or other device. Preferably, the video encoder 28 comprises an off-the-shelf integrated circuit device (e.g. Chrontel CH7003).

The display 30 comprises a monitor, CRT, LCD and/or flat panel display device for generating an image of the scanned region. Preferably, the display 30 comprises 640× 480 liquid crystal display with an eighteen-bit digital RGB data interface. The display format defaults to standard 640×480 VGA at a 60 Hz frame rate, non-interlaced. The frame rate and video timing may be different and/or vary.

The data from the Doppler processor 20 and/or RF processor 22 is also provided to the host interface 26. The host interface 26 comprises a processor, a digital signal processor, an ASIC, dedicated hardware and/or a programmable logic device for controlling the components of the system 10 and interfacing between external data processing and/or storage devices. Preferably, the host interface device comprises one 10K50V field programmable gate array with a PLX 9080 PCI bus interface integrated circuit as supporting logic. Data going to or output from the scan converter 24 is passed through the host interface 26 to a central processor unit (CPU) and/or a memory device for temporary or permanent image storage. The host interface 62 interfaces between the scan converter 24 and a PCI bus interfacing to the central processing unit 52. The central processing unit 52 causes the data to be stored within the central processing unit 52, in the system RAM 58 and/or the disk drive 54. Other storage locations may be used. The data may then be used for any of various processes, such as performing calculations and/or re-generating images for review.

Figure 5:
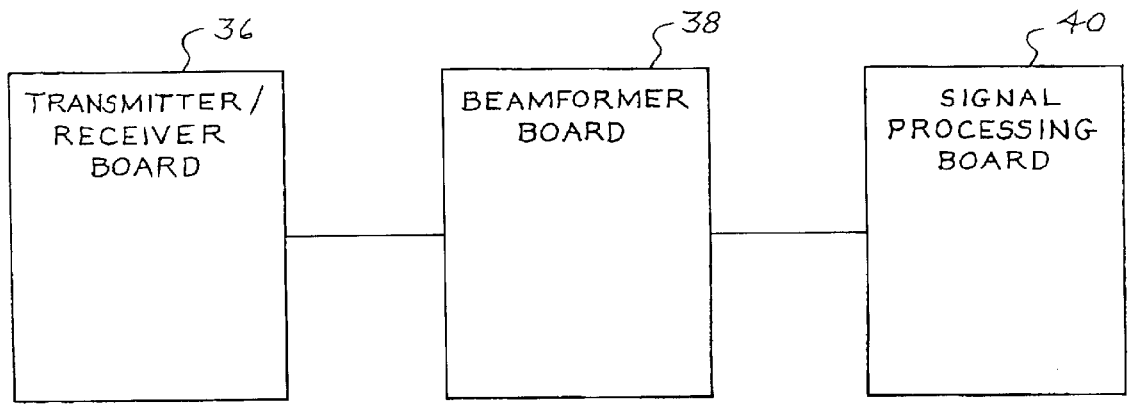
FIG. 5 is a block diagram of one preferred embodiment of the board layout of the system of FIG. 1.

In one preferred embodiment using field programmable gate arrays, the components of the system 10 are distributed over three boards as shown in FIG. 5. This configuration accommodates package-size considerations and reduces the number of input/output signals. The transmitter/receiver 16 is located on a transmitter/receiver board 36. The beamformer 18 and transmit timer 14 are located on a beamformer board 38. The remaining signal processing components of the system 10, including the transmit beamformer controller 12, are located on or connect with a signal processing board 40. In alternative embodiments, more or fewer boards are provided. Furthermore, a different division of the components between the boards may be used.

In one preferred embodiment, the front end transmitter/receiver board 36 is shielded from the beamformer field programmable gate arrays and the signal processing board 40. When the field programmable gate arrays are distributed among two or more boards, it is preferred that each board contain an EPROM identifying which field programmable gate arrays are located on the board as well as a board serial number, part number and other identifying information.

Figure 3:
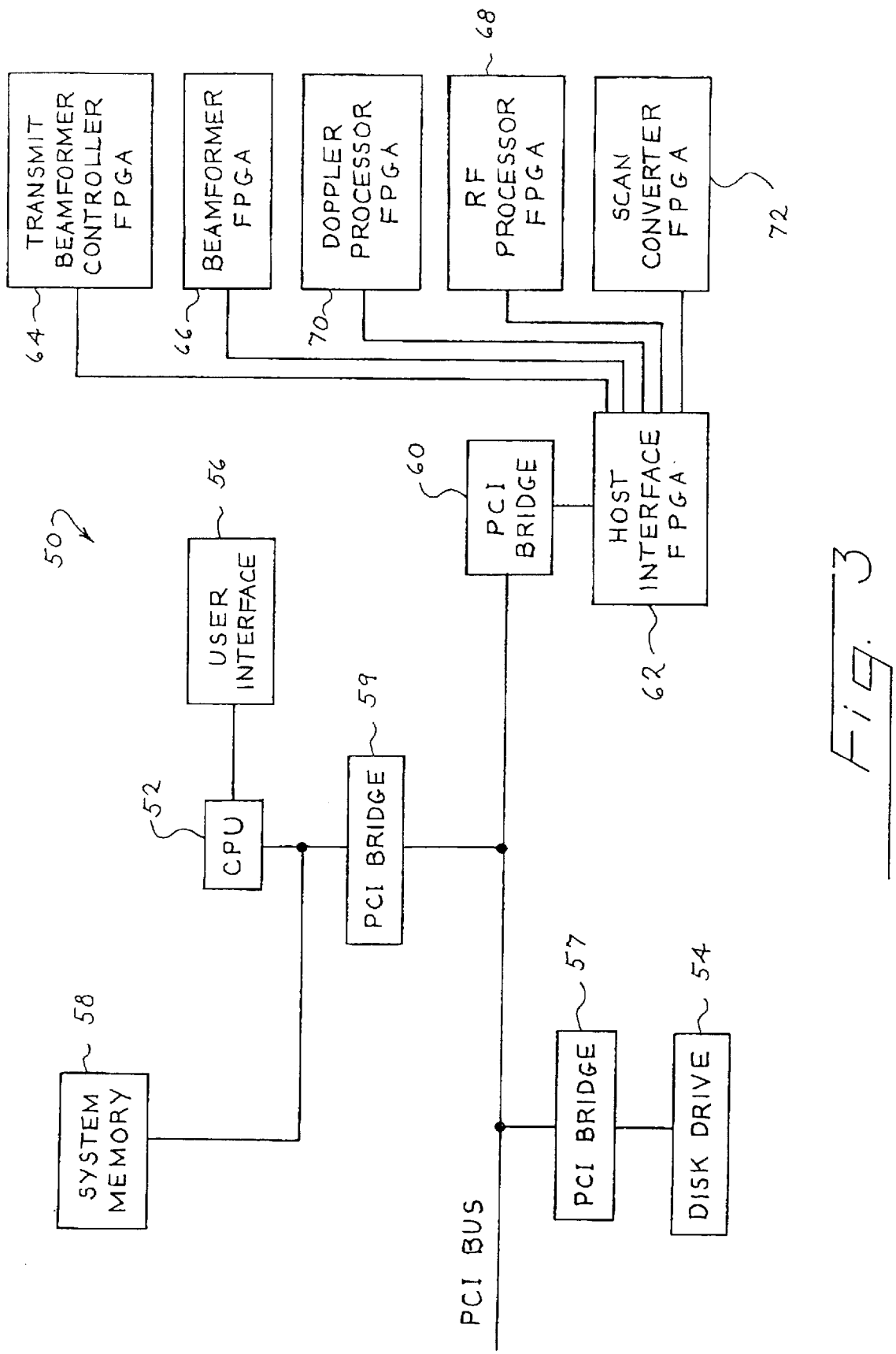
FIG. 3 is a block diagram of one preferred embodiment of the control structure of the system of FIG. 1.
Figure 4A:
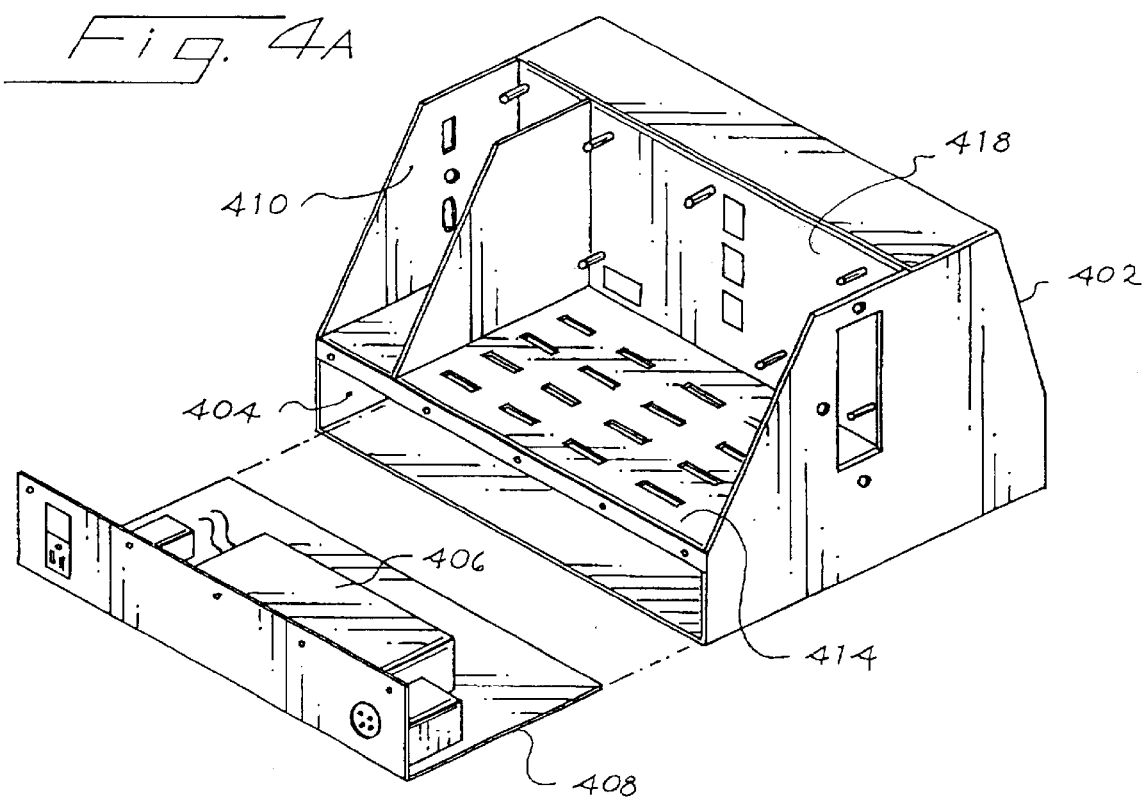
FIG. 4A shows a perspective rear view of one preferred embodiment depicting electromagnetic interference shielding.
Figure 4B:
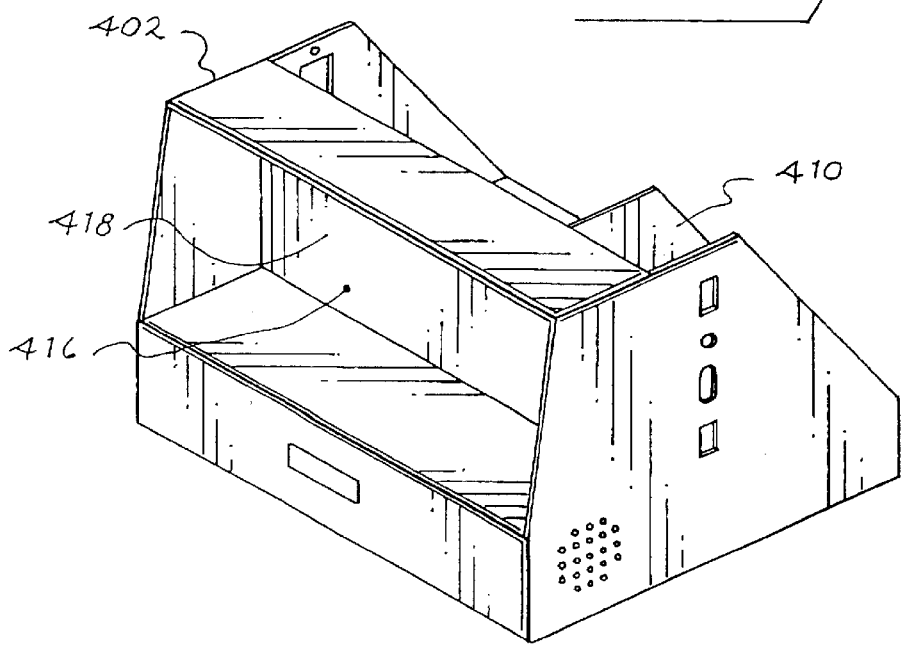
FIG. 4B shows a perspective front view of the shielding of FIG. 4A.
Figure 4D:
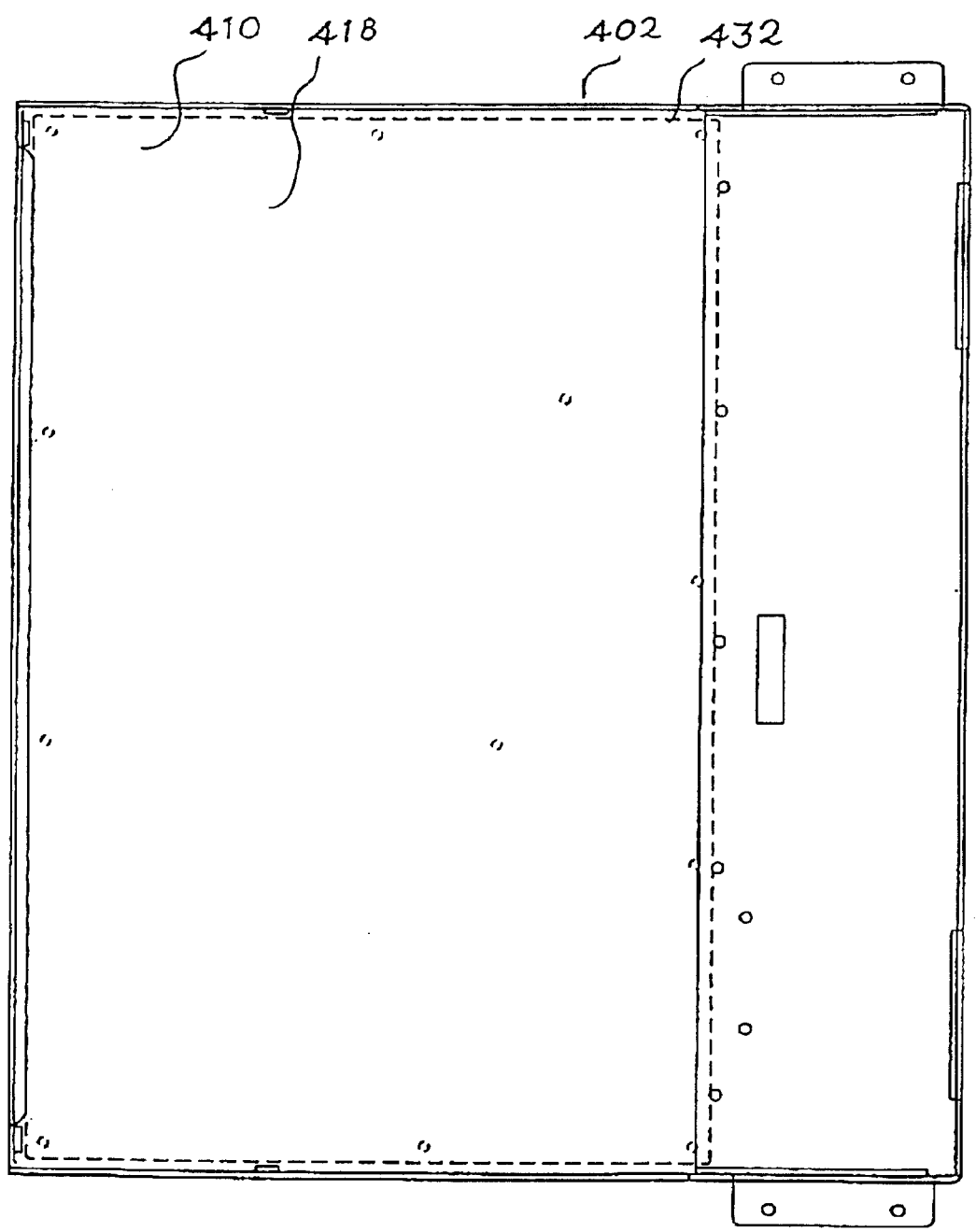
FIG. 4D is a schematic front view depicting the circuit boards and shielding of FIG. 4C.
Figure 4E:
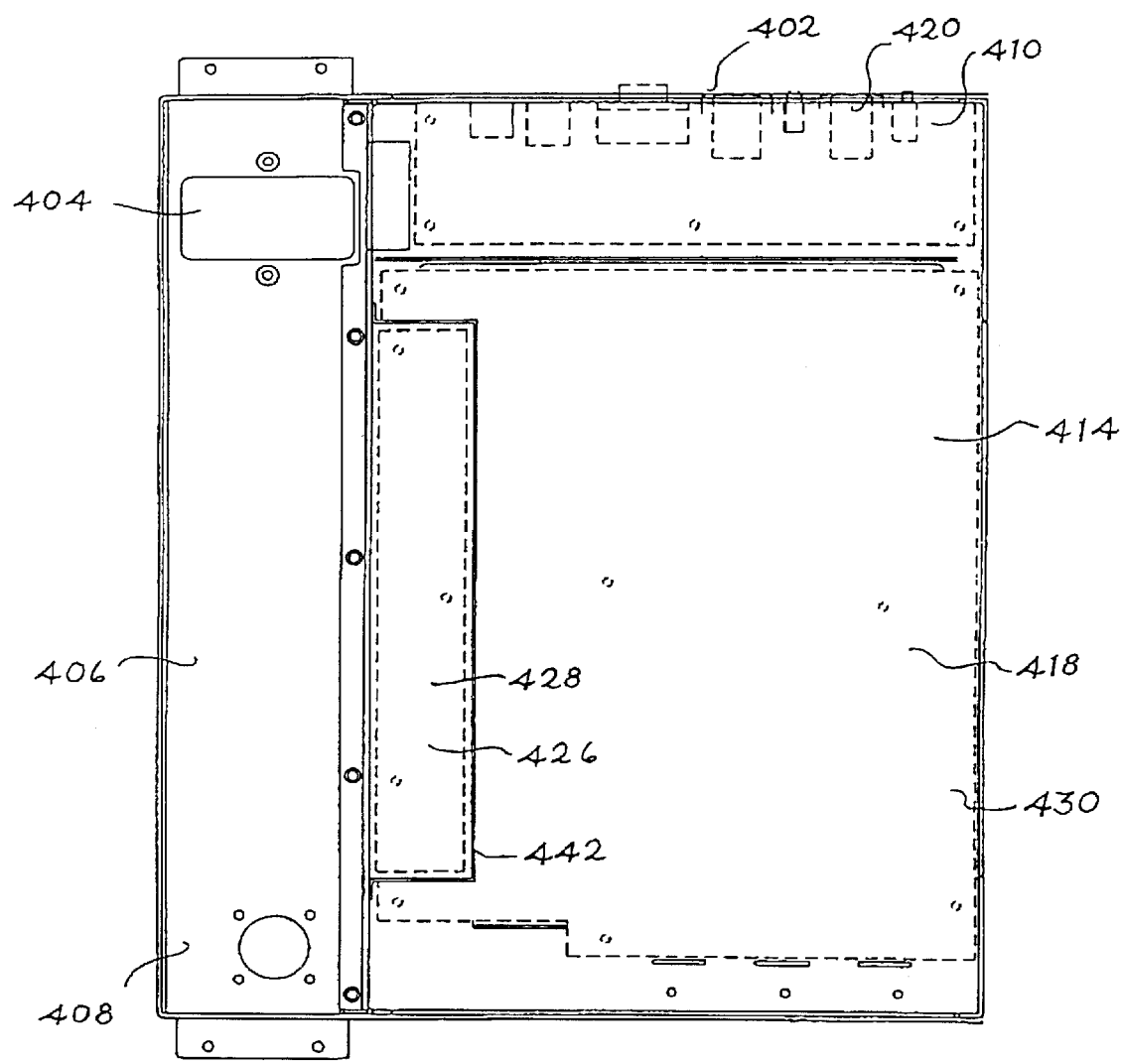
FIG. 4E is a schematic back view depicting the circuit boards and shielding of FIG. 4C.
Figure 4F:
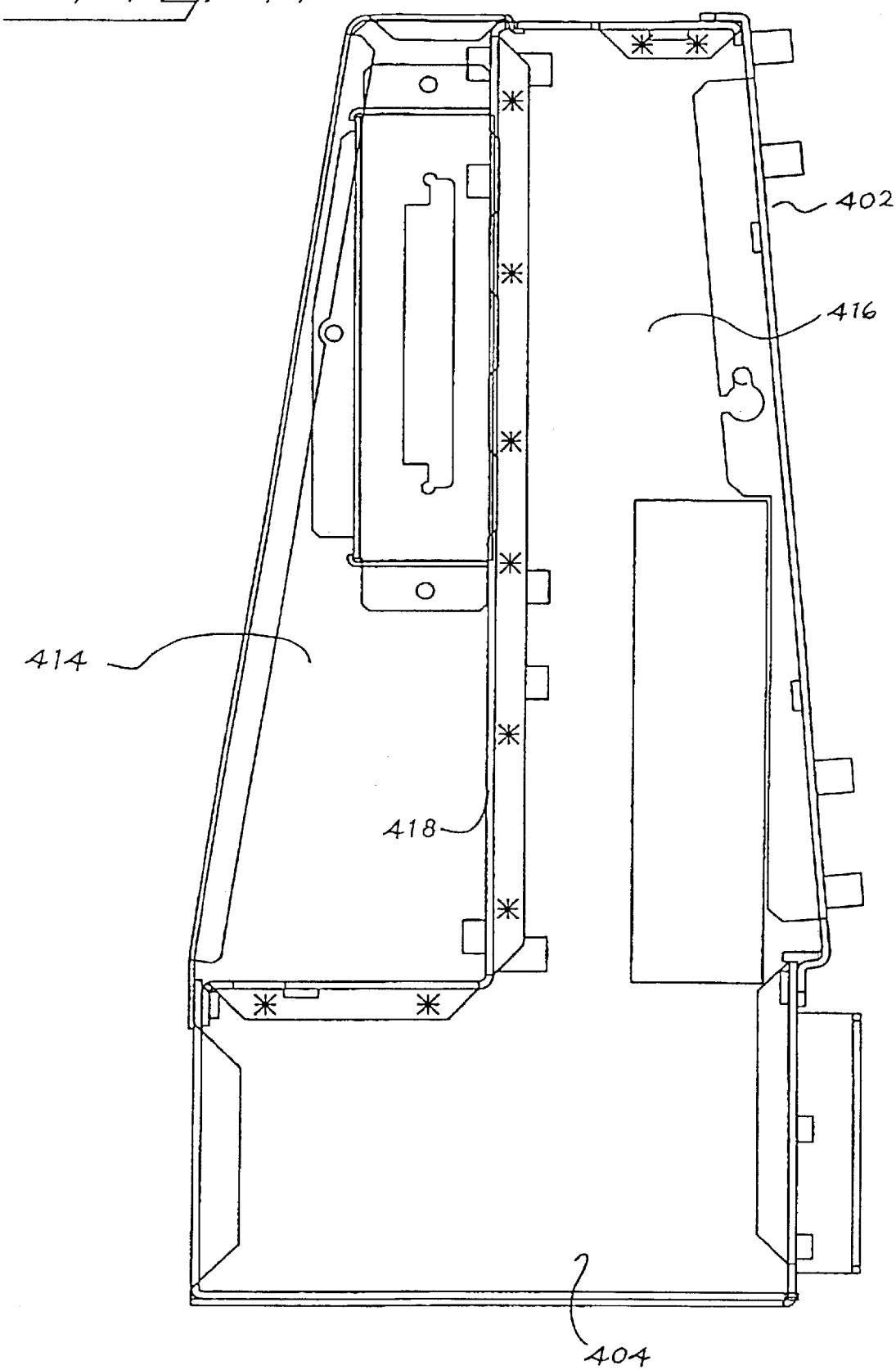
FIG. 4F is a schematic left side view depicting the circuit boards and shielding of FIG. 4C.
Figure 4G:
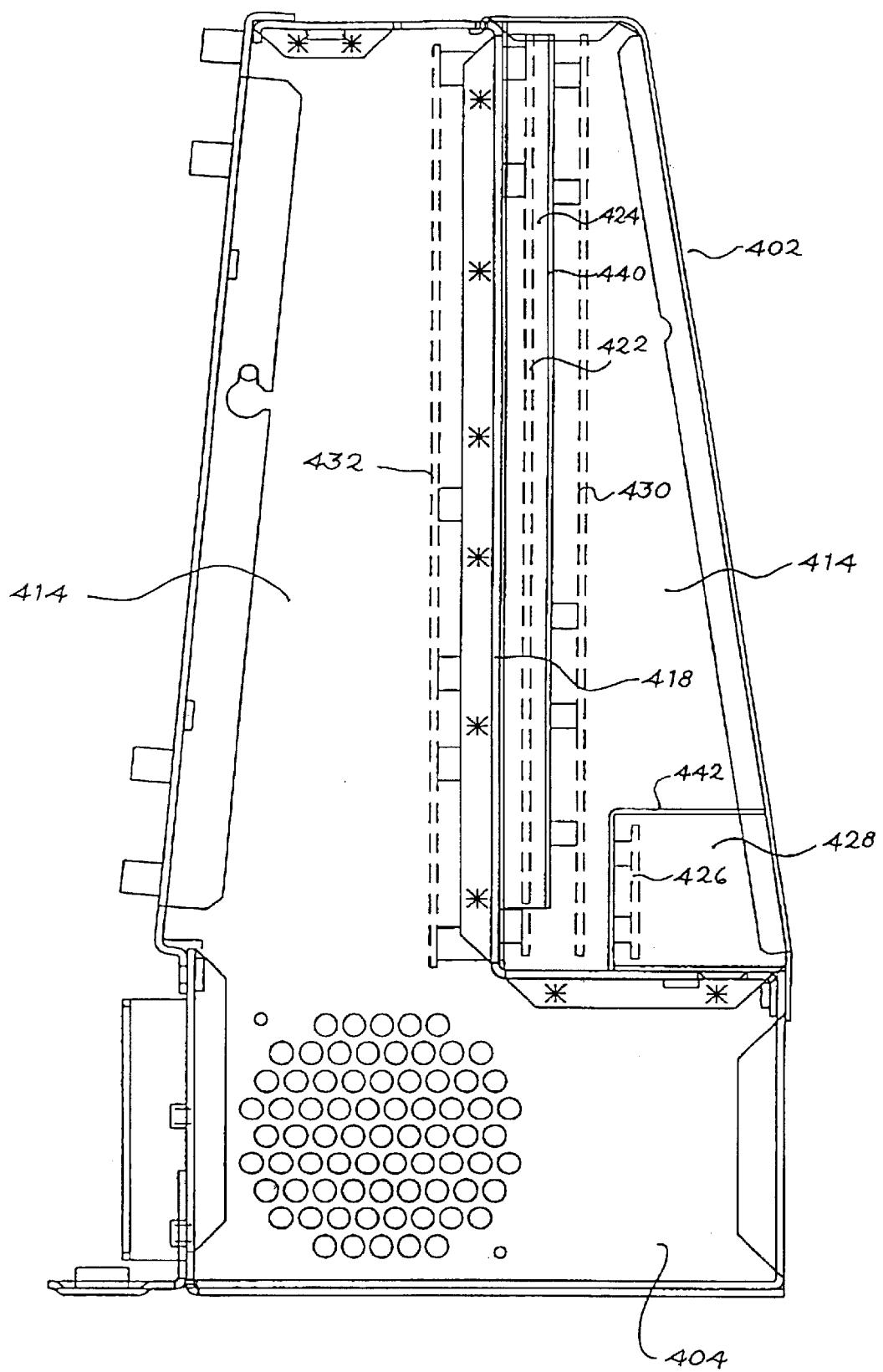
FIG. 4G is a schematic right side view depicting the circuit boards and shielding of FIG. 4C.

FIG. 3 is a block diagram of one preferred embodiment of a control system 50 of the medical diagnostic ultrasound imaging system 10 or another system. The system 50 comprises a central processing unit ("CPU") 52 coupled with a disk drive 54 via PCI bridges 59, 57, a user interface 56, and system memory 58. The CPU 52 is also coupled with a PCI bridge 60 via a PCI bus. The system memory 58 and the PCI bridge 60 are both coupled with a host interface field programmable gate array 62. The host interface field programmable gate array 62 is coupled with a transmit beamformer controller field programmable gate array 64, a beamformer field programmable gate array 66, an RF processor field programmable gate array 68, a Doppler processor field programmable gate array 70, and a scan converter field programmable gate array 72. The transmit beamformer controller field programmable gate array 64 is coupled through the transmit timer 14 with the transducer 15 (FIG. 1), such as a phased-array or single element transducer, and the scan converter field programmable gate array 72 is coupled with the display 30 (FIG. 1), such as a flat panel display device. The beamformer, RF processor, Doppler Processor and scan converter field programmable gate arrays 66, 68, 70 and 72 comprise an ultrasound data processing path for generating ultrasound images.

It is preferred that the disk drive 54 be a Fujitsu 2 Gigabyte, 2.5 inch hard drive and that the system memory 58 be a 64 megabyte SRAM. It is further preferred that the CPU 52 be a Cyrix Media GX chipset and that the field programmable gate arrays be from the Altera Flex 10k family. The field programmable gate arrays are preferably configured via a serial port with a three-line interface for clock, data, and configuration signals.

In one presently preferred embodiment, the transmit beamformer controller field programmable gate array 64 is implemented as a single field programmable gate array from the Altera Flex 10k50 family, the beamformer field programmable gate array 66 is implemented as a four-chip set from the Altera Flex 10k100 family, the RF processor field programmable gate array 68 is implemented as a two-chip set from the Altera Flex 10k50 family, the Doppler processor field programmable gate array 70 is implemented as a single field programmable gate array from the Altera Flex 10k100 family, and the scan converter field programmable gate array 72 is implemented as a single field programmable gate array from the Altera Flex 10k50 family. It is also preferred that the beamformer field programmable gate array 66 be associated with an SRAM, that the RF processor field programmable gate array 68 be associated with a DRAM, that the Doppler processor field programmable gate array 70 be associated with an SRAM, and that the scan converter field programmable gate array 72 be associated with 2 SRAMs and 1 DRAM. In alternative embodiments, one or more of the components comprise a processor, a digital signal processor, an ASIC, and/or dedicated hardware devices.

Preferably, the field programmable gate arrays are distributed on more than one board as described above where each board preferably contains an EPROM to identify the field programmable gate arrays located on that board. This information is used by the CPU 52 when configuring the host interface field programmable gate array 62 to send configuration data. Further, it is preferred that the field programmable gate arrays be synchronized to either a 21.5 MHz or a 43 MHz clock, and that the timing be specified and verified when compiled via development tools. It is further preferred that data transfer between field programmable gate arrays be through a synchronous data bus with a "data valid" tag signal using skew-controlled clocks and that the signals be double-registered to resynchronize when transferring between asynchronous clocks.

When the ultrasound system 50 is powered up (i.e. turned on), all of the field programmable gate arrays in the system expect to be programmed. To prevent each of the field programmable gate arrays from being programmed with configuration data intended for a single field programmable gate array, it is preferred that invalid configuration data be sent to the field programmable gate arrays upon power up. In this way, each of the field programmable gate arrays will be placed in an error state and only the intended field programmable gate array will be programmed with valid configuration data. The field programmable gate array is removed from the error state by reprogramming (i.e. re-configuring).

In one embodiment for implementing this power-up procedure, the host interface field programmable gate array 62 comprises an field programmable gate array from the Altera Flex 10k50 family and support dual, bi-directional 32-bit DMA via a PCI bus, with image and control data transferred on separate DMA channels. It is further preferred that the host interface field programmable gate array 62 have a 33 MHz DMA burst rate and have a double-buffer control for image data. Additionally, it is preferred that the PCI bridge controller 60 be a PLX 9080 DMA controller or PCI bus interface integrated circuit. When the system is powered up, it is preferred that the PCI bridge 60 program, under control of the CPU 52, the host interface field programmable gate array 62 via a dedicated serial port and be configured by toggling the clock and data signals.

In operation, when different functionality is required from one of the field programmable gate array components, the CPU 52 retrieves configuration data from the disk drive 54 and transfers the data to the system memory 58. The CPU 52 then commands a DMA controller in the PCI bridge 60 to retrieve the configuration data from a location in the system memory 58 and to send the configuration data through the host interface 62 to reprogram one of the field programmable gate arrays with the configuration data. It is preferred that a header be added to the configuration data in the system memory 58 to inform the host interface field programmable gate array 62 of the identity, location, and configuration signal of the field programmable gate array that is to be reprogrammed. If more than one field programmable gate array is to be reprogrammed, the above-described method can be repeated. Alternatively, several field programmable gate arrays can be reprogrammed in parallel when the configuration data is packed in a bit-slice format.

With any one of the versatile embodiments discussed above, different components and/or processes may be used. As described below, various features are provided.

EMBODIMENTS INCLUDING A SUBSYSTEM COMPRISING A PROGRAMMABLE LOGIC DEVICE

The subsystems using reprogrammable logic devices discussed below may be used with any one or more of the various embodiments discussed herein. The system 10 shown in FIG. 1 comprises several subsystems, such as the transmit beamformer controller 12 and/or transmit timer 14 (e.g. transmit beamformer including a controller), the beamformer 18 (e.g. receive beamformer), the Doppler processor 20 (e.g. color flow and/or spectral Doppler), the RF processor 22 (e.g. B-mode and/or M-mode processor), and the scan converter 24. These subsystems are within the ultrasound data processing path for processing ultrasound data.

In one embodiment, one or more of the subsystems in the ultrasound data processing path comprise, at least in part, one or more reprogrammable logic device. As used herein, a reprogrammable logic device comprises a plurality of logic elements the gate interconnections of which can be modified by an external data set loaded under software control by a processor residing in the system. Such reprogrammable logic devices include field programmable gate arrays (FPGA), flash PROM FPGA, static random access memory FPGA (SRAM FPGA), anti-fuse programmable logic devices, complex-programmable logic devices (C-PLD), electrically erasable PLD devices and other reprogrammable PLD devices. Preferably, the number of reprogramming operations is not limited by the device and/or the reprogrammable logic device includes components that may be partially or fully re-configured.

At least a portion of the essential functionality of the subsystem is performed by the reprogrammable logic device. As used herein, the essential functionality comprises the function to be performed by the subsystem, such as generating a transmit waveform for a transmit beamformer subsystem or scan converting data from an acoustic grid to a display format for a scan converter. In one embodiment, the essential functionality largely (i.e. at least 40% of the processing or signal path) resides in one or more reprogrammable logic devices. In alternative embodiments, the essential functionality mostly (i.e. at least 50%), substantially (i.e. at least 90%), and/or about entirely (i.e. at least 98%) resides in reprogrammable logic devices. The amount of processing performed by a component is determined as a function of the number of alterations of the data (e.g. delays and value changes) from data input to the component to data output from the component or the number of operations per unit time performed. The amount of a signal path comprised by a component is determined as a function of the number of components, the number of chips, the number of gates and/or flip flops and memory bits, and/or the amount of processing performed by components in the signal path.

In one embodiment, the beamformer 18 comprises a programmable logic device. The programmable logic device filters, interpolates, demodulates, phases, applies appodization, delays and/or sums the received signals, essential functions of the receive beamformer. In another embodiment, the transmit beamformer controller 12 and transmit timer 14 (e.g. transmit beamformer) comprises a programmable logic device. The programmable logic device digitally controls the delays and characteristic of transmit waveforms, and generates transmit waveforms from memory, essential functions of the transmit waveform. The programmable logic device may also implement relative delays between the waveforms as well as filter, interpolate, modulate, phase and apply apodization. Other components then perform digital to analog conversion and amplification. In these embodiments, the transducer array 15 comprises a multi-element linear, curved linear, phased linear, sector or wide view array. The programmable logic devices of the transmit and receive beamformer functions perform essential functions to process the plurality of signals associated with such multi-element electrically scanned arrays. For example, the array provides for more than 16, more than 32, or more than 64 channels.

In yet another embodiment, the scan converter 24 comprises a programmable logic device. The programmable logic device interpolates data from one format to another and/or generates memory address, essential functions, and may optionally include memory for the interpolation. In other embodiments, the RF processor 22 and/or the Doppler processor 20 comprise programmable logic devices. The programmable logic devices (1) perform the essential functions of detecting the envelope, amplitude or power of the signal and/or log compressing the signal and/or (2) perform essential functions of clutter filtering and/or the autocorrelation or other process to provide data for estimation of velocity, variance and/or energy, respectively.

Preferably, at least two subsystems along the ultrasound data path comprise programmable logic devices. The programmable logic devices are preferably operable to perform most of the digital processing within the ultrasound data path.

Using reprogrammable logic devices to perform essential functionality in a subsystem allows for efficient implementation of the functions. The method of performing the function is easily and quickly reprogrammed using the same hardware. Future upgrades and bug fixes are easily performed with reprogrammable logic devices. This efficiency provides for a lower cost, high-performance ultrasound imaging system. Fixed logic ASICs require a sizable up front investment in money and engineering time, and most modifications to an ASIC require additional investment in both money and time. Off-the-shelf processors can be very flexible in supporting future system upgrades and ease of programming. However, due to the limited instruction set given the fixed logic structure and the need to perform most rudimentary operations serially (i.e. one after the other), processors are slow in performance compared to hardware designed specifically for the task at hand. The following paragraphs describe exemplary applications.

PROGRAMMING RE-PROGRAMMABLE LOGIC DEVICE EMBODIMENTS

Operator Control Changes

In one preferred embodiment, at least one of the reprogrammable logic devices in the ultrasound system is reprogrammed in response to operator control changes. Operator control changes include, but are not limited to, changes in system mode, gain, filter settings, and zoom. For ease of illustrations, changes in system mode will be used to illustrate these preferred embodiments. In different ultrasound modes, tradeoffs can be made with different functions. For example, while in color mode, lower structure image quality can be tolerated. Accordingly, the scan converter can apply extra resources to scan convert structures in B-mode, while using a lesser-quality scan conversion process in color mode, since lower image quality can be tolerated. Further, in color mode, multi-line acquisition can be substituted for higher image quality or composite image processing. Also, as described herein, changes can also be made in the beamformer, such as when the mode changes from B-mode to B/F mode.

Additionally, because the color Doppler image is of primary importance, the RF processor FPGA 68 of FIG. 3 can be reprogrammed to exclude certain tissue processing features (such as temporal filtering, composite image processing, and/or speckle reduction processing) during color Doppler mode. Likewise, the RF processor FPGA 68 can be reprogrammed for B-Mode where only single-line acquisition is used so that multiple demodulator units and detection and compression units are excluded.

Transducer Probe Changes

In another application, software run by the CPU 52 can detect when a different transducer probe (e.g., phased-array probe, a linear probe, a curvilinear probe) is being used. It is preferred that the transducer probes used by the system contain an electronic programmable read only memory ("EPROM") that identifies the type of transducer probe being used. Alternatively, the probe identification can be hardwired to the probe connector. In operation, when a different probe is coupled with the system, the CPU 52 reads the identification information from the EPROM in the probe and optimizes the beamformer FPGA 66 and the scan converter FPGA 72, for example, for that probe type by selecting the appropriate configuration data from the disk drive 54. This provides a configuration that can be best suited for the array configuration that is used.

In addition to reprogramming the FPGAs in response to mode or probe changes, the FPGAs can be reprogrammed as part of system operations, such as between lines (or groups of lines) and between frames (or groups of frames), for examples. Of course, FPGAs can be reprogrammed for different operations. The following are non-limiting examples of how FPGAs can be dynamically reprogrammed as part of system operation.

Reprogramming between Lines

Reprogramming between lines finds particular application in color Doppler imaging where ultrasonic pulses are fired sequentially for Color Doppler image acquisition and tissue data acquisition. In color Doppler imaging, multiple scanlines are acquired for along a single scan line. One scanline corresponds to the tissue image data, and the rest of the scanlines are used to form the color Doppler image data line. Doppler processing uses data from multiple scanlines in order to extract frequency information from the data set. Distinct scanlines are collected for the tissue image versus the color Doppler image because the transmit pulse characteristics ($F_x$, $L_x$) are optimized for each image. Both the tissue image data and the color Doppler image data are processed prior to display. The processing requirements for each data set are, in general, very different.

With conventional ultrasound systems, this functionality requires additional hardware components, adding to the cost and complexity of the system. With this preferred embodiment, however, the functionality can be implemented by reconfiguring the appropriate FPGAs after each line is fired. For example, by using line-to-line reconfiguration, the beamformer FPGA 66 can be optimized for each scanline type (e.g., tissue, Color Doppler, etc.) on a pulse-by-pulse basis.

If the system software does not have a response time fast enough to reconfigure the FPGA before the start of the next pulse to enable line-to-line reconfiguration, it is preferred that a memory buffer and interface logic be used to store the input data for each processing function and any results of that function. For example, the memory buffer can store pulse and pulse-identification information. After processing the current data set (e.g., tissue data), the hardware is reconfigured and begins processing the next data set (e.g., color Doppler) also residing in a memory buffer. In this way, the FPGAs can be reprogrammed fast enough to meet the frame rate demand of this modality.

Reprogramming between Frames

In color Doppler mode, both color Doppler data as well as tissue image data is scan converted and then arbitrated to produce a final output display pixel. This creates a greater computational burden than exists in regular B-Mode imaging. To optimize the system hardware for performing these processing functions, one or more of the FPGAs can be reprogrammed. For example, since the tissue image can be of lower quality while operating in Color Doppler mode, the scan converter FPGA 72 can be reprogrammed so that a smaller kernel size (e,g., a bilinear interpolation, kernel size of four) is used instead of a larger kernel size used for B-mode imaging. In this way, the scan converter FPGA 72 can be programmed to first convert the tissue image using a larger kernel size and then be reconfigured to convert the Color Doppler image using a smaller kernel size. Unlike prior systems which provide an independent color Doppler scan converter that remains idle during B-Mode imaging, this preferred embodiment provides a system that efficiently uses its hardware.

It should be understood that the examples described above are only some of the many types of applications that can be implemented. For example, the scan converter FPGA 72 can also be reprogrammed to act as a coprocessor for converting acoustic grid data to display data when reviewing images in a quad screen format. It also should be understood that the applications described above can be used alone or in combination.

Additionally, it should be noted that any type of configuration data loader can be used as an alternative to a central processing unit. For example, a configuration data loader can comprise a state machine, a DSP, a microprocessor, an ASIC, or any other device now in existence or later developed that can be used to reprogram the reprogrammable logic device with configuration data. A configuration data loader can be used in combination with or without an associated memory device. It should also be noted that the configuration data loader can implemented, for example, as software run by a processor such as a CPU or a DMA. Further, FPGAs can be dynamically reconfigured via dedicated hardware.

In an alternate embodiment, instead of reprogramming the entire FPGA, only a portion of the FPGA. For example, if an FPGA implements a clutter filter and an autocorrelator, the FPGA can be partially reprogrammed so that the clutter filter changes but the autocorrelator remains the same.

Of course, although an FPGA was used for illustration purposes, an type of reprogrammable logic device can be used, as described above. For example, a reprogrammable logic device that allows an acceptable number of reconfigurations can be used.

RECEIVE BEAMFORMER EMBODIMENTS

FIG. 12A shows a block diagram of the receive beamformer of the ultrasound system 10. The receive beamformer 1200 is responsive to receive signals from N transducer elements labeled EL0, EL1 . . . ELN. In this embodiment the receive signals from the transducer elements are represented as a stream of data samples. The data samples may be digital data samples as described in detail in the following example, or alternately these samples may be analog samples. In either case, the samples are associated with a specified data rate, which may for example correspond to the sampling rate.

The sampled receive signals are applied to respective upsamplers 1201. The upsamplers 1201 insert additional samples between adjacent ones of the measured samples. For example, each upsampler 1201 can insert an additional sample between each pair of adjacent measured samples from the transducer elements, thereby doubling the data rate, and halving the time delay between adjacent samples. In this example the added samples supplied by the upsampler 1201 are each equal to zero. Thus, if the original samples associated with element 0 are identified as S1, S2, S3, . . . the output from the upsampler 1201 in this example is equal to S1, 0, S2, 0, S3, 0, . . . . The upsampled receive signals from the upsamplers 1201 are applied to respective time delay devices 1202. The time delay devices apply focusing delays (either dynamic or fixed) by shifting the receive signals relative to one another such that the receive signals from selected points or scan lines coherently add in a summing device 1203. The summing device 1203 forms a beamformed receive signal that is applied to a smoothing filter 1204, which smoothes the beamformed receive signal prior to further processing. In alternative embodiments, the smoothing filter 1204 may be implemented as a low pass filter or a band pass filter.

Because the upsamplers 1201 are positioned upstream of the time delay devices 1202 in the receive signal processing path, the time delay devices 1202 operate with a higher resolution than would be possible in the absence of upsampling. This contributes to improved focusing characteristics. Because the smoothing filter 1204 is positioned after the summer 1203 in the receive processing path, a single smoothing filter 1204 can be used. In contrast, if the smoothing filter 1204 were positioned between the upsamplers 1201 and the time delay devices 1202, n separate smoothing filters would be required, at a substantial increase in cost and complexity.

FIG. 12B provides a more detailed block diagram of initial portions of the receive signal processing path of the receive beamformer 1200 for two channels associated with element 0 and element 1. In an actual system, the receive beamformer may include many more channels, such as 64 in this example. As shown in FIG. 12B, the transducer signals from the respective transducer elements are applied to A to D converters 1205 that are clocked at a selected frequency, such as 21.5 MHz or 43 MHz in this example. The A to D converters 1205 are included in the receiver 14 discussed above.

The A to D converters 1205 generate sampled receive signals that are applied to respective input stages 1206. The input stages register the incoming sampled receive signals and convert the sampled receive signals from offset binary to two's complement numbers. In addition, the input stages 1206 upsample the sampled receive signals by adding a zero sample between each adjacent pair of samples from the A to D converter 1205. Thus, the input stages 1206 function as upsamplers. Additionally, the input stages 1206 actively drive the output to zero during the time when the associated A to D converter 1205 is in the sleep mode or until the associated transducer element has been turned on to contribute to the beam sum.

Figure 12C:
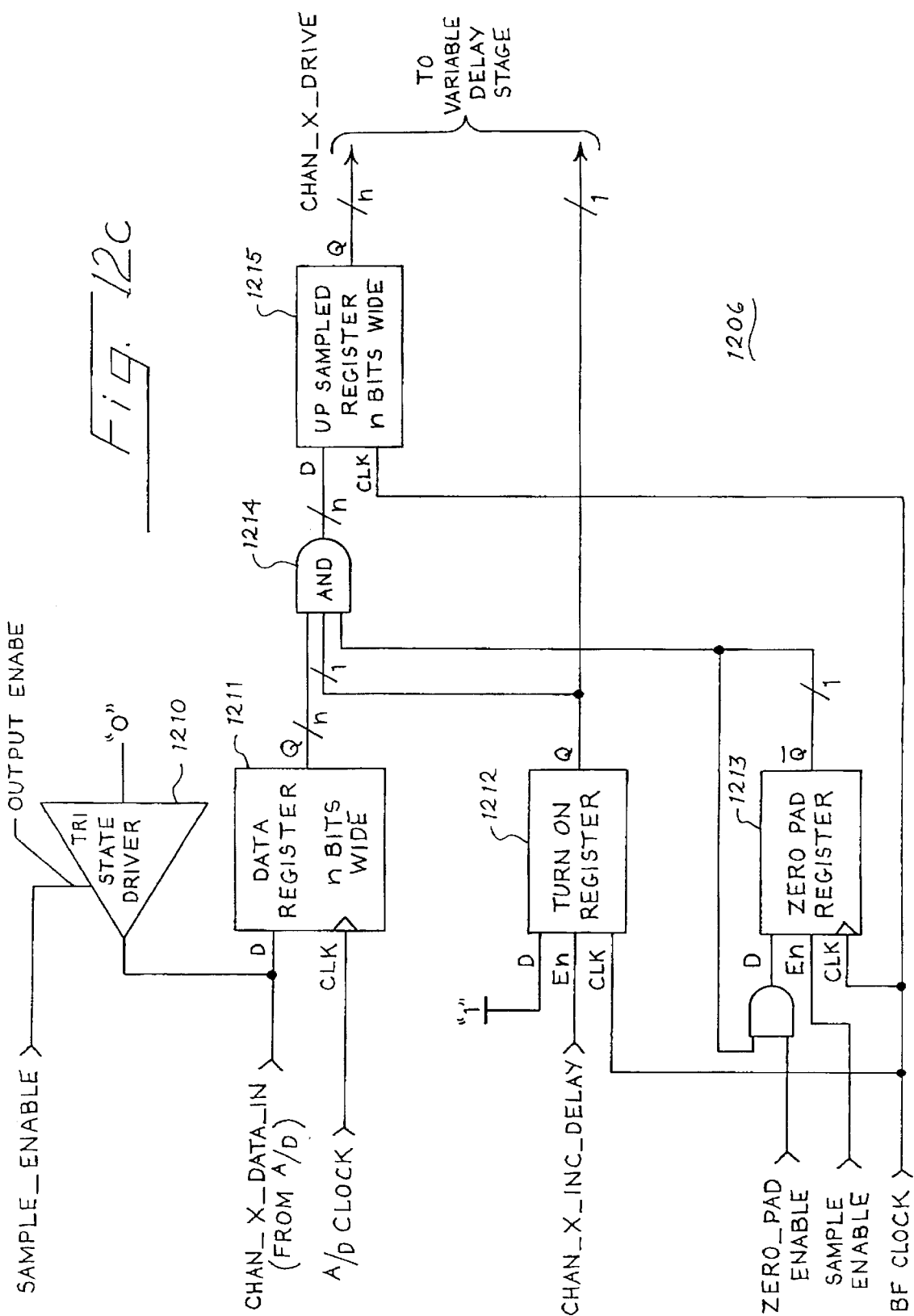
FIG. 12C is a block diagram of one of the input stages of FIG. 12B.

Further information regarding the input stage 1206 is provided in FIG. 12C. The input stage 1206 of FIG. 12C includes a tri-state driver 1210 that is used to prevent the input of the beamformer from drifting to an unknown state during sleep modes when the output of the A to D converters are turned off. This state only applies when the sample_ enable signal goes inactive. The data register 1211 transfers receive signals from the A to D converter for the respective channel to the AND gate 1214, clocked by the A to D clock, and selectively overridden by the tri-state driver 1210.

The AND gate 1214 performs three functions. First, it causes data in the channel to be held at zero until the turn-on register 1212 goes active. Second, the AND gate 1214 converts data from the offset binary format of the A to D converter to a two's complement format. Finally, when zero padding is enabled the AND gate 1214 inserts a data value of zero at every other cycle of the BF clock.

The turn-on register 1212 is a single-bit register that goes active when it is enabled by the increment delay signal for the respective channel. Once activated, the register 1212 remains on until an end-of-line reset occurs. The output of the register 1212 also feeds a single-bit shift register in the variable delay stage that controls delay stepping. Thus, the initial activation of a channel and delay stepping are handled by the same register 1212, thereby saving hardware and control complexity.

The zero pad register 1213 is a single-bit register that operates in one of two modes depending upon the status of the input signal zero_pad_enable. When this signal is false (zero padding not enabled), the output of the register 1213 remains fixed and the AND gate 1214 passes data normally without upsampling. However, when the zero_pad_enable signal is true, the output of the register 1213 toggles between true and false on every cycle of the BF clock. This causes the AND gate 1214 to output a data value of zero on alternate clock cycles. Note that in this mode the BF clock is running at two times the rate of the A to D clock. The output of the AND gate 1214 is passed by the register 1215, clocked by the BF clock.

The upsampled receive signals from each input stage 1206 are applied to the respective variable delay stage 1207. The variable delay stages 1207 perform dynamic focusing during reception of receive signals from a given transmit event. The length of the variable delay varies as a function of the geometric location of the transducer element in the transducer array for the respective channel. For a phased array beamformer, the outer channels associated with transducer elements near the edge of the array require the longest variable delays, while the central channels associated with transducer elements near the center of the transducer array require substantially shorter variable delays. The input signal Chan X inc delay causes the variable delay stage to increase the delay by a single clock cycle of the BF clock every time the Chan X inc delay signal is asserted.

Figure 12D:
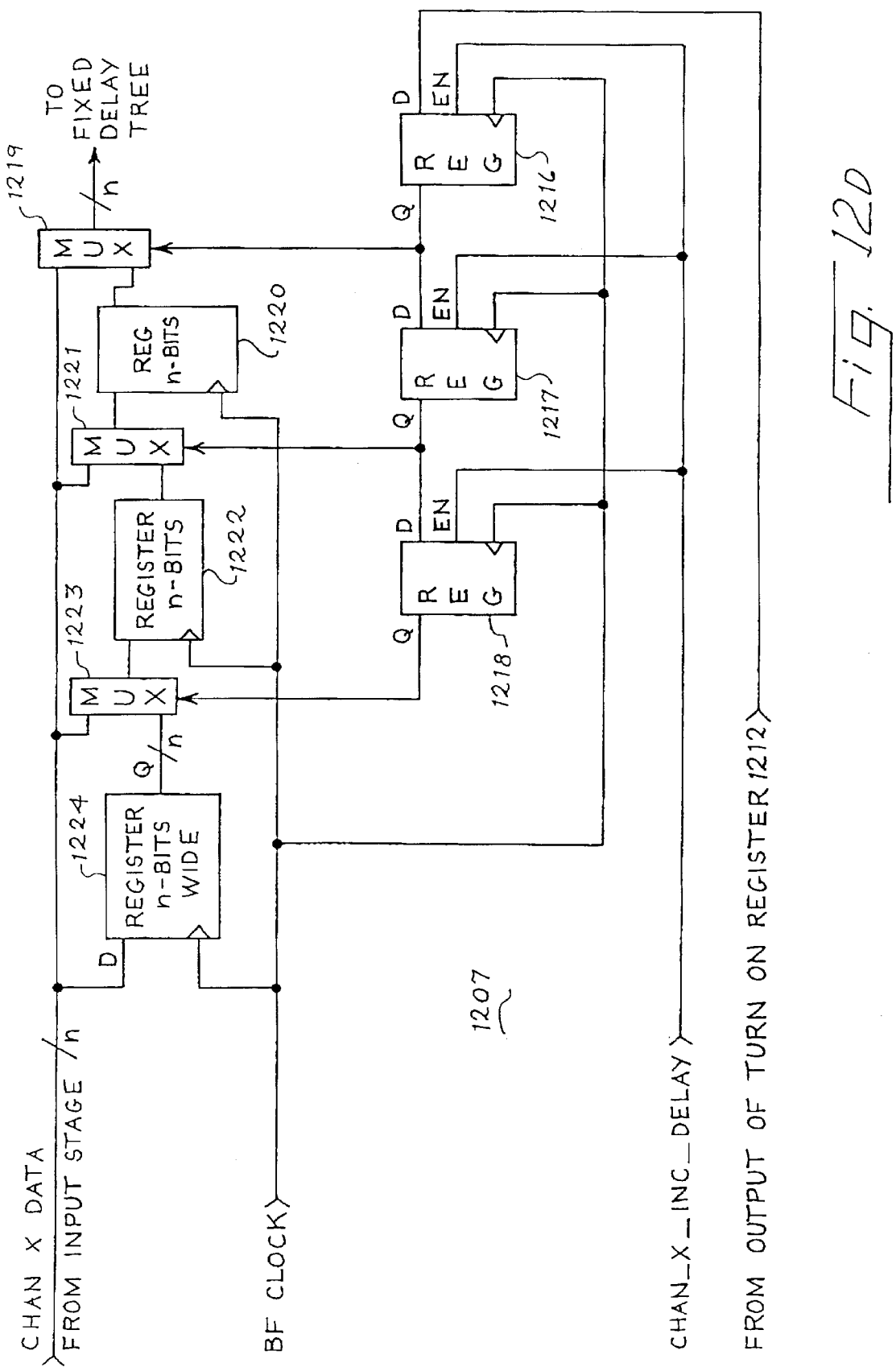
FIG. 12D is a block diagram of one of the variable delay stages of FIG. 12B.
Figure 12E:
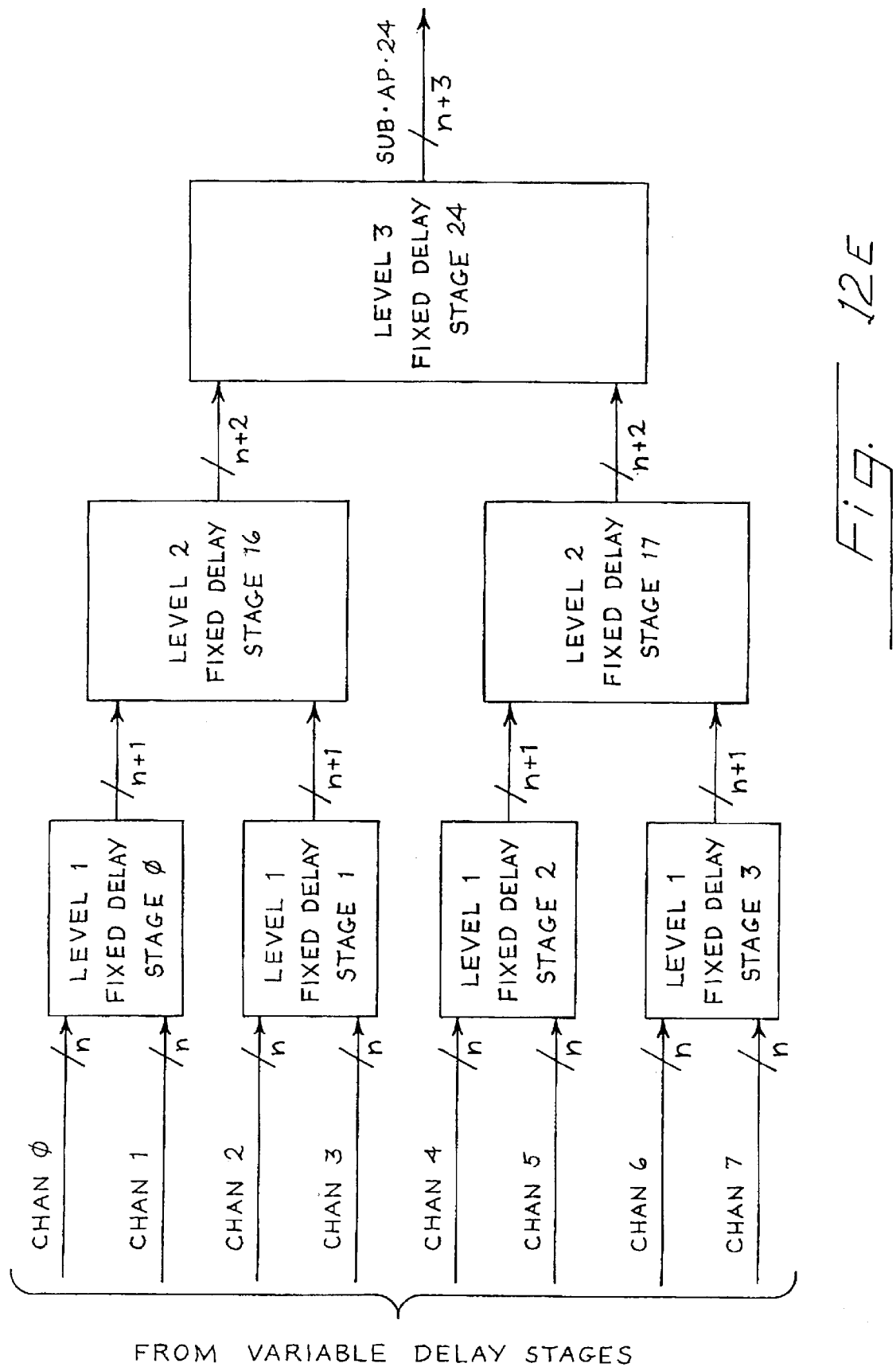
FIGS. 12E–12L are more detailed block diagrams of portions of the time delay devices and the summer of FIG. 12A.
Figure 12F:
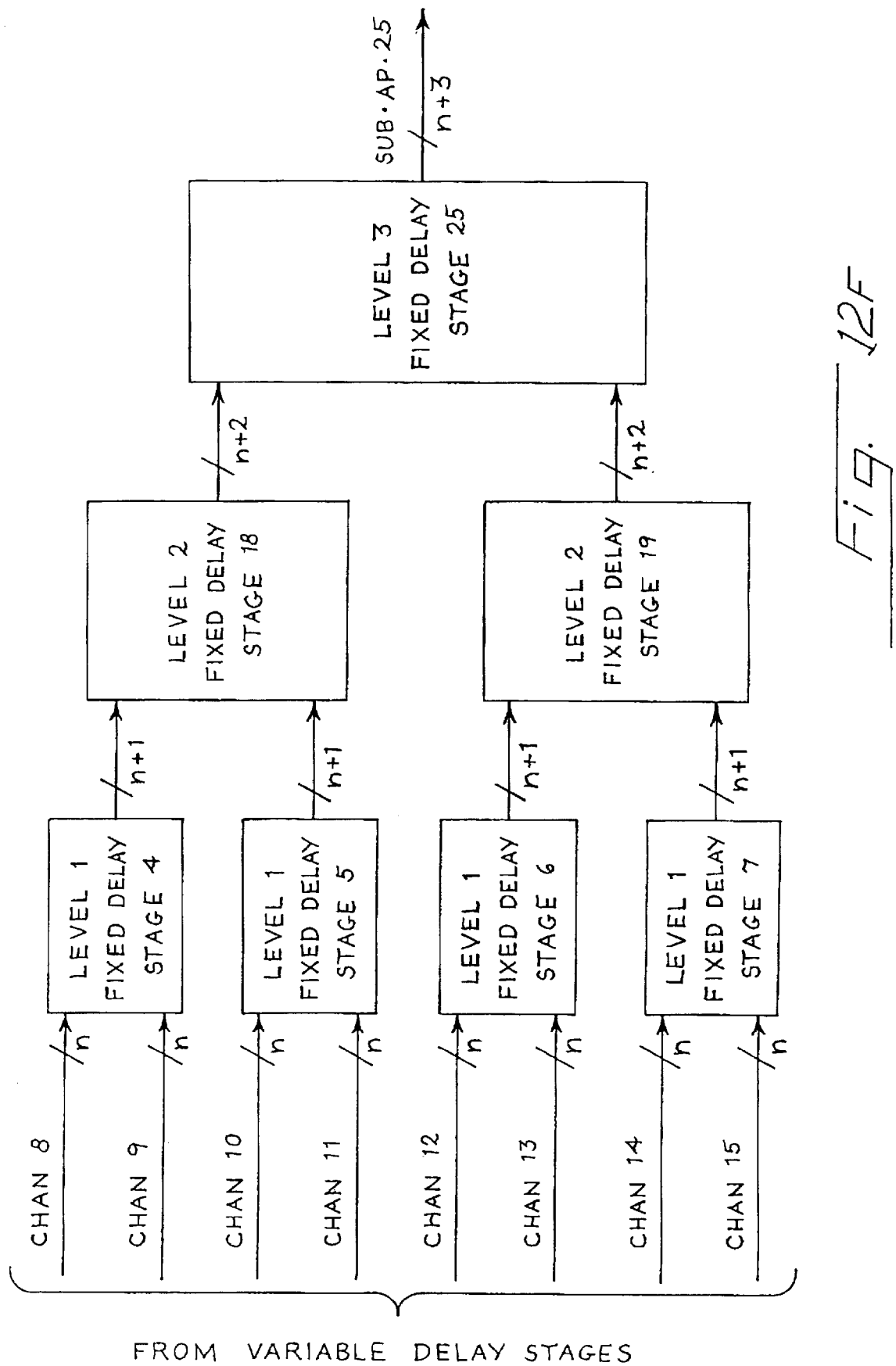
Figure 12G:
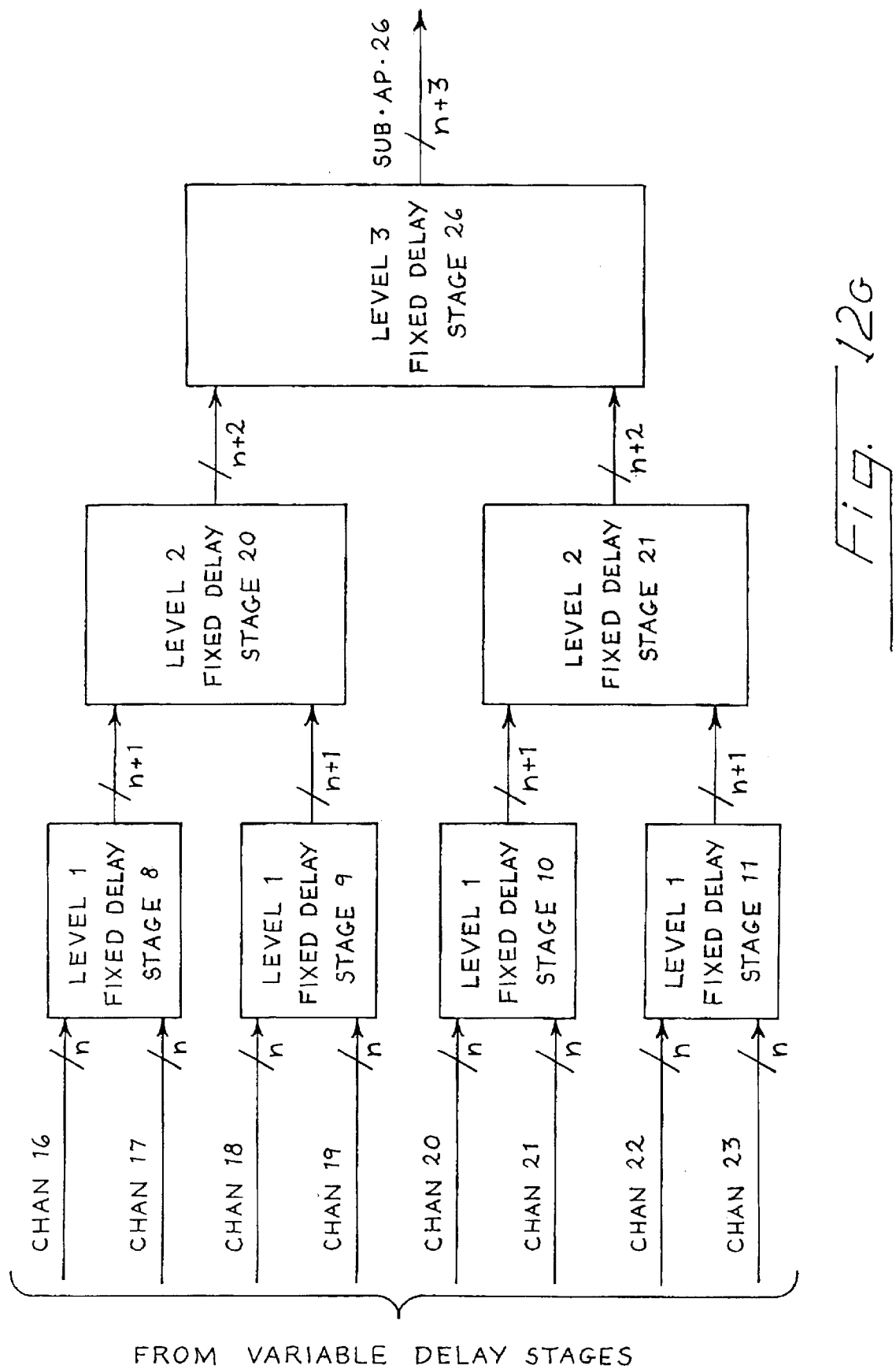
Figure 12H:
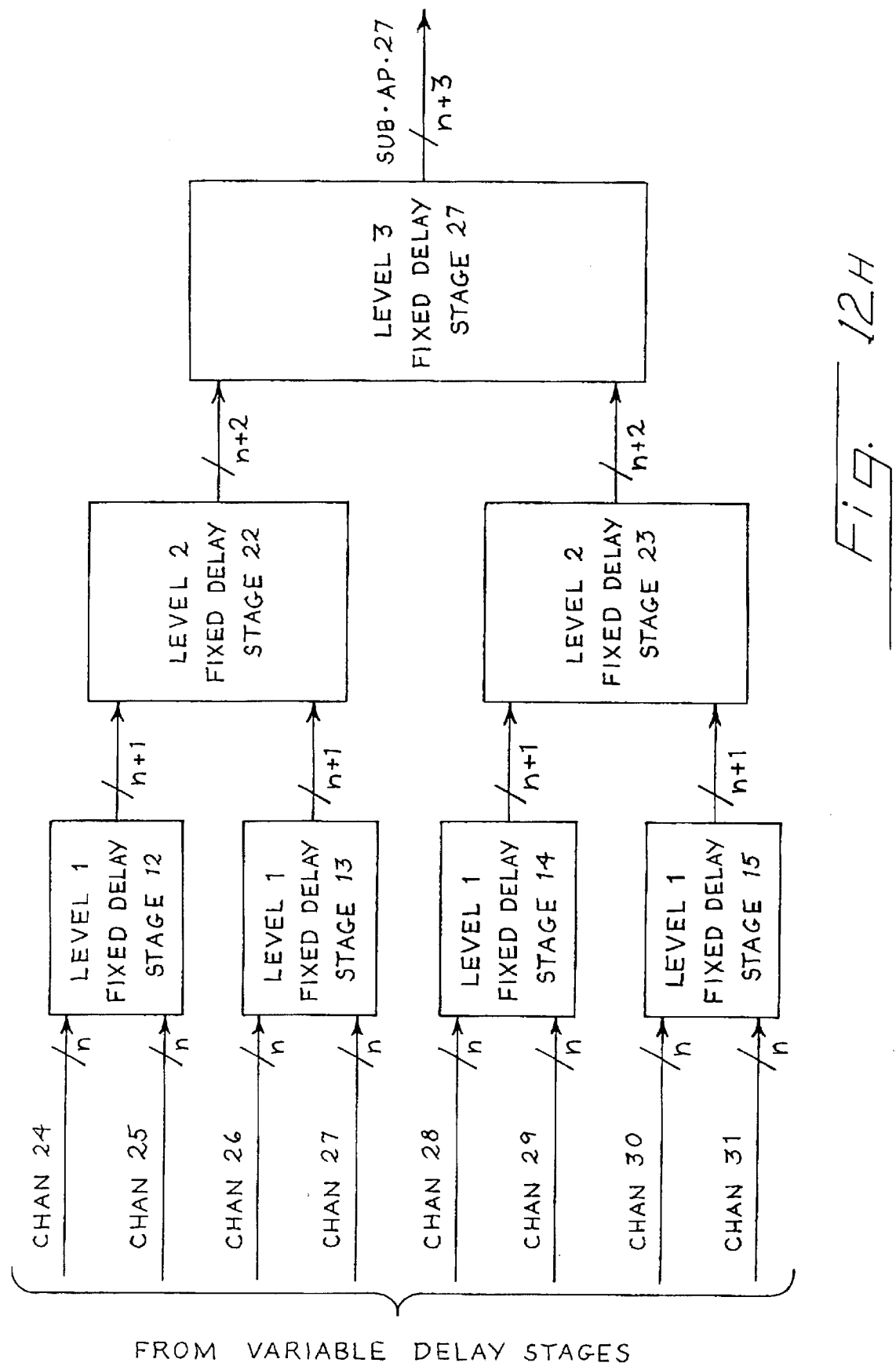
Figure 12I:
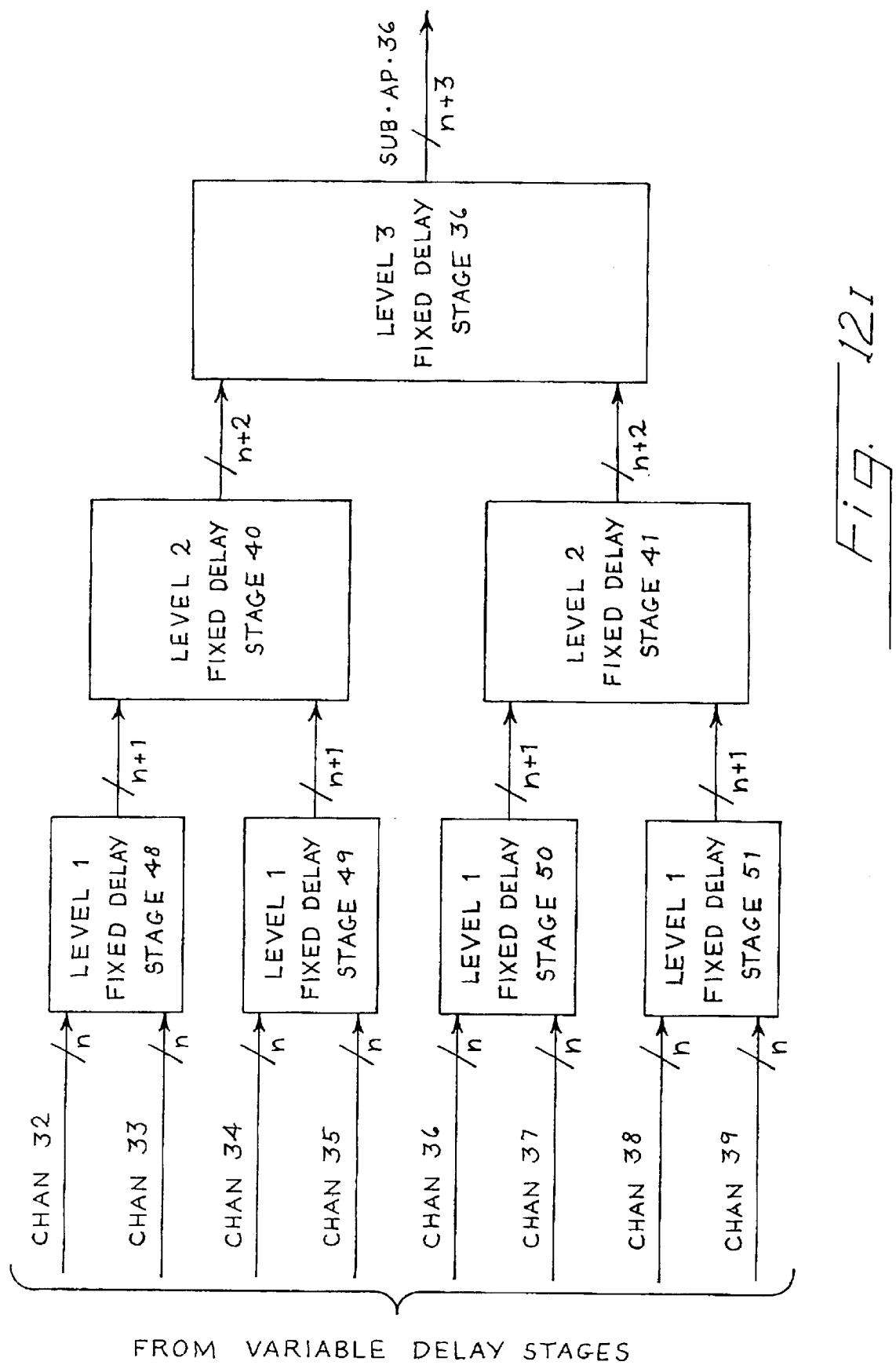
Figure 12J:
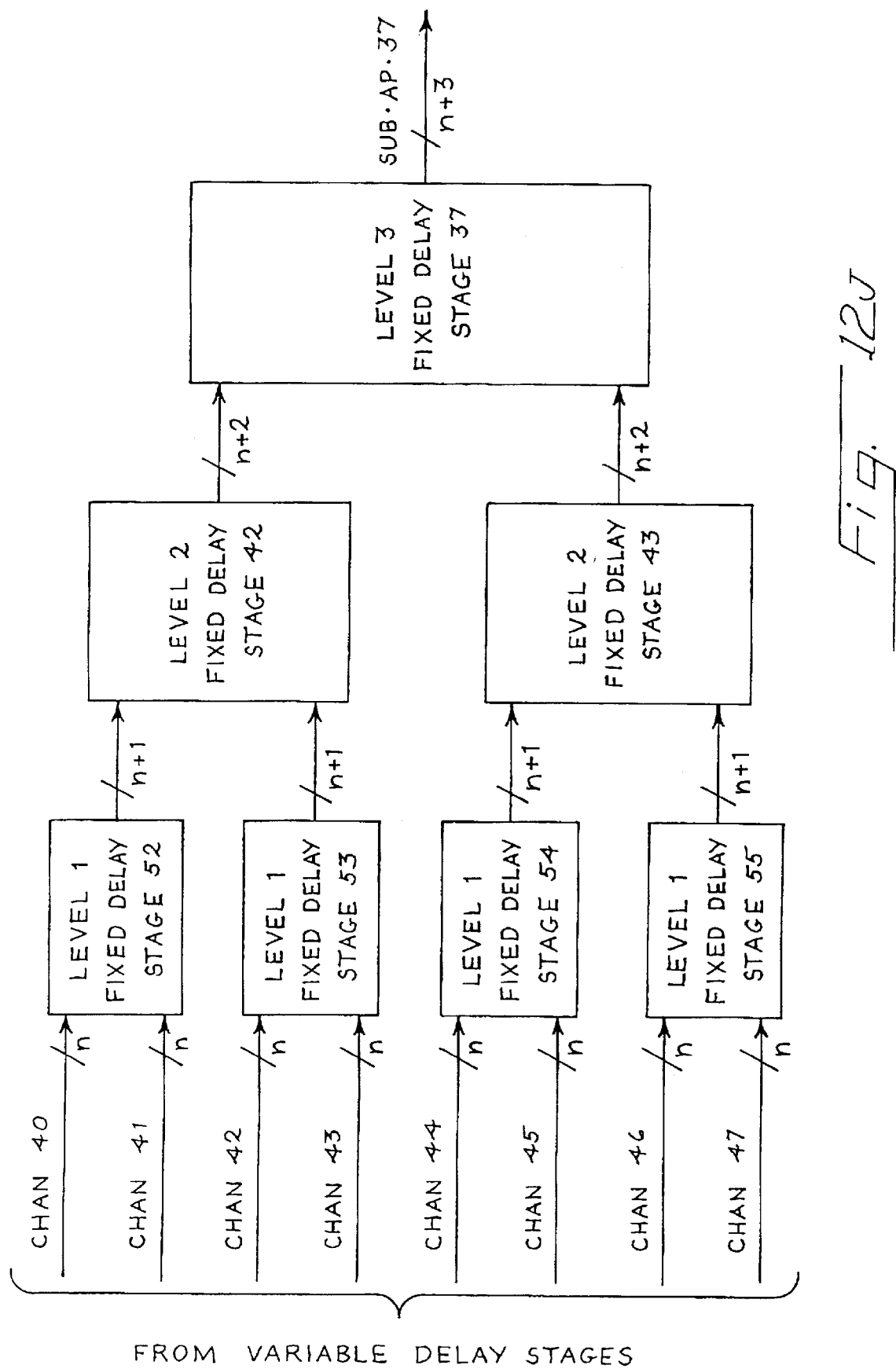
Figure 12K:
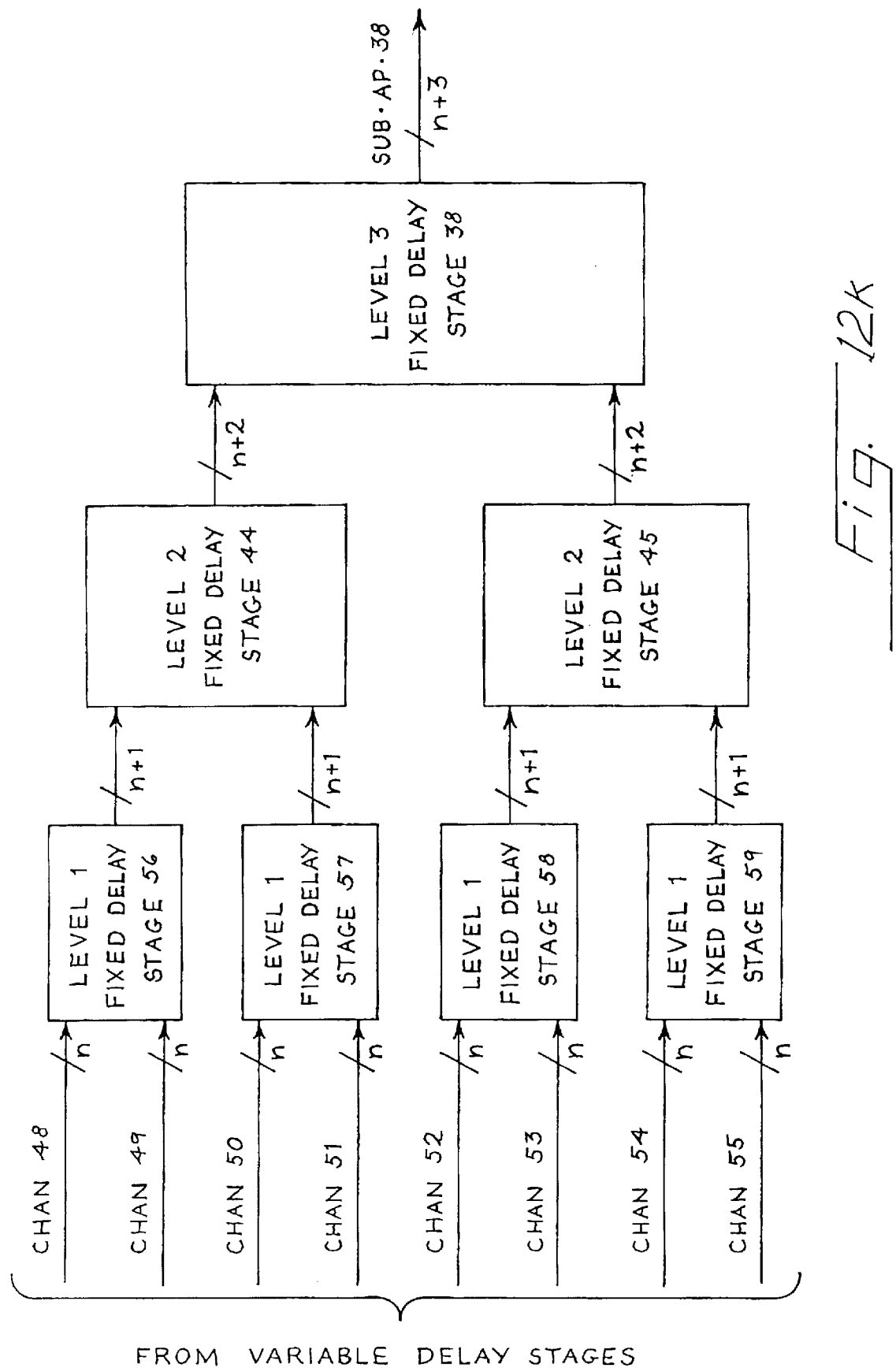
Figure 12L:
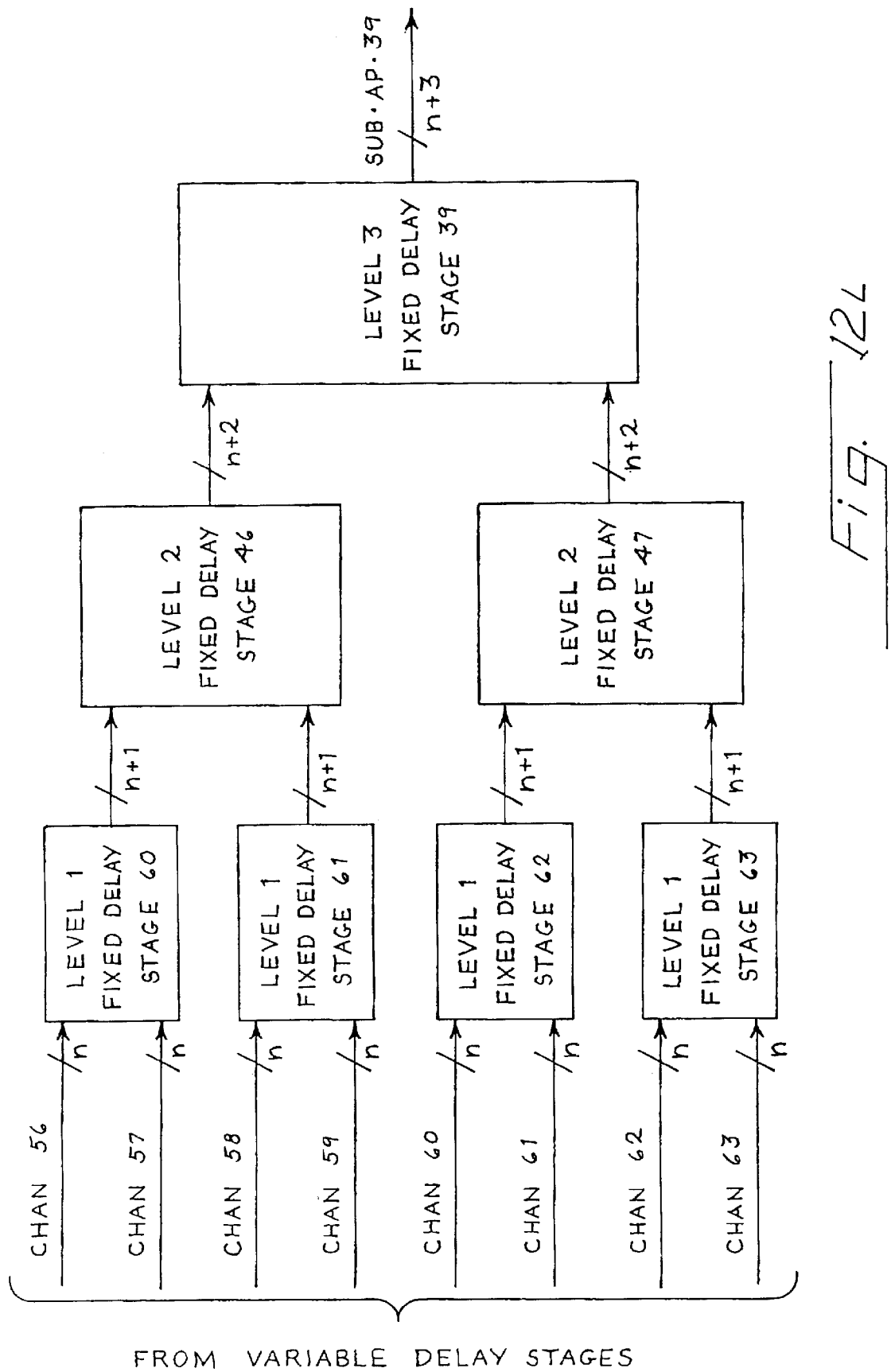

Further information regarding the variable delay stages 1207 is provided in FIG. 12D. The variable delay stage 1207 of FIG. 12D includes a variable delay channel with a maximum delay of three cycles of the BF clock. Longer delays can of course be provided by continuing the scheme shown in FIG. 12D to include more registers 1216, 1217, 1218, 1220, 1222, 1224 and more multiplexers 1219, 1221, 1223. In the initial state at the start of each scan line, the multiplexers connect the upper input with the respective multiplexer output. The output from the turn-on register 1212 is applied as a data input to the register 1216. The Chan_X_inc_delay signal, when asserted, enables the registers 1216, 1217, 1218, which form a single-bit wide shift register that starts with the register 1216 and flows from right to left. The first time a channel receives its Chan_X_inc_delay signal while the output of the turn on register 1212 is true, the register 1216 shifts state, thereby causing the multiplexer 1219 to pass the data from the register 1220. Each successive time the Chan_X_inc_delay signal goes active for the respective channel while the output of the turn on register is true, an additional one of the registers 1217, 1218 (proceeding from right to left) changes state, thereby causing another one of the multiplexers 1221, 1223 to select the delayed data from the previous register 1222, 1224. In this way, delays equal to 0, 1, 2 or 3 times the BF clock cycle can be imposed upon the data from the input stage.

Table 2 provides by way of non-limiting example a list of the maximum variable delay length that is provided by the variable delay stages 1207 (in clock cycles) as a function of the channel number. Channel numbers 0, 1, 2 . . . 63 are associated with transducer elements progressively farther from one edge of the array. Thus, channel numbers 0 and 63 are associated with transducer elements at the edges of the array and channel numbers 31, 32 are associated with transducer elements at the center of the array.

TABLE 2

Variable Delay Stage: Delay Lengths

| CHANNEL NUMBER | MAX VARIABLE DELAY LENGTH |
|---|---|
| 0 | 63 | 13 |
| 1 | 62 | 13 |
| 2 | 61 | 12 |
| 3 | 60 | 12 |
| 4 | 59 | 12 |
| 5 | 58 | 11 |
| 6 | 57 | 11 |
| 7 | 56 | 11 |
| 8 | 55 | 10 |
| 9 | 54 | 10 |
| 10 | 53 | 9 |
| 11 | 52 | 9 |
| 12 | 51 | 9 |
| 13 | 50 | 8 |
| 14 | 49 | 8 |
| 15 | 48 | 7 |
| 16 | 47 | 7 |
| 17 | 46 | 7 |
| 18 | 45 | 6 |
| 19 | 44 | 6 |
| 20 | 43 | 5 |
| 21 | 42 | 5 |
| 22 | 41 | 4 |
| 23 | 40 | 4 |
| 24 | 39 | 4 |
| 25 | 38 | 3 |
| 26 | 37 | 3 |
| 27 | 36 | 2 |
| 28 | 35 | 2 |
| 29 | 34 | 1 |
| 30 | 33 | 1 |
| 31 | 32 | 0 |

The specific values of Table 2 are suitable for one preferred embodiment using a $\lambda/2$ phased array and a minimum F-number equal to 2. If a smaller F-number were desired, a longer maximum variable delay length would be provided.

The time delay devices described above include first and second time delay devices associated with central and peripheral elements of the transducer array, respectively. Note that the maximum time delay M provided by a first, central time delay device (e.g., channel 30) is less than the maximum time delay N provided by a second, peripheral time delay device (e.g., channel 61).

The upsampled receive signals from the variable delay stages 1207 are applied to a series of fixed delay stages 1208 organized in levels 1–6. These fixed delay stages 1208 apply fixed delays to steer and provide initial focusing of the receive beam. The fixed delay stages 1208 are arranged in a delay tree where the maximum amount of delay at each level of the tree doubles from that of the previous level. This approach reduces the total number of delay elements required by taking advantage of the fact that the differential delay between two adjacent sub-apertures has a lower maximum value than the delay across the entire aperture. Thus, instead of providing a full-length delay line for each channel, only the maximum differential delay at any given sub-aperture size is provided.

Figure 12M:
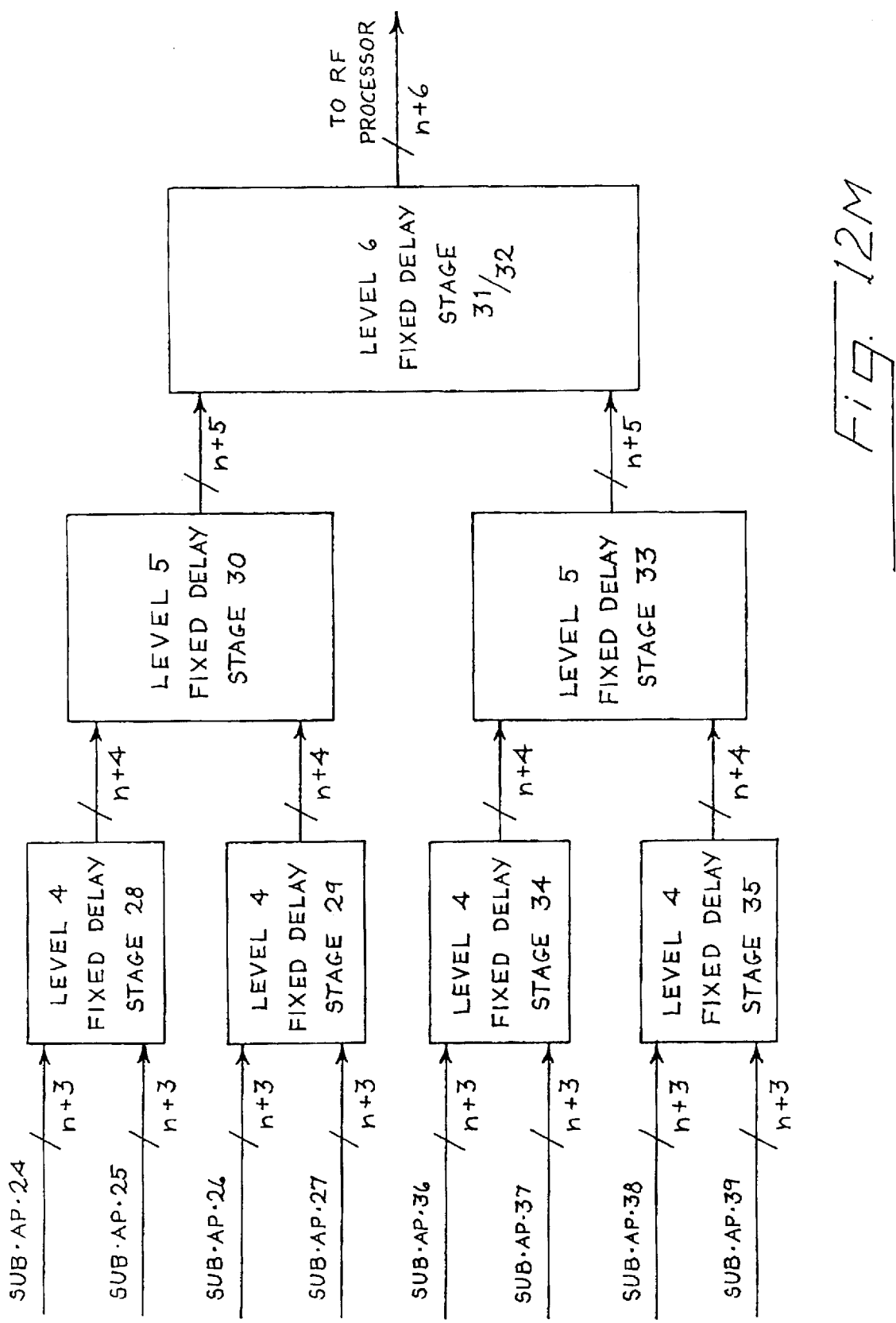
FIG. 12M is a more detailed block diagram of additional portions of the time delay devices and the summer of FIG. 12A.

FIGS. 12E–12L show levels 1, 2 and 3 of the delay tree. FIG. 12M shows levels 4, 5 and 6 of the delay tree. Stage 0 of FIG. 12B corresponds to Stage 0 of FIG. 12E. The receive signals generated by stage 31/32 (FIG. 12M) are fully beamformed (delayed and summed) receive signals.

The variable delay stages 1207 and the fixed delay stages 1208 can be considered as included in the time delay devices 1202 of FIG. 12A, and the summing components included in the fixed delay stages 1208 can be considered as included in the summer 1203 of FIG. 12A.

Figure 12P:
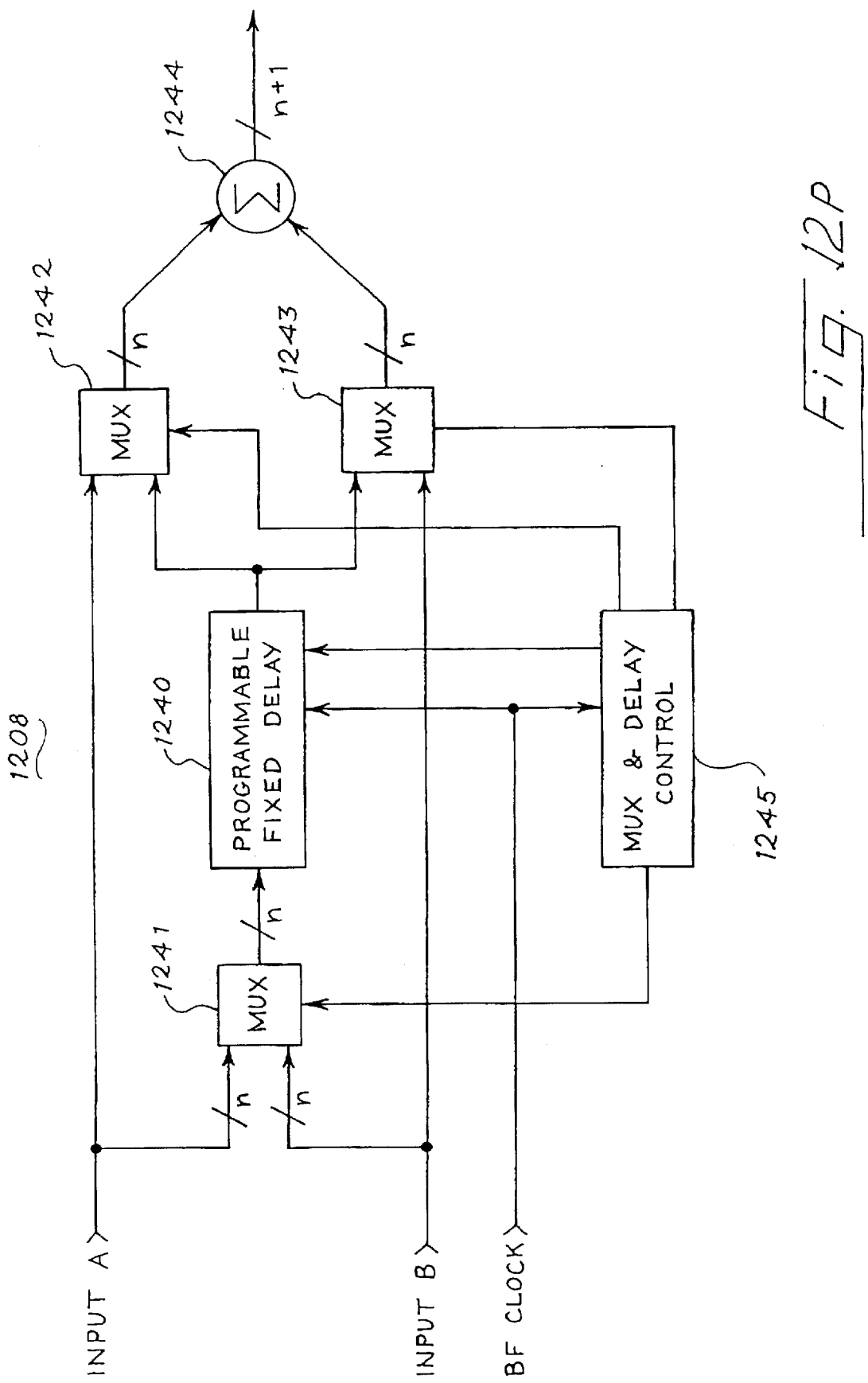
FIG. 12P is a more detailed block diagram of one of the fixed delay stages of FIGS. 12B–12M.

Further details regarding a preferred structure of a fixed delay stage 1208 are shown in FIG. 12P. Each fixed delay stage 1208 includes a programmable fixed delay device 1240, and a first multiplexer 1241 determines which of the two inputs to the fixed delay stage 1208 is to be applied as an input to the programmable fixed delay device 1240. The programmable fixed delay device delays the selected input signal a selected number of clock cycles, as determined by the control 1245. The output of the programmable fixed delay device 1240 is applied to second and third multiplexers 1242, 1243. These multiplexers 1242, 1243 are controlled by the control 1245 to cause one of the two inputs A or B and the time delayed other of the two inputs A or B to be summed at the summer 1244.

The output of the level 6 fixed delay stage 31/32 (FIG. 12M) is applied to a RF processor 1226 shown in FIG. 12N. This RF processor 1226 is included in the RF processor 22 discussed above. The RF processor 1226 includes first and second mixers 1227, 1229 that mix the beamformed receive signal with a digital sine signal from a sine signal source 1228, and a digital cosine signal from a cosine signal source 1230, respectively. The mixers 1227, 1229 convert the RF beamformed receive signals to baseband by multiplying the beamformed receive signal by digitized sine and cosine waveforms at the center frequency of the frequency range of interest. The outputs of the mixers 1227, 1229 are filtered with identical low pass filters 1231, 1232, respectively. The filters 1231, 1232 may for example be FIR low pass filters that integrate the information in the data stream across many samples. This has the effect of smoothing any variations in the beamformed receive signals that result from the upsampling operations performed in the input stages 1206 described above. By way of example, suitable coefficients for the low pass filters 1231, 1232 may be as follows:

[−0.00056 −0.00147 −0.00294 −0.00442 −0.00560 −0.00606 −0.00588

−0.00515 −0.00105 0.00486 0.01395 0.02282 0.03582 0.04810

0.06247 0.07356 0.08457 0.09139 0.09559 0.09559 0.09139

0.08457 0.07356 0.06247 0.04810 0.03582 0.02282 0.01395

0.00486 −0.00105 −0.00515 −0.00588 −0.00606 −0.00560 −0.00442

−0.00294 −0.00147 −0.00056]

These coefficients provide a linear phase low pass filter with −3 dB frequency cutoff of $0.087 \times \pi$, and a minimum stopband attenuation of −45 dB. The filters 1231, 1232 and the mixers 1227, 1229 correspond to one embodiment of the smoothing filter 1204 of FIG. 12A.

FIG. 12O illustrates a method performed by the beamformer 1200 described above. As shown in FIG. 12O, receive signals are upsampled at 1233. Then focusing delays are applied at 1234 and a beam sum is formed at 1235. The beam-summed receive signals are then filtered at 1236 with a smoothing filter.

Figure 12Q:
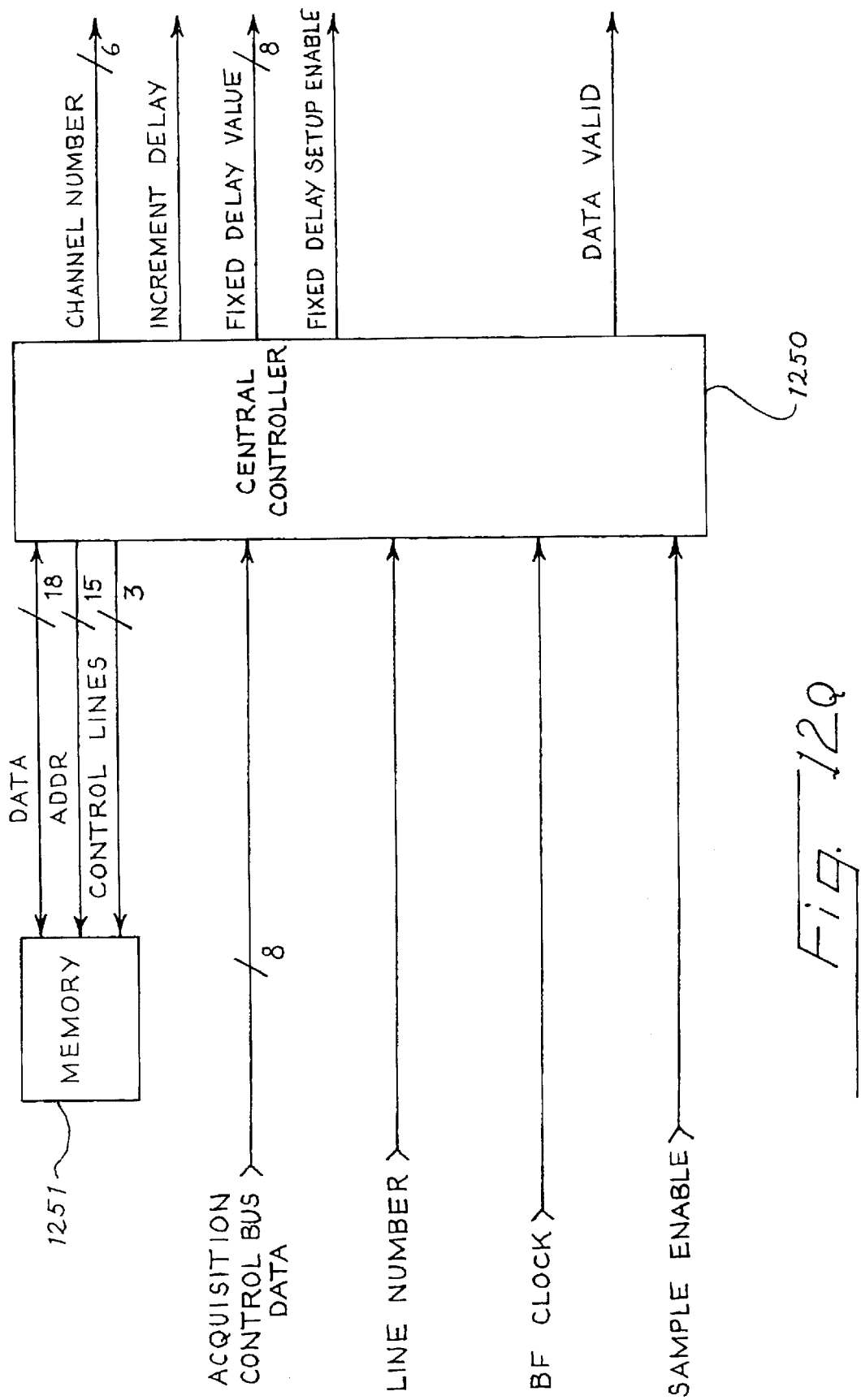
FIGS. 12Q and 12R are block diagrams of a central controller and a local controller, respectively, of the beamformer of FIG. 12A.

As shown in FIG. 12Q, the receive beamformer described above is controlled by a central controller 1250 connected to a memory 1251. The central controller 1250 is capable of storing desired parameters from the acquisition control data bus into the memory 1251, as well as of subsequently reading values from the memory 1251. The central controller also receives the BF clock signal described above, a line number signal that defines the scan line number to be received, and a sample enable signal that provides a start signal for each scan line.

The central controller 1250 uses the line number signal to retrieve appropriate parameters from the memory 1251 for the scan line to be received. For example, the memory can be a 32K by 32 SRAM. These parameters include words from the memory 1251 that define the fixed delay values and the channel number for each of the channels of the system. In this example, each fixed delay value is an 8-bit value, and the channel number is a 6-bit value, though other bit sizes can be used. The central controller also retrieves from the memory 1251 a set of range values for each channel (each 12 bits in length in this non-limiting example). The range values indicate the range at which the associated channel is to be turned on, and the successive ranges at which the variable delay is to be increased by one clock cycle. The central controller maintains a range counter that is incremented from a time defined by the sample enable signal at a rate determined by the BF clock signal. In this example the BF clock signal has a frequency eight times greater than the center frequency of interest. For example, when the receive beamformer is used to receive 2.7 MHz ultrasonic signals, the BF clock signal has a frequency of 21.5 MHz.

Prior to each line acquisition there is a setup phase during which the central controller 1250 retrieves from the memory 1251 the fixed delays that are appropriate for each of the fixed delay stages 1208 and the respective scan line. These delay values are written into each fixed delay stage 1208 sequentially. The fixed delay values provide the programmable delay values for each of the fixed delay stages 1208 described above. These fixed delay values insure that the receive signals are steered along the desired scan line and focused at the desired initial depth when the respective channels are first turned on.

Figure 12R:
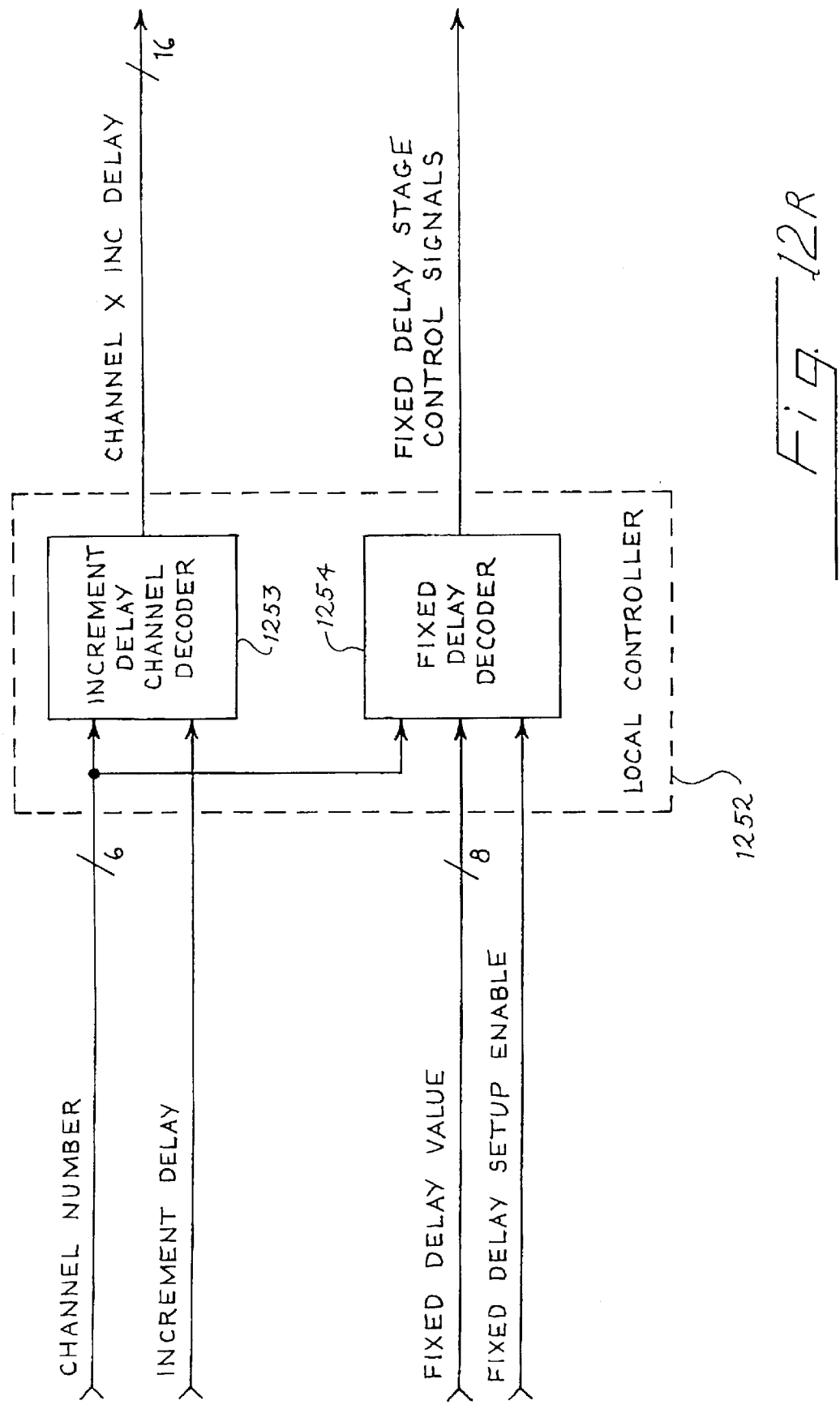
Figures 12S, 12T:
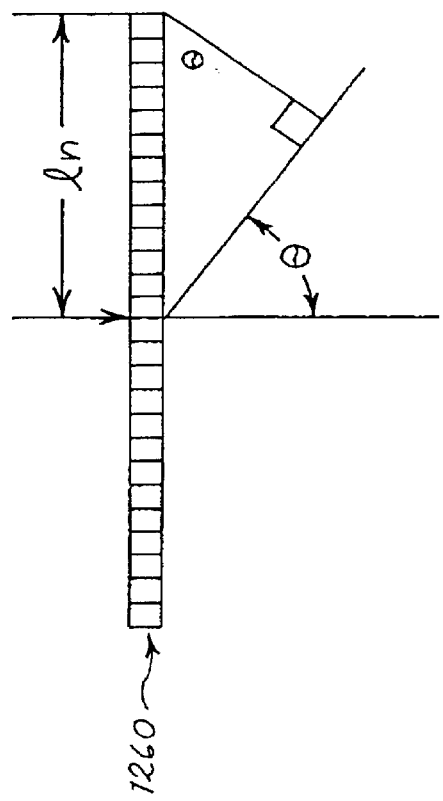
FIG. 12S is a chart providing information regarding the fixed delay stages of FIGS. 12B–12M.
FIG. 12T is a schematic diagram of a phased array transducer suitable for use with the beamformer of FIG. 12A.

In order to insure that dynamic focusing can be achieved with a monotonically increasing delay in the variable delay stages 1207 throughout the entire scan line, each channel is not turned on until the range is equivalent to or greater than a minimum range that equals the distance from the transducer element to the center of the transducer array times sin 2 (FIG. 12T). In FIG. 12T the phased array transducer is indicated at 1260. Thus, in this non-limiting example, channels are initially enabled only near the center of the transducer array, and they are progressively enabled to maintain an F-number equal to or greater than two as the focusing range increases.

The data valid output of the central controller 1250 indicates that the beamformed receive signal from level 6 fixed delay stage 31/32 represents a valid beamformed signal for further processing.

Selected output signals of the central controller 1250 are applied to four local controllers 1252, one of which is shown in FIG. 12R. Each local controller 1252 includes an increment delay channel decoder 1253 and a fixed delay decoder 1254. The increment delay channel decoder 1253 generates 16 channel increment delay signals Chan_X_inc_delay. Each of these delay signals is applied to a respective one of the variable delay stages 1207 to cause the respective variable delay stage 1207 to increment the amount of variable delay.

The fixed delay decoders 1254 program the multiplexer and delay control 1245 of each of the fixed delay stages 1208, specifying the state of the multiplexers 1241, 1242, 1243, and the programmable fixed delay to be applied by the delay device 1240.

The combination of a central controller 1250 and a local controller 1252 can vary widely depending upon the application. In some examples, the central controller 1250 can perform all control functions, including those performed by the local controller 1252. At the other extreme, there can be a separate controller for each of the variable delay stages 1207 and/or the fixed delay stages 1208.

In the non-limiting example defined by the attached microfiche appendix, the central controller 1250 is designed to increase the variable delay on only a single channel at any given clock cycle. If multiple channels require an increase in the variable delay on the same clock cycle, then the channels requiring an increase in delay are placed in a queue and are updated on successive clock cycles. Alternatively, simultaneous updates can be implemented with a multi-channel controller.

The receive beamformer 1200 described above provides dynamic focusing. That is, the focus of the beamformer is progressively modified from shorter ranges to longer ranges as a scan line is received. Such a dynamic focus beamformer is well suited for certain modes of operation such as B-mode operation.

The receive beamformer 1200 is implemented as a reprogrammable gate array. The variable delay stages 1207 described above consume a large number of gates in the gate array. The present inventors have recognized that the gate array may be reprogrammed, depending upon the mode of operation of the beamformer, to optimize beamformer performance. As described above, a dynamic focusing beamformer is preferred for B-mode operation. However, in other modes of operation such as the color flow mode, a fixed focus is acceptable. Some color flow mode applications also benefit from a high rate of scan line acquisition. In order to optimize the receive beamformer 1200 for both B-mode operation and high frame rate color flow mode operation, it is preferred to reprogram a field programmable gate array in accordance with the user-selected mode.

Figure 12U:
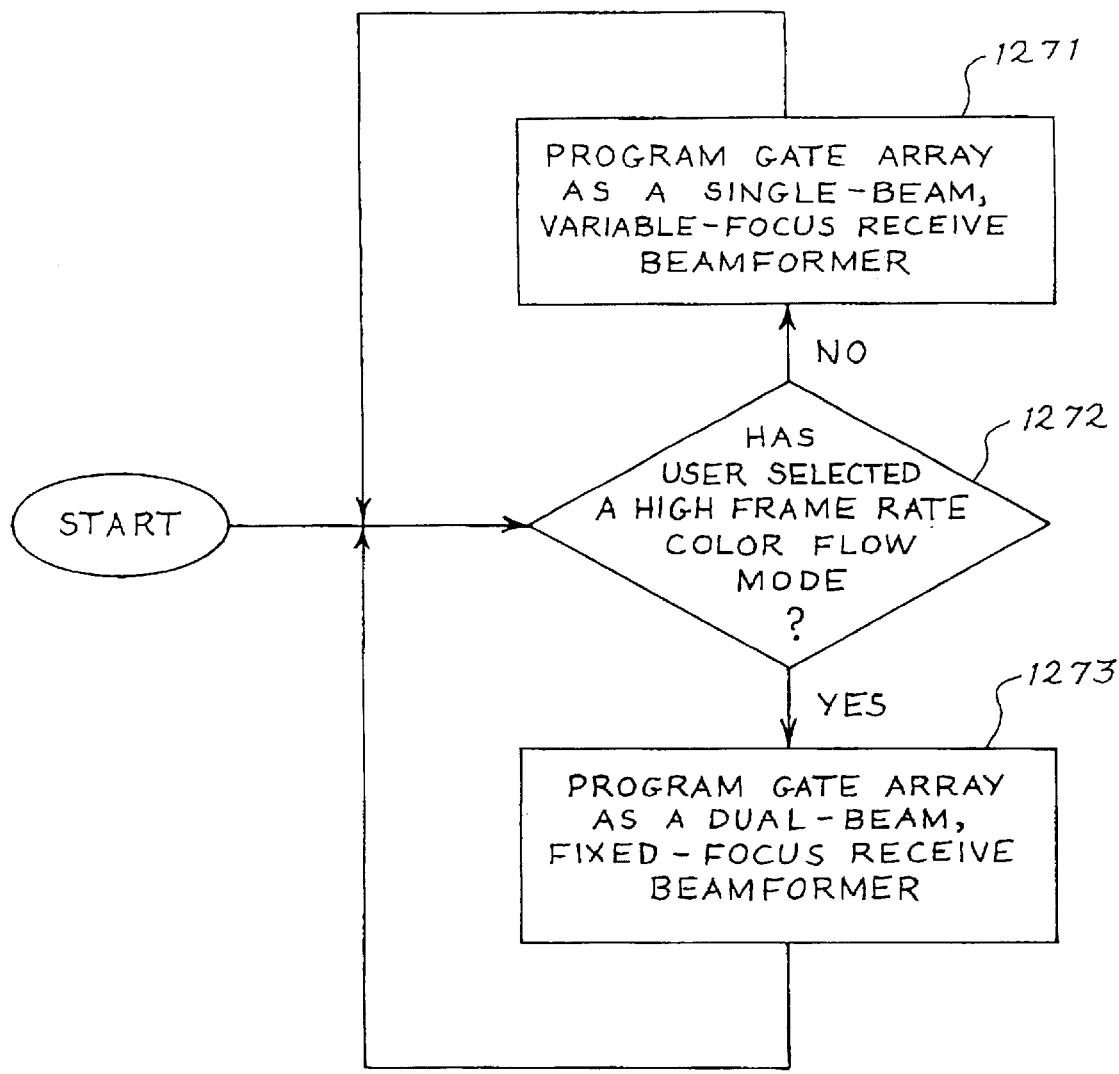
FIG. 12U is a flow chart of a method for programming the receive beamformer of FIG. 12A in a field programmable gate array.

As shown in FIG. 12U, when the user selects a high frame rate color flow mode of operation at 1272, a central controller automatically programs the field programmable gate array as a dual-beam, fixed-focus receive beamformer at 1273. Alternately, when the user selects another mode of operation (e.g. B-mode), the controller automatically programs the field programmable gate array as a single-beam, dynamic-focus receive beamformer at 1271. This single-beam, dynamic-focus receive beamformer can be identical to that described above in conjunction with FIGS. 12B–12S. The dual-beam, fixed-focus receive beamformer programmed at 1273 is programmed by forming two receive beamformers which are substantially identical to the receive beamformer described above in conjunction with FIGS. 12B–12S, except that the variable delay stages 1207 are not used, and the output signals from the input stages 1206 are applied in parallel to two separate delay trees comprising fixed delay stages 1208 as described above.

Additionally, the fixed delay stages 1208 are programmed to have a smaller maximum delay length than that shown in FIG. 12S discussed above. The reprogrammed level 1 fixed delay stages have a maximum delay length of two, and levels two through six have maximum delay lengths of 4, 8, 16, 32 and 64, respectively. By reducing the maximum delay length of the fixed delay stages, the number of gates required to implement the delay tree is reduced. As a consequence of the reduced maximum delay length of the fixed delay stages, the maximum steering angle is reduced from 45° to 30°. However, this reduction is clinically acceptable in color flow imaging.

The method of FIG. 12U uses the flexibility of a field programmable gate array to optimize the receive beamformer for B-mode operation as well as for color flow mode operation. In general, the dynamic-focus beamformer can form M simultaneous beams and the fixed-focus beamformer can form N simultaneous beams, where N>M. For example, M can equal 2 and N can equal 3, 4 or some other integer greater than 2. User selection of B-mode operation can be taken as one example of user selection, and user selection of color flow mode operation can be taken as another example of user selection.

It should be apparent from the foregoing detailed description that an improved beamformer has been described that provides high resolution time delay and excellent beamformation using relatively low power, low cost, A to D converters. This is accomplished by using upsamplers prior to the time delay devices. This advantage is obtained without unduly increasing the circuitry required for smoothing filter, because the smoothing filter is positioned after the beam sum is formed. In alternative embodiments, the smoothing filters can operate on partially beam summed receive signals rather than on the completely beam summed receive signals described above. Because a distributed delay tree is used, the maximum delay required for many of the fixed delay stages is reduced, thereby reducing the number of gates required for implementation. Similarly, by varying the maximum delay applied by the variable delay stages in accordance with the position of the transducer element of the associated channel, the number of gates required to implement the variable delay stages is also reduced.

It should be understood that many alternatives are possible to the preferred embodiment described above. The widest variety of time delay devices can be used, including fixed and variable time delay devices using discrete logic devices, field programmable logic arrays or gate arrays, programmable devices, ASIC's or analog devices. Similarly, the summers described above can be implemented in many ways, including discrete logic devices, programmable logic arrays or gate arrays, programmable devices in general, ASIC's or analog devices. Also, the widest variety of smoothing filters can be used, including FIR's, IIR's as well as other digital and analog filters, of any desired smoothing characteristics.

The sampled receive signals can be analog sampled receive signals, in which case charge coupled devices may be useful in implementing the functions described above. The system described above can be modified for use with other transducers, such as linear and curved linear transducers. In this case, a de-rotation multiplexer can be placed between the transducer elements and the beamformer inputs.

As another alternative, it is not required in all embodiments that upsamplers actually insert additional sample values between the measured sample values. For example, inserted samples can be accounted for but not physically added to the data stream.

As another example, the beamformer described above can include devices for phase rotation to further enhance beamformation.

As used herein, the term "transmit event" is intended to refer to a firing of a transducer such as a phased array transducer.

The term "user selection" is intended broadly to encompass any choice by a person operating an ultrasound machine to acquire ultrasound images or measurements. For example, a user can select B-mode or color flow mode operation during an ultrasound examination as examples of a user selection.

The term "receive signal" is intended broadly to encompass analog and digital signals at any point in the signal processing path, including signals prior to beamsumming, partially-summed signals, fully beam-summed signals before or after demodulation or detection.

The term "upsample" is intended broadly to encompass methods and devices for increasing the data rate of a sampled signal by inserting one or more samples between adjacent measured samples, which inserted samples may be zero or some other value.

The term "delay" is intended broadly to encompass both delaying and advancing one signal relative to another.

The term "summer" is intended broadly to encompass both single-stage as well as multiple-stage summers, included weighted summers.

The term "signal path" is intended to encompass paths with and without branches. When two elements are said to be in a signal path, it should be understood that one or more additional, unrecited elements may be interposed between the recited elements in the signal path.

The term "set" is intended to encompass one or more.

The term "sub-aperture" is intended to encompass one or more adjacent channels i.e. channels associated with adjacent transducer elements or transducer element sets.

SCAN CONVERSION AND EMBEDDED EKG EMBODIMENTS

The scan conversion and/or embedded EKG discussed below may be used with any one or more of the various embodiments discussed herein. The scan converter 24 provides flexibility for converting data from an acoustic grid to a display format. A set of instruction codes is provided for implementing the flexibility. By changing the instruction codes, the scan conversion process changes. A single memory stores the incoming data where read and write operations are performed sequentially. The same memory may be used for storing the scan converted data. A reprogrammable logic device is preferably used to scan convert the data and is programmed differently for different modes of operation.

In one embodiment, the scan converter 24 comprises a pixel processor 1302, an incoming data RAM 1304, an instruction RAM 1306 and an outgoing data RAM 1308 shown in FIG. 13A. Preferably, the pixel processor 1302 comprises a field programmable gate array (FPGA), such as an Altera 10K50V field programmable gate array, but an ASIC, a processor or a reprogrammable logic device may be used. Volatile or non-volatile reprogrammable devices may be used. Preferably, the incoming data RAM 1304 and the outgoing data RAM 1308 each comprise a single Asynchronous SRAM, but other RAM or memory devices may be used. The instruction RAM 1306 comprises a DRAM and optionally a EDO, but other RAM or memory devices may be used. Preferably, the data width of the instruction RAM 1306 is 16 bits. Likewise, the outgoing data RAM 1308 has a data width of 16 bits to provide for a high data transfer rate. For example, the data is read at a burst rate of 50 MBytes/sec to allow time for data to be written while video is active, avoiding the need for a separate buffer to hold the data temporarily. Other data widths and bandwidths may be used. Data is stored in the outgoing data RAM 1308 in a packed format where data for each horizontal scan line is stored without spacing from data for other scan lines. Other storage formats may be used.

In one alternative embodiment, the incoming and outgoing data RAMs 1304 and 1308 comprise a single memory device. Preferably, this single memory device is accessed sequentially for both read and write functions. The memory may be large enough to incorporate at least two pages of data for ping-pong operations (i.e. writing to one page and reading from another). In yet another alternative embodiment, one or more of the incoming data RAM 1304, outgoing data RAM 1308 and instruction RAM 1306 are integrated as part of a reprogrammable logic device of the pixel processor 1302.

Preferably, a formatter 1314 provides data for processing to the scan converter 24. The formatter 1314 receives Doppler data (e.g. velocity, variance, energy, spectral Doppler and/or other motion or flow data) from the Doppler processor 20 (FIG. 1), B-mode and/or M-mode data from the RF processor 22 (FIG. 1), and EKG data from the transmit beamformer controller 12. The formatter 1314 formats the data as discussed below, interleaves the data as a function of time and type of data and regulates the rate at which EKG data is provided to the pixel processor 1302.

FIG. 13B graphically represents one preferred embodiment for the operation and structure of the scan converter 24. The scan converter 24 obtains processed scan-line data from the RF processor 22 and the Doppler processor 20 (FIG. 1). The data is transferred on an acquisition data bus 1310 to the scan converter 24. Preferably, the acquisition data bus 1310 comprises a serial synchronous data bus, but parallel or asynchronous busses or transfer methods may be used.

The transferred scan-line data is on an acoustic grid which may include a polar coordinate, a rectangular, a parallelogram or other format with a frame of data representing a region of interest along a plurality of scan lines. Each sample representing a point along one of the scan lines comprises a variable number of bits from 1 to 8, but a greater number of bits may be used.

Embedded with the scan line data are control instructions. The format of a line in one embodiment is: [line sync][line header][line data]. The line sync comprises a string of 17 ones surrounded by zero bits. The line header precedes the samples and contains three pieces of information: the scan line number, a line type, and a bits-per-sample value. The bits-per-sample field is the number of bits per data sample minus one. The scan line number indicates which scan line the data represents with the scanned region. The supported line types are listed as

| Line Type | Description |
| --- | --- |
| 0 | Null |
| 1 | 2D Structure |
| 2 | 2D Color Flow |
| 3 | M-Mode Structure |
| 4 | CW Doppler |
| 5 | EKG Data |
| 6 | Alternate 2D Structure |
| 7 | Interrogation |
| 8 | PW Doppler |

Other data formats, line type representations and organizations of the data may be used.

In the input data process 1320, the scan converter 24 translates the line types into one of four data types: time motion mode (e.g. M-mode and/or spectral Doppler mode), two-dimensional B-mode data, two dimensional Doppler or color flow data, and EKG data. A line of data representing time motion mode data is terminated in the data stream with a line terminator, such as a string of 19 ones surrounded by zero bits. Time motion mode data consists of a single line of data for any given time.

For two-dimensional data, a given time is represented by a frame of data representing a plurality of lines. Various types of data (e.g. B-mode and Doppler data) may be contained within a single frame. The frames of data preferably have the following format: [frame sync][frame header] [line1][line2] . . . [lineN][frame terminator]. Other formats and data organization may be used. The frame sync comprises a string of 18 ones surrounded by zero bits. The frame header indicates the frame number and a frame time indicating the number of milliseconds since the previous frame, each preferably comprising a byte of information. The scan converter ignores any other frame header bytes that follow the first two. The frame terminator comprises a string of 20 ones surrounded by zero bits. Using the frame and line header information, the scan converter 24 determines the scan conversion process to use.

In the input data process 1320, the pixel processor 1302 initially identifies the frame and line sync information. Once a sync is detected, header information is obtained and data is transferred to the incoming data RAM 1304. Preferably, a delay is provided by a serial shift register in the serial acquisition data bus path. The delay is at least as long as the longest sync sequence plus any zero-padding prior to the sync. Thus, a sync may mark the end of the data line without collection of extraneous samples (i.e. no sample count is provided).

Access to the incoming data RAM 1304 is arbitrated between the input data writes and any data reads conducted by a scan conversion process 1322. Using this structure, each datum is sequentially input and sequentially output for scan conversion. In alternative embodiments, groups of data are sequentially input and/or output. For example, a group of at least two samples along a scan line is output, and then another group of at least two samples along a different scan line is output. The scan conversion process 1322 determines when the write request is to be serviced. The delay in servicing the request may be large, so an 8-bit wide, 4 deep FIFO buffer preferably precedes the incoming data RAM 1304. The FIFO buffer prevents errors in the acquisition data bus 1310 due to these servicing delays. The maximum data rate is inversely proportional to the minimum number of data bits per sample, providing the desired depth of the FIFO buffer. The minimum FIFO depth is computed as follows:

ADB_FIFO_DEPTH>=MAX_LOOP_CYCLES/(MIN_DATA_BITS-2)

where the max_loop_cycles represents the maximum amount of delay in servicing write requests.

For storing the data, the lower seven bits of the incoming data RAM address is derived from the line number. In Doppler mode, an offset is subtracted from the B-mode line number and another offset is added to the Doppler line number. The line number offsets are computed from the programmed line boundaries of the scanned B-mode region and Doppler mode region. These offsets are intended to make optimal use of the RAM size by packing all structure and color lines into 126 lines. There may be a combined total of 126 color flow and structure lines. Other memory sizes may be used. Time motion and EKG lines are written to an incoming data RAM line address 127. The next upper nine address bits are mapped to the sample address for each line. The sample address starts at 0 on each new line and is incremented by one on each new sample.

Data is also removed from the incoming data RAM 1304. The incoming data RAM 1304 is ping-ponged automatically after each new line of time motion data or frame of B-mode or Doppler data is scan converted. The incoming data RAM 1304 thus preferably comprises at least two pages of the same memory. Page A is written to while Page B is read from and vice-versa. In either situation, the data is accessed and stored sequentially. Access to the pages is interleaved. In the time motion mode, a new line signal is set when a new line of data is in the buffer (i.e. when a line terminator has been detected). In the two-dimensional modes, the new_frame signal is set when a new frame of data is in the buffer (i.e. when a frame terminator has been detected). The new_frame (new_line) signal is cleared when that frame (line) is scan converted. The pixel processor 1302 waits for a new_frame (new_line) to be cleared before writing over the stored data.

For B-mode imaging, EKG data is received by the scan converter 24 in a packet similar to any other line of data. In the incoming data process 1320, EKG lines are processed like time motion lines, except that a frame terminator as well as a line terminator may terminate a line of EKG data. Time motion lines of data contain an EKG sample just after the line header while all other line types may not.

Referring to FIG. 13A, data is written into the incoming data RAM 1304 through the acquisition data bus 1310 by the pixel processor 1302. Alternatively, data may also be written into the incoming data RAM 1304 by other means, such as a reprogrammable logic device, a processor, a digital signal processor, an ASIC and/or dedicated hardware. Once a frame of data representing two-dimensions or a line of time motion data is stored in the incoming data RAM 1304, the pixel processor converts the data for display and writes the converted data into the outgoing data RAM 1308.

The scan converter 24 converts each frame of data to a form that can be displayed on the display 30 as shown by the scan conversion process 1322 of FIG. 13B. For example, the data is formatted in a Cartesian coordinate format as raster data. In one embodiment, the display format is standard 640×480 VGA at a 60 Hz frame rate, non-interlaced. The frame rate and video timing may vary, such as a function of the type of video output.

Time motion data scan conversion comprises transferring each new data line into the outgoing data RAM 1308. Since time motion data is organized along vertical lines but the video display updates along horizontal lines, the data is written into the outgoing data RAM 1308 with the address between samples incremented by the value equal to the width of the time motion display window. Preferably, the transfer of time motion data occurs in real-time (visually instantaneously), so the transfer may interrupt two-dimensional scan conversion. Generally simultaneous two dimensional and time motion processing is provided.

For scan converting data representing two dimensions, the instruction RAM 1306 stores the instructions used by the pixel processor 1302 to convert the format of the data. Using at least a dual buffer structure, the instruction RAM 1306 is ping-ponged to be updated quickly and with minimal screen disturbance.

In the scan conversion process 1322, a bilinear interpolation on the two-dimensional set of data in the incoming data RAM 1304 is performed. Other interpolation or extrapolation methods may be used. The format of the instructions in the instruction RAM 1306 preferably comprises the minimum amount of information necessary to perform the bilinear interpolation on a spatial location by spatial location basis. For each particular spatial location on the output grid, the instruction RAM 1306 stores the address of one of 4 samples in the incoming data RAM 1304 surrounding the particular spatial location as well as the fractional distances along each axis (e.g. scan line) from the one spatial location to the particular spatial location on the output grid. In one embodiment, the 3 bytes per spatial location (e.g. 2 bytes for the polar coordinate address and 1 byte for the fractional distance) are stored. The other computations for the interpolation are performed by the pixel processor 1302.

Interpolation is performed as a function of the stored information. The fractional distance from the desired spatial location to the nearest polar coordinate sample in the upper left direction comprises an error coefficient. The error coefficient preferably provides 3 bits of radial error and 5 bits of angular error. The error coefficient is fed through four 256×8 lookup tables in the pixel processor 1302 to produce 4 sample weights. The four weights are calculated as follows:

weight0=(1-rerr)*(1-terr)

weight1=rerr*(1-terr)

weight2=(1-rerr)*terr weight3=rerr*terr

The value rerr represents the fractional radial error as $\{0, \frac{1}{8}, \frac{2}{8}, \ldots, \frac{7}{8}\}$. The value terr represents the fractional angular error as $\{0, \frac{1}{32}, \frac{2}{32}, \ldots, \frac{31}{32}\}$. Other calculations and value resolutions may be used. The weights are multiplied by the four surrounding polar coordinate samples, and the results of these multiplications are summed to form the final result.

In one embodiment, the interpolation operation is performed with several pipeline stages. Preferably, each interpolation requires 4 or fewer clock cycles per spatial location to complete for one type of data, such as B-mode data. For example, scan converting Doppler data, which also includes B-mode information, may use 8 clock cycles per spatial location. In an alternative embodiment, 6 clock cycles are used where radial interpolation is changed from a modified nearest neighbor interpolation to a standard nearest neighbor interpolation as will be described later. Some clock cycles are also used for writing the incoming data as well as overhead for the instruction RAM refresh and row changes (e.g. accessing data in different rows of the memory matrix may require more cycles than accessing data in a same row).

Since color flow data (e.g., Doppler data) is acquired along the same scan lines and range position as the B-mode data, the same instruction set is used for both Doppler data and B-mode data processing. In an alternate embodiment, the data is not co-located. Interpolation for Doppler data preferably comprises a modified nearest neighbor interpolation in the radial dimension and a linear interpolation laterally on the results of the radial interpolation. Other interpolation or extrapolation methods may be used. Preferably for the modified nearest neighbor interpolation, the sample along a same scan line that is closest vertically to the output data grid is selected where the two nearest samples are non-zero. If the Cartesian coordinate location is vertically between a zero valued and a non-zero valued incoming samples, one half of the non-zero value is determined. Horizontally, the two nearest determined vertical values are linearly interpolated to the output data grid or pixel.

In one embodiment, the pixel processor 1302 is implemented, in part, as an 8×6 multiplier-accumulator (MACC). For B-mode conversion, the weight values are preferably 8 bits and the data comprises 6 bits. The result comprises 6 bits. For Doppler data, the MACC is only used for the linear interpolation performed in the lateral dimension. Prior to the MACC, the preferably 7-bit Doppler data values of the two surrounding lateral samples are subtracted to check for a magnitude difference greater than 64. If the difference is greater than 64, 128 is added to one of the two samples. The result is an 8-bit data value. The resulting data is provided to the 8-bit side of the MACC and the angular error value is fed into the 6-bit side (the actual angular error may be only 5 bits). The most significant bit of this result is discarded and a 7-bit value is produced. Other numbers of bits may be used.

Preferably, both Doppler data and B-mode data interpolation is performed in parallel. The MACC, however, is utilized serially with the Doppler data being processed first. The scan converted Doppler and B-mode data are then arbitrated. If the B-mode value is greater than a threshold level or if the absolute value of the Doppler data is less than a threshold, the B-mode value is displayed. Otherwise, the Doppler value is displayed. Also, boundaries are defined for the Doppler data outside of which all B-mode values are used. Preferably, Doppler and B-mode line boundary registers are double buffered so that registers used by the scan conversion process are updated at the start of each new frame of data.

In one embodiment, the Doppler data is filtered along horizontal video lines by the pixel processor 1302. Preferably, three levels of filtering are available, including no filtering, a low filter setting using a 3-tap filter with coefficients of 0.25, 0.5, 0.25, and a high filter setting using a 4-tap filter with coefficients of 0.25, 0.25, 0.25, 0.25. The filter preferably implements a 2-sample averaging function. Fewer or more levels of filtering and/or different types of filters and associated coefficients may be used.

EKG data is processed by the scan converter 24. EKG data represents a trace where a horizontal axis represents time and a vertical axis represents amplitude. This trace is shown with an image on the display 30 (FIG. 1). In one preferred embodiment, the EKG data is processed by the scan converter 24 with the image data, such as B-mode data.

Figure 8:
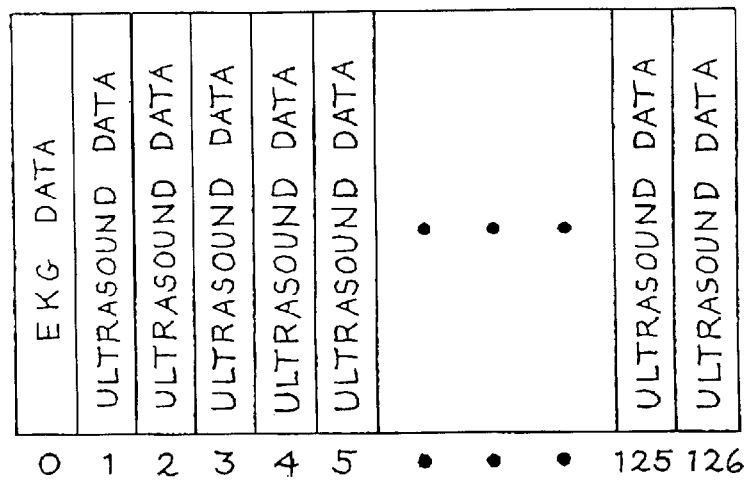
FIG. 8 is a graphical representation of a frame of data with embedded EKG data.

The EKG data is preferably linked with ultrasound data for transfer to the scan converter 24. For B-Mode imaging, at least one line of EKG data is received by the scan converter 24 as part of each frame of B-Mode data as shown in FIG. 8. More EKG lines may be received at any time either with or without a frame of B-Mode data. If additional EKG lines are received by the scan converter 24, a line terminator is provided so that the display is updated in real-time. Preferably, the EKG line of data comprises all of the samples necessary to fill the EKG display window (i.e., an entire trace). The line of EKG data represents 1 or more seconds or heart cycles, such as 2 seconds.

The scan converter 24 transfers the incoming EKG data to the outgoing data RAM 1308 like time motion data. A label bit in the scan converter control register can disable the collection of EKG lines, such as when B-mode, Doppler mode and time motion mode imaging is performed simultaneously. For time motion data, the EKG data representing the entire EKG trace is provided with every line just after the line header. Since the EKG data and the ultrasound data, such as B-mode data, are processed with each other, an accurate temporal relationship is maintained between the image and the EKG trace. Where the image frame rate is below 30 Hz or another rate, the scan converter 24 receives a EKG trace for display without a corresponding B-mode or color Doppler image from the formatter 1314. The EKG trace preferably updates with a minimum rate of 30 Hz. Thus, the trace appears to be continuous.

The outgoing data RAM controller maps the EKG data to spatial locations in an EKG display window. For every horizontal pixel location within the window, every vertical pixel that falls between the current EKG sample value and the previous sample value in the window is lit to form a line on the display. An EKG processor and formatter are responsible for sampling the EKG data so that the samples map correctly to the number of horizontal pixels within the EKG display window. The EKG data is also pre-scaled by the EKG Processor to provide the proper display height. Preferably, EKG sample values of zero are not displayed.

An EKG trigger is indicated by lighting all the vertical pixels, except trace pixels, within the EKG window with a unique color whenever a trigger is detected. In one embodiment, the trigger is indicated by bit 7 of the data being set while bit 6 is clear. Other trigger indication schemes may be used. Likewise, an EKG wiper is displayed similarly with another unique color and detected by bit 7 of the data being set with bit 6 also set. The EKG wiper is disabled by setting a bit in the scan converter control register. In real-time display of the EKG, disabling the wiper may be preferred because the wiper may appear jumpy.

The pixel processor 1302 interfaces with the outgoing data RAM 1308 using the output data process 1324. An outgoing data RAM interface coordinates reads and writes of scan converted and other data to or from the outgoing data RAM 1308. The outgoing data RAM interface comprises components in the pixel processor 1302 or the outgoing data RAM 1308. Data transfers after completion of the scan conversion process 1322 are synchronized to the video clock before the data is transferred to the outgoing data RAM 1308. Alternatively, the scan converter runs at a same clock rate as the video clock.

The outgoing data RAM interface also arbitrates between read and write functions. Preferably, two small FIFO buffers are located at the input and output of the outgoing data RAM interface to manage latencies in RAM accesses. Video data output (i.e. reads from the outgoing data RAM 1308) are assigned the highest priority to make a constant stream of video data available for display. Image data writes to the outgoing data RAM 1308 are assigned the next highest priority. An acquisition control bus 1312 accesses with the lowest priority.

In one embodiment, the outgoing data RAM interface input FIFO buffer is not large enough to manage the entire delay latency of the scan conversion process 1322. Therefore, the minimum FIFO buffer size required to avoid the need to throttle the pixel processor 1302 is selected as a function of the input and output data rates. This embodiment may limit the maximum rate at which the scan converter 24 outputs data. In alternative embodiments, a larger buffer is used or a FIFO buffer of the grab port interface 1326 is used as the output data RAM input FIFO buffer.

Data is written into the outgoing data RAM 1308 differently depending on the data type (i.e. 2D, time motion, or EKG). In the output data process 1324, a portion of outgoing data RAM 1308 is assigned to an XY boundary table. This table defines the boundaries of the XY display coordinates for each image window or type of image. X and Y display coordinates are referenced by a pair of counters. The X counter is cleared on the horizontal sync pulse and incremented on each video clock cycle while a display enable signal is active. The Y counter is cleared on the vertical sync pulse and incremented on each horizontal sync pulse following a line when a display enable signal is active.

The types of image windows comprise two-dimensional, time motion or EKG windows. One image window or a combination of two or more types of image windows are present on the display simultaneously. In one embodiment: the EKG window appears 3 pixels below any tissue motion or spectral Doppler window and is always the same width as the tissue motion or spectral Doppler window; the tissue motion, spectral Doppler and/or EKG window is either on top of or below any 2D window; and the windows do not overlap. Other window relationships may be used, including overlapping and different spatial arrangements.

Start and stop lines are defined for 2D and time motion windows. A height parameter is defined for EKG windows and a width parameter is defined for EKG and time motion windows. These parameters are read out of the outgoing data RAM 1308 during each vertical blank. Horizontal start and stop pixel locations are defined for each 2D line within the 2D window. These are read out during each horizontal blank for each active line of the 2D window.

Preferably, display disturbance is minimized while the XY boundary table is updated. The table is separated into two pages to allow overlapping read and write operations. New tables are always written into the inactive RAM page. While the scan conversion process 1322 occurs and/or a new frame of data has not yet been received, the previous table remains active. When the scan conversion of the new frame of data begins, the 2D display is removed or blanked. The 2D display reappears when the scan conversion is complete.

From a frozen or reset state, time motion windows are preferably first blanked when a new line of data is acquired and then widened gradually with the progression of incoming time motion data lines. When a full time motion window's worth of lines are written to the outgoing data RAM 1308, the window stays open until a new time motion window refresh is required, such as based on a freeze command or input from the acquisition control bus 1312.

In one embodiment, data read from the outgoing data RAM 1308 is processed through a 256×18-bit or other sized lookup table implemented in the pixel processor 1302. The lookup table contains at least one location for every supported type of data and outputs 6 bits each of red, green, and blue data for display. Inactive display pixels are assigned a background shade color. The background shade color is used where no window is opened, the screen is blanked, or for any pixels not lit inside the EKG window. The color flow color map is changed by rewriting the lookup table. The B-mode codes are used for all B-mode images and as well as portions of images as well as for displaying Spectral Doppler data. Linear or non-linear mapping with or without dynamic range compression performed at the RF or Doppler processors 22 and 20 (FIG. 1) may be provided.

In one embodiment, the scan converter 24 scan converts data for use by the CPU 52 (FIG. 3). The CPU 52 utilizes the grab port interface 1324 to obtain data. The data output from the scan converter 24 is provided directly by the acquisition control bus 1312 via the grab port interface 1312. A bit in the scan converter control register is set to enable this mode. When enabled, interpolation is performed as usual except that data flow is throttled by the grab port interface 1324. Scan converted data is written directly into a FIFO buffer located within the grab port interface 1312. When the FIFO buffer is full or substantially full, scan conversion is stopped until more memory is available. The FIFO buffer is emptied by reading from the acquisition control bus 1312. Preferably, the data is read as a block at a particular grab port address, and the block size corresponds to the number of pixels within the boundaries of a 2D sector.

The processes described herein for the scan converter 24 are controlled as a function of the instructions in the instruction RAM 1306. The instruction RAM contents instruct (e.g., program) the pixel processor 1302 how to scan convert B-mode and color flow two-dimensional data. Instruction RAM access from the acquisition control bus either has priority over scan conversion or cycle-steals from the scan conversion process 1322.

The acquisition control bus 1312 comprises an 8-bit wide asynchronous/synchronous data bus, but other busses for transferring data may be used. Data from the acquisition control bus 1312 is used to program control registers, read from and write to memory, and for capturing two dimensional interpolation results. The acquisition control bus interface is synchronous with the 29 MHz clock in one embodiment to minimize transfer time. All other system modules utilize the acquisition control bus read, write and strobe signals to perform data transfers with no free-running clock. Other clock formats may be used.

The scan converter memory map of one embodiment is shown in Table 1.

stored in the instruction RAM 1306 or elsewhere in the system 50 (FIG. 3). In alternative embodiments, the scan conversion transforms are computed dynamically by the central processing unit 52 (FIG. 3) in response to a mode change and provided to the scan converter 24.

The scan converter 24 is used for both of real-time image generation and off-line playback of images in one embodiment. During real time acquisition, acquired data is processed by the scan converter 24 for display and stored in a history (i.e. CINE) memory by the central processing unit 52 (FIG. 3) in the system RAM 58, the disk drive memory 54 or another memory for later image generation. Upon image recall, the same acquired data set is processed by the scan converter 24. The processing is the same or different as the real time scan conversion, such as using a different instruction table and associated reprogrammed pixel processor 1302. Annotation data may also be stored with the acquired

TABLE 1

DSC Memory Map

| REGISTER/RAM TABLE | MODULE | COMP ID | BASE ADDR (24 BIT HEX) | MAX SIZE (BYTES) | PRE-COMPUTED? |
|---|---|---|---|---|---|
| DSC Frame Grab Port | DSC | 1 | 200000 | N/A | N/A |
| This is a single byte-wide read-only port accessible through the ACB. Its purpose is to provide a direct data output port from the 2D interpolator to the system processor for use in converting frames of R-Theta data to X-Y format. | | | | | |
| DSC_INSTR_TABLE | DSC | 1 | 600000 | 2 × 768 K | yes |
| Scan Converter Instruction Table contains location of 4 surrounding R-Theta samples for each pixel contained within the 2D sector. This is all the information needed to perform a Bi-linear Interpolation from R-Theta data space to XY space. The RAM is ping-ponged automatically after one contiguous block transfer is completed. Also, every 4$^{th}$ byte address in the RAM is skipped automatically when reading or writing from the ACB interface. | | | | | |
| DSC_XY_BOUNDS_TAB | DSC | 1 | A00000 | 2 × 2 K | yes |
| XY Pixel Boundary Table which defines the size, shape, and location of the displayed 2D sector and the size and location of the rectangular TM window. This table is automatically ping-ponged after one contiguous block transfer is completed. | | | | | |
| VIDEO_LOOKUP_TABLE | DSC | 1 | C00000 | 512 | yes |
| This table maps the image data into RGB components for display. | | | | | |
| DSC_CONTROL_REG | DSC | 1 | 000002 | 2 | no |
| This register contains Scan Converter control bits. | | | | | |
| DSC Color Flow Interface | DSC | 1 | 000008 | See linked document. | |
| This register set contains control parameters specific to color flow operation. | | | | | |
| Display Window Control Register | DSC | 1 | 00000C | 1 | no |
| This register controls the independent blanking the 2D and Time-motion (TM) display windows. | | | | | |

During normal operation, the DSC_INSTR_TABLE and DSC_XY_BOUNDS_TAB locations are accessible through the acquisition control bus 1312. These provide table updates for scan conversion processes and XY window formats. These tables are automatically loaded into the proper instruction RAM addresses. For example, as the user selects an imaging function or a transducer array is changed, a pointer identifies the appropriate scan conversion instruction table. Alternatively, some or all of the instructions are computed in real time. At least two separate pages are used in one embodiment, one for reading and the other for writing, to minimize display disruptions during table updates.

Using the pre-defined scan conversion transforms, different transforms for different images or modes of imaging are provided. The pixel processor 1302 may be reprogrammed for different modes of operation. In this embodiment, the pixel processor 1302 preferably comprises a field programmable gate array. In one embodiment, the scan conversion transforms are computed off-line and instruction sets are data. In one embodiment during replay, the scan converter 24 is configured to use the frame timing information stored with each frame of B-mode or other data to play the images through at their originally acquired rate as opposed to the displayed rate. The images may be played in slow motion by slowing the frame rate, such as slowing by a factor of 2 or 4.

Preferably, the scan converter 24 processes data while a freeze signal (i.e. no more data acquisition) is in either state. The scan converter 24 detects when the freeze signal changes state and generates a pulse in response. This pulse is used to reset the input data process 1320 as well as some other functions.

INTEGRATED GRAPHICS CONTROLLER EMBODIMENTS

An integrated graphics controller may be used with any one or more of the various systems and methods described herein. In one preferred embodiment, a graphics controller is integrated with the central processing unit 52 of the ultrasound system 50. This integration allows for efficient control of graphics and/or CPU generated image overlays (e.g. 2D or 3D) with generated ultrasound images. An extra component, components or custom design for graphics control is avoided, resulting in a less expensive ultrasound system 50.

Figure 6:
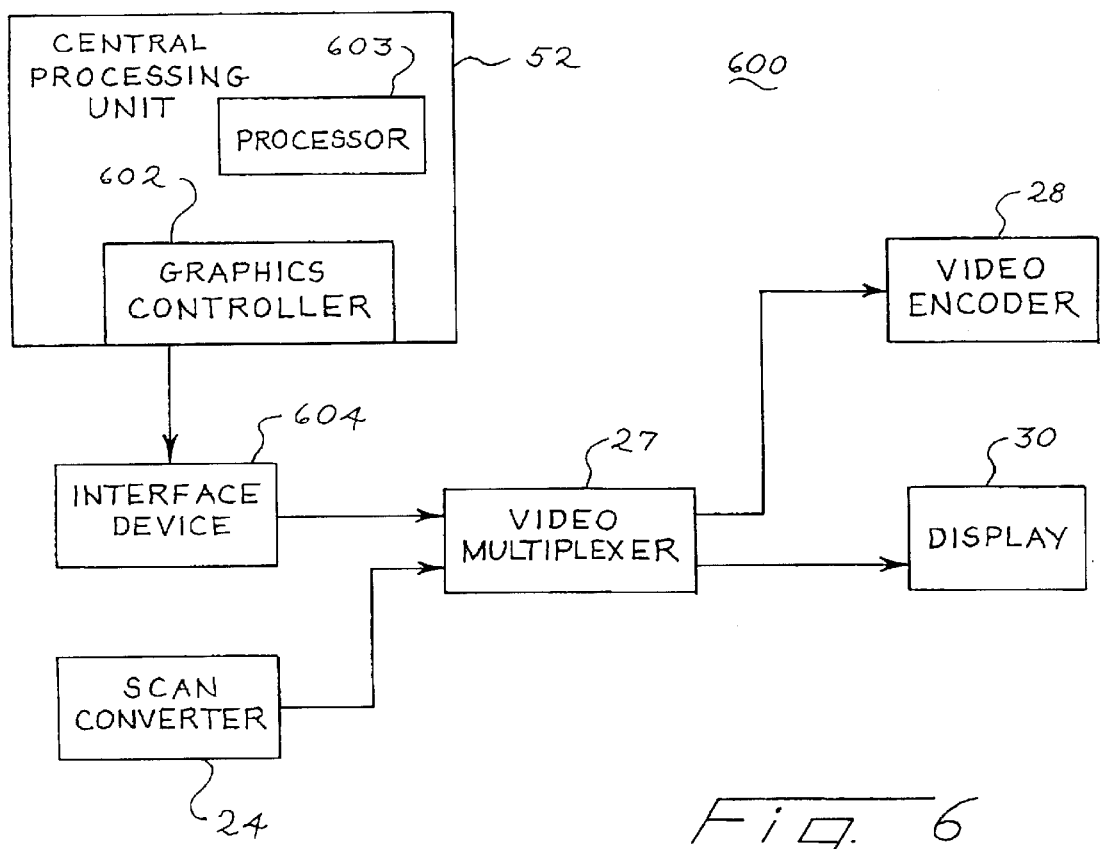
FIG. 6 is a block diagram of one preferred embodiment of a graphics control system.

FIG. 6 shows an ultrasound system 600 for generating ultrasound images. The system 600 includes the central processing unit 52, an interface device 604, the video multiplexer 27, the scan converter 24, the video encoder 28 and the display 30.

The central processing unit 52 comprises a processor 603 and the interface device 604 comprise a Cyrix Media GX chipset. Other chipsets and/or processors with or without a separate interface device known or later developed with an integrated graphics controller may be used, such as an Intel Celeron Processor with an Intel 810 chipset. The central processing unit 52 also comprises an integrated graphics controller 602. In alternative embodiments, the interface device 604 comprises the integrated graphics controller 602. The interface device 604 interfaces the central processing unit 52 with memory, busses (e.g. control data busses, ISA intefacing, and/or PCI busses), hard and floppy disk drives, data busses (e.g. ultrasound data for quantification or storage), communication interfaces (e.g. USB and/or IEEE 1394) and other components of the system.

The graphics controller 602 preferably comprises a VGA controller, but other standards for controlling two-dimensional imaging may be used, such as VESA. The graphics controller 602 may also comprise a bitBLT engine and a ROP (raster operations) unit. The graphics controller 602 generates video timing signals, two and three dimensional graphics overlays (e.g. patient annotations, icons, quantities, geometrical shapes, outlines and other graphics information used with ultrasound imaging), and/or provides three dimensional acceleration for generating an ultrasound image. Alternative embodiments may have timing signals that are generated elsewhere and input into the graphics controller 602 or input into other components. Further information about the data generated by the graphics controller 602 is provided in the subsequent section.

The graphics controller 602 outputs data from a digital output port to the interface device 604. The interface device 604 transfers the data, such as over a flat panel thin film technology (TFT) interface, to the video multiplexer 27. The video multiplexer 27 also receives data from the scan converter 24, such as B-mode, Doppler data (e.g. two-dimensional flow data), time motion data and/or EKG data. The video multiplexer 27 combines the data from the scan converter 24 with the data from the graphics controller 602. The resulting image data is provided to the display 30 for generation of an image based on the time control signals. The resulting image data is also provided to the video encoder 28 for formatting into various standard and/or proprietary formats, such as DICOM, NTSC, PAL, VGA, and/or SECAM formats.

In alternative embodiments, the data output by the scan converter 24 is provided to the graphics controller 602 on a digital input port. The graphics controller 602 performs the overlay or combination function rather than the video multiplexer 27. Digital to analog converters may be provided in the graphic controller 602 for outputting analog information.

COMPOSITE IMAGE EMBODIMENTS

For purposes of this section of the detailed description, the term "image" broadly refers to the image presented for display on a medical diagnostic ultrasound imaging system, stored on a removable storage device (such as an MO disk), and/or sent through a network coupled with the ultrasound system. An image comprises at least two image components. An image component can comprise, for example, ultrasound image data (such as a sector image), text (such as control settings and anatomical identifiers), graphics (such as depth markers and color bars), and/or measurements (such as distance, area, or volume). Image components can be displayed on separate areas of the image (such as when control settings are displayed in an area separate from the ultrasound image data) or can be overlayed on one another (such as when measurements are displayed on top of ultrasound image data).

Figure 7:
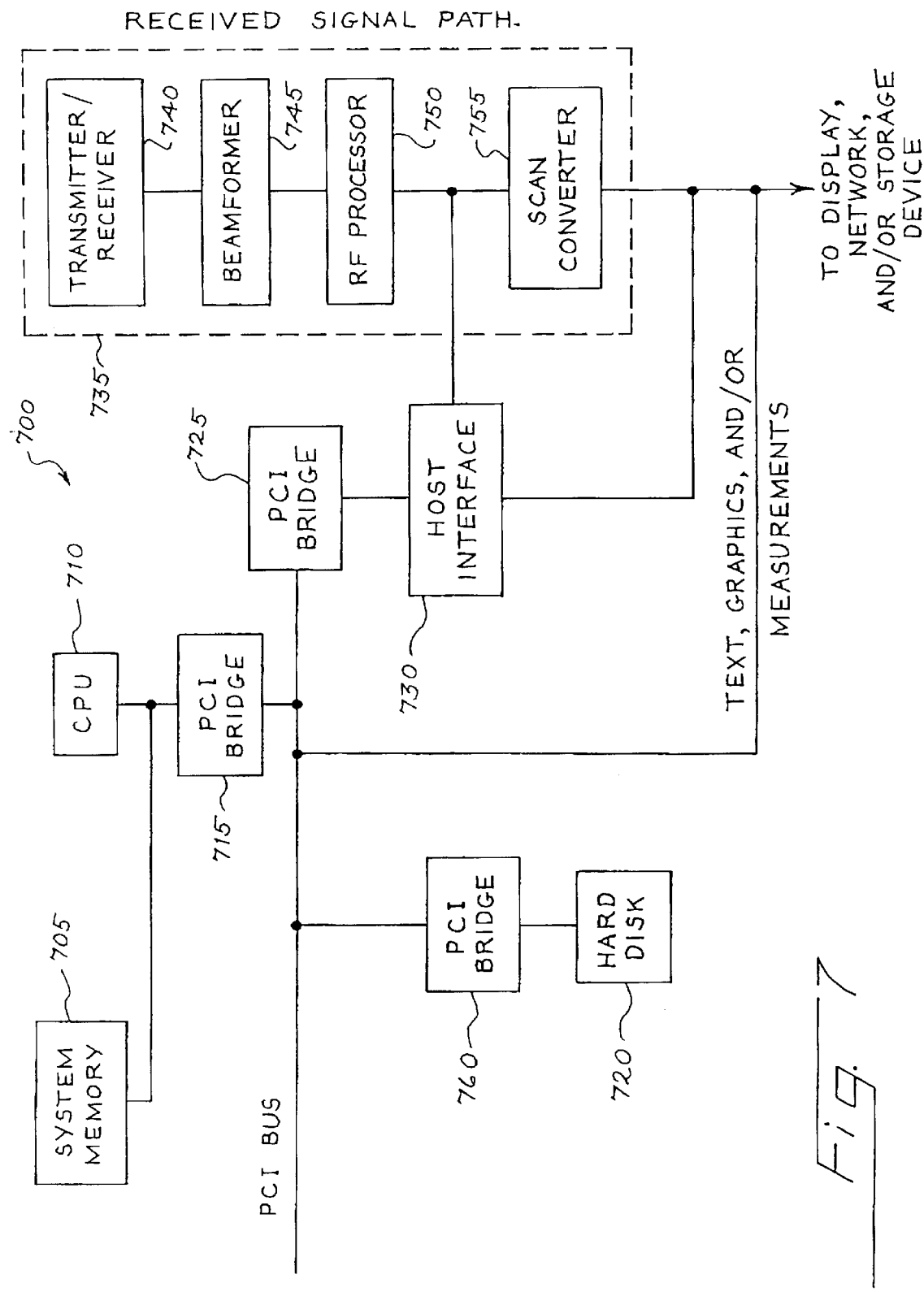
FIG. 7 is a block diagram of a medical diagnostic ultrasound imaging system of another preferred embodiment.

With reference to FIG. 7, during real-image image acquisition, the CPU 710 generates the relevant text, graphics, and measurements and adds them to the ultrasound image data after it is converted to display format by the scan converter 755. Unlike conventional ultrasound systems that use a frame grabber to provide a what-you-see-is-what-you-get implementation of saving the image, this preferred embodiment separately stores at least two image components of the image during a store operation. When image components are separately stored, they are stored in such a way that a composite image can later be constructed from one or more of the separately-saved image components. Image components can be separately stored in a plurality of databases or storage devices or in a single database or storage device.

Figure 10:
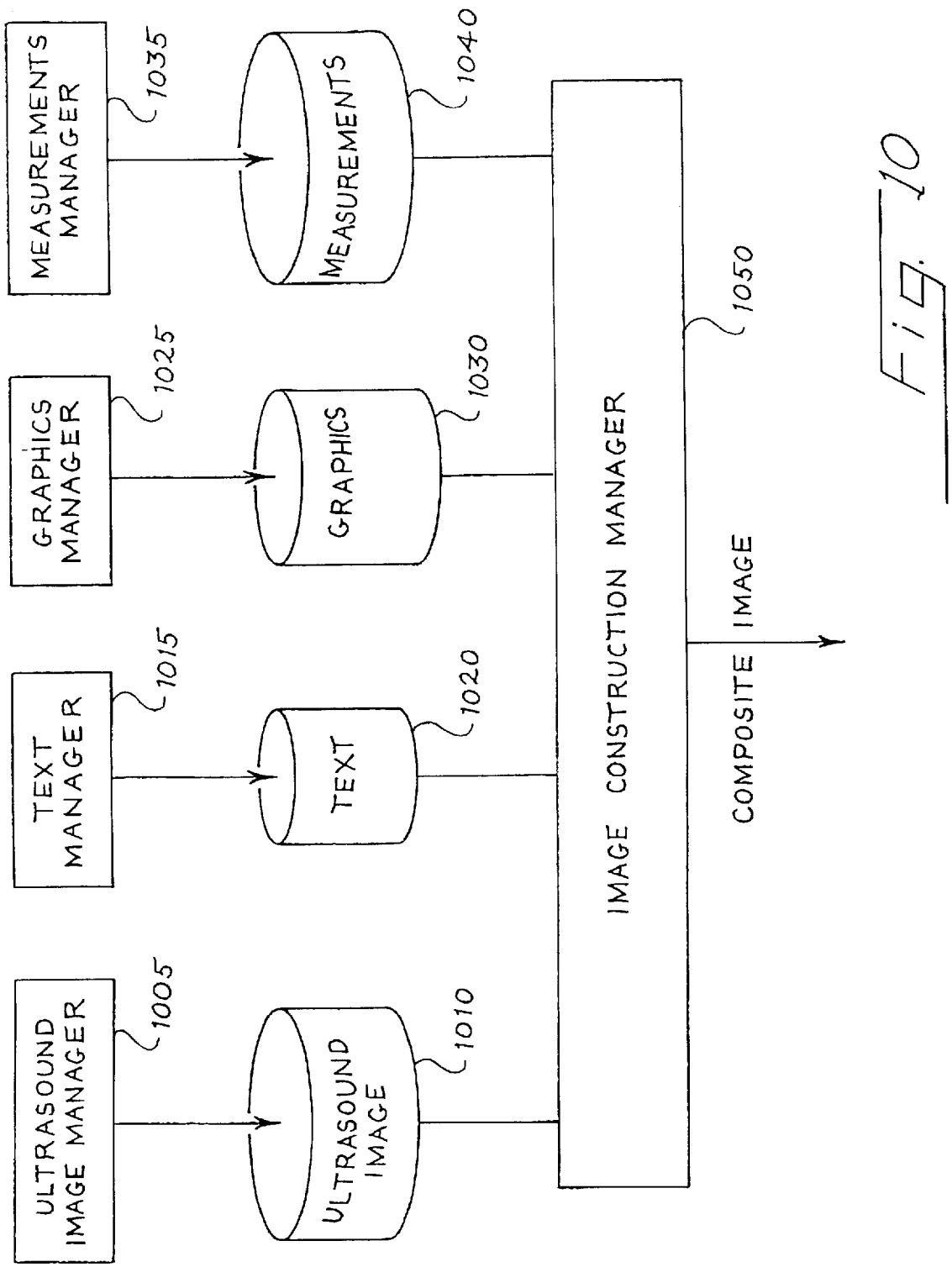
FIG. 10 is a block diagram of a medical diagnostic ultrasound imaging system of another preferred embodiment.

FIG. 10 is a block diagram showing the operation of one possible implementation of this preferred embodiment. As shown in FIG. 10, an ultrasound image manager 1405 is associated with an ultrasound image database 1010, a text manager 1015 is associated with a text database 1020, a graphics manager 1025 is associated with a graphics database 1030, and a measurements manager 1035 is associated with a measurements database 1040. Additionally, an image construction manager 1050 is coupled with each of the four databases 1010, 1020, 1030, 1040. As mentioned above, although four separate databases are shown in FIG. 10, a single database can be used to store each of the four image components.

In operation, when an image is to be saved by the ultrasound system, each of the managers 1005, 1015, 1025, 1035 is responsible for saving the appropriate image component in its associated database. For example, in this implementation, the ultrasound image manager 1005 is responsible for saving ultrasound image data in the ultrasound image database 1010. With reference to FIG. 7, in this particular implementation, the host interface 730 captures ultrasound image data (in acoustic grid data format) from the received signal path 735 after the RF processor 750 and transfers the data to the system memory 705. The CPU 710 then moves the ultrasound image data from the system memory 705 to the ultrasound image database 1410 on the hard disk 720.

Because the image components are separately stored in the ultrasound system, when a user subsequently wants to review a stored image, the user can create a composite image from some or all of the saved image components via the image construction manager 1050. For example, if a user wishes to view an image that includes ultrasound image data and text but not graphics or measurements, the image construction manager 1050 would retrieve the ultrasound image data and text components from the ultrasound image database 1010 and the text database 1020 but would not retrieve the graphics or measurements components from the graphics and measurements databases 1030, 1040. The image construction manager 1050 then creates a composite image from the ultrasound image data and text components. The composite image can then be displayed on the ultrasound system, stored on an external storage device, or placed on a network coupled with the ultrasound system, for example. With reference again to the specific implementation of FIG. 7, to perform the selective construction described above, ultrasound image data and text are retrieved from the hard disk 720 to the system memory 705. The host interface 730 then sends the image data to the scan converter 755 for conversion, and the CPU 710 sends the text data to overlay on the X-Y ultrasound image data.

This preferred embodiment offers many advantages over conventional ultrasound imaging systems. To save an image with a conventional ultrasound system, a frame grabber is used to capture pixels displayed in the image. When an image is captured, each of the image components (e.g., image data and text) of the image is captured, resulting in a what-you-see-is-what-you-get implementation of saving an image. One disadvantage associated with this approach is the limited ability to change the display of the retrieved image. In contrast to this rigid approach, this preferred embodiment allows selective construction of a composite image, thereby facilitating image presentation, image review, and post-processing functions.

Turning first to image presentation, a patient's name is typically displayed on an image. To preserve patient confidentiality, it is desired to remove the patient's name from an image when the image is shown to others, such as at a conference. With conventional systems, however, the patient's name cannot be removed since the name is integrally stored and recalled with image. With this preferred embodiment, a composite image can be formed without the patient's name, allowing the image to be shown without compromising patient confidentiality. In addition to the patient's name, it is sometimes desired to keep the system manufacture's identity anonymous. With this preferred embodiment, a composite image can be constructed without the graphics or text that identify the manufacture. Additionally, colors of the text or graphics on the constructed composite image can also be changed according to the user's preference.

This preferred embodiment also provides advantages with respect to image review. When measurements or text are placed over ultrasound image data, the measurements or text can obstruct important anatomical information on the image data. With this preferred embodiment, multiple composite images can be constructed in which one composite image contains the ultrasound image data with measurements and text overlay and the other composite image contains the ultrasound image data without any obstructions. This allows the review of two images: one with measurements and text and the other without, allowing analysis of anatomy that would otherwise be obstructed. With regard to post-processing, because ultrasound data can be recalled separately from the other image components, post-processing can be applied to the ultrasound data. Some post-processing functions that can be applied include, but are not limited to, B-Color and the changing of color maps.

NON-REAL-TIME OPERATING SYSTEM EMBODIMENTS

Turning again to the drawings, FIG. 7 is a block diagram of a medical diagnostic ultrasound imaging system 700 of another preferred embodiment. This ultrasound system 700 comprises a system memory 705, a central processing unit ("CPU") 710, a first PCI bridge 715, a hard disk 720, a second PCI bridge 725, a third PCI bridge 760, and a host interface 730. In this system 700, the system memory 705 can be used as a temporary storage device and the hard disk 720 can be used as a permanent storage device. The ultrasound system 700 also comprises a received signal path 735 comprising a transmitter/receiver 740, a beamformer 745, an RF processor 750, and a scan converter 755. Although the ultrasound system can contain additional components, for simplicity, these additional components are not shown in FIG. 7. For example, the transmitter/receiver 740 is preferably coupled with a phased-array ultrasound transducer.

As shown in FIG. 7, the CPU 710 of this preferred embodiment is not in the received signal path 735 but is used to control components of the ultrasound system 700. Because the CPU 710 is not required to operate in a real-time manner in this role, the CPU 710 can use a non-real-time operating system. As used herein, the term "non-real-time operating system" is intended to broadly refer to any non-deterministic operating system characterized by a non-predictable response time. It is preferred that the non-real-time operating system be Windows NT Workstation 4.0, Service Pack 5.0, by Microsoft Corporation. It should be noted that other non-real-time operating systems can be used such as, for example, Windows NTE, Windows CE, Windows 95/98, Linux, and Unix. It is also preferred that Visual Studio 6.0 by Microsoft Corporation be used as a development environment.

In one presently preferred embodiment, the CPU 710 uses a non-real-time operating system to transfer image data. The following three examples illustrate the operation of this preferred embodiment. In the first example, the non-real-time operating system is used to transfer image data from the hard disk 720 to the system memory 705. In operation, the CPU 710, via the first and third PCI bridges 715, 760, transfers image data stored on the hard disk 720 to the system memory 705. The CPU 710 then sends the image data from the system memory 705 to the host interface 730 via the first and second PCI bridges 715, 725. In this preferred embodiment, image data is stored in the hard disk 720 in acoustic grid format. To convert the image data for display, the host interface 730 sends the image data to the scan converter 755, and the display data is then displayed on a display device. Of course, if the image data is stored in the hard disk 720 in display format, the host interface 730 can transfer the image data downstream from the scan converter 755.

In another example, the non-real-time operating system is used to store, to the hard disk 720, image data taken from the received signal path 735 after the RF processor 750 but before the scan converter 755. The image data taken at this point in the path is in an acoustic grid format. It should be noted that image data can be transferred from other points in the received signal path 735. For example, image data in a display format can be transferred from a point in the signal path downstream from the scan converter 755.

To store image data to the hard disk 720, the CPU 710 first commands the host interface 730 to capture the image data going to the scan converter 755 and transfer the data to the system memory 705 via the first and second PCI bridges 715, 725. The CPU 710 then moves the image data from the system memory 705 to the hard disk 720 via the first and third PCI bridges 715, 760. In this preferred embodiment, the system memory 705 is large enough to hold more than one frame of image data. As a result, the CPU 710 is not required to move image data from the system memory 705 at the same rate as image data being transferred from the received signal path 735. This allows a plurality of frames of ultrasound image data to be stored in the system memory 705 before the CPU 710 needs to transfer the image data out of the system memory 705 and onto the hard disk 720. Because the response time of the CPU 710 does not need to be predictable, the non-real-time operating system can be used. This provides the advantage of not expending CPU 710 resources for each frame for image data transfer functions. In contrast, a single frame memory requires a real-time operating system since a predictable response time is needed to insure the CPU transfers image data out of the memory on a frame-by-frame basis (i.e., at the same rate as the acquisition rate) to prevent image data from being overwritten.

To prevent image data that has not been transferred from the system memory 705 to the hard disk 720 from being overwritten by incoming image data, it is preferred that the non-real-time operating system transfer data out of the system memory 705 at a faster rate than the rate at which the system memory 705 will reach capacity. Alternatively, the system 700 can be designed such that image data from the received signal path 735 will be suspended, thereby preventing incoming image data from overwriting image data that has not yet been transferred out of the system memory 705.

In yet another example, the non-real time operating system can be used to scroll image data through the scan converter 755 to view a loop of image data during acquisition. In operation, the CPU 710 commands the host interface 730 to capture the image data going to the scan converter 755 and transfer the data to the system memory 705 via the first and second PCI bridges 715, 725. After a certain amount of image data has been stored, preferably two-seconds-worth of image data, the CPU 710 transfers, via the first and second PCI bridges 715, 725, the image data back to the host interface 730. The host interface 730 then provides the image data to the scan converter 755 for conversion and subsequent display. As noted above, image data can be transferred in display format instead of acoustic grid format.

This preferred embodiment finds particular utility in portable medical diagnostic imaging systems, specifically those that weigh less than 40 pounds and/or those in which many essential real-time functions are implemented in hardware. It also finds particular utility in systems with at least 32 electrical channels (and, in particular, with at least 64 electrical channels) and in systems using a plurality of reprogrammable logic devices.

PATIENT STUDY EMBODIMENTS

With any of the preferred embodiments described herein, the ultrasound system can be used to select and display an ultrasound patient study. As used herein, the term "patient study" refers to ultrasound image data associated with a patient who has undergone an ultrasound examination. In addition to ultrasound image data, a patient study can include information relating to the ultrasound image data, the patient, and/or the examination. For example, a patient study can comprise ultrasound image data, audio annotation, text annotation, patient-specific data (e.g., name, birth date, patient id, sex, weight, height), measurement values, calculation results, hardware configuration information, software configuration information, screen formatting information, imaging protocol, and/or study date and time, for example.

Figure 9:
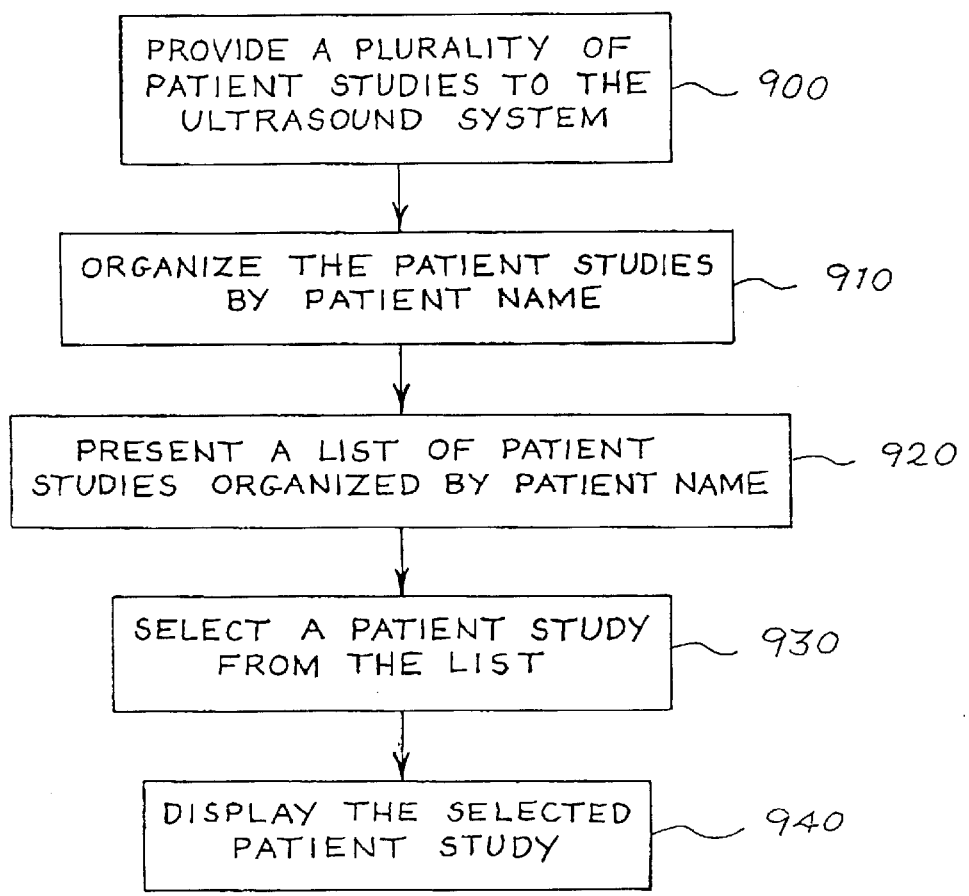
FIG. 9 is a flow chart of a method of a preferred embodiment for selecting and displaying a patient study on a medical diagnostic ultrasound imaging system.

FIG. 9 is a flow chart of a preferred method for selecting and displaying a patient study on the ultrasound system. First, a plurality of patient studies are provided to the ultrasound system (block 900). Patient studies can be provided to the ultrasound system by retrieving the studies from a network coupled with the ultrasound system, by retrieving the studies from a removable storage medium coupled with the ultrasound system, and/or by generating the patient studies with the ultrasound system.

Next, the ultrasound system organizes the patient studies by patient name (block 910). Then, the ultrasound system presents a list of the patient studies organized by patient name (block 920). The ultrasound system can present all or part of the list on a display device, on hard copy, via a speaker, or via any other medium to communicate the list to a user of the ultrasound system. The user then selects a patient study from this list (block 930). For example, a user can manipulate a user interface (e.g., a key on a keyboard, a mouse, a trackball, a touchpad, a microphone, etc.) to select one of the studies from the list. Finally, the ultrasound system displays the selected patient study to the user (block 940). It should be noted that "displaying the selecting patient study" not only refers to displaying the entire patient study but also can include displaying only a portion of the entire patient study. For example, in a patient study that contains ultrasound image data and other data (such as patient or study information), the ultrasound image data associated with that study can be displayed with or without the other data.

These preferred embodiments provide several advantages over conventional ultrasound imaging system that present an unorganized list of patient studies to a user for selection. For example, because the patient studies are organized by patient name, a user of the ultrasound system can quickly and easily identify studies associated with a particular patient. In contrast, with conventional ultrasound systems, a user is required to retrieve and view all of the listed studies to determine which of the studies is associated with a particular patient.

PORTABILITY EMBODIMENTS

In another preferred embodiment, a portable ultrasound system is provided. Larger systems, including larger systems integrated with wheels or carts, or systems too bulky to be easily moved by a single person, would not be considered portable in that, while they can be moved from location to location, their weight and/or size would make such moves difficult.

In many applications, a single ultrasound system may be shared among several clinicians in the same office, hospital or other diagnostic location. In other applications, the ultrasound system may be shared among several clinical locations, such as by several clinics. These machines may be transported from location to location by the clinicians, often with no help from other people. Still in other applications, the examination room may have limited space for medical equipment such as in rural hospitals or emergency rooms which may have to use the same room for many different functions. In these and other applications, it is advantageous to have an ultrasound system which has a low weight and a small footprint. Such systems should be capable of being carried, often along with other equipment and supplies, from location to location by a single person. Systems which require wheels or carts to transport can be inconvenient. For example, it is often difficult to roll these systems over pavement in order to load them in a vehicle. In addition, the larger weight of such systems can make them difficult to lift by a sole clinician.

In at least some of these applications, it is preferred that the functionality of the ultrasound system is not sacrificed in lieu of portability. Further, it is well known that portability places its own demands upon the system design. For example, the system is preferably rugged enough to withstand being moved from place to place on a regular basis. The system is preferably capable of handling minor bumps and shocks without breaking. In addition, such portable systems preferably provide an integrated carrying handle of the type with an opening for a hand to grip, a full size display and an integrated keyboard/input device. These concerns provide that the design of the system is based on both engineering as well as ergonomic requirements.

In the presently preferred embodiments, the ultrasound system is designed to be carried by a single person. Portable systems preferably weigh less than 30 pounds and provide a carrying handle of the type with an opening for a hand to grip. Systems which weigh more than 30 pounds may be difficult to move from location to location by a sole person, especially if the system may be transported in an automobile or if that person may carry additional equipment or supplies. The preferred ultrasound system is light weight and weighs approximately 5, 10, 15, 20 or 25 pounds although, as noted, any weight under 30 pounds may be used. Preferably the system weighs approximately 20 pounds.

Figure 11:
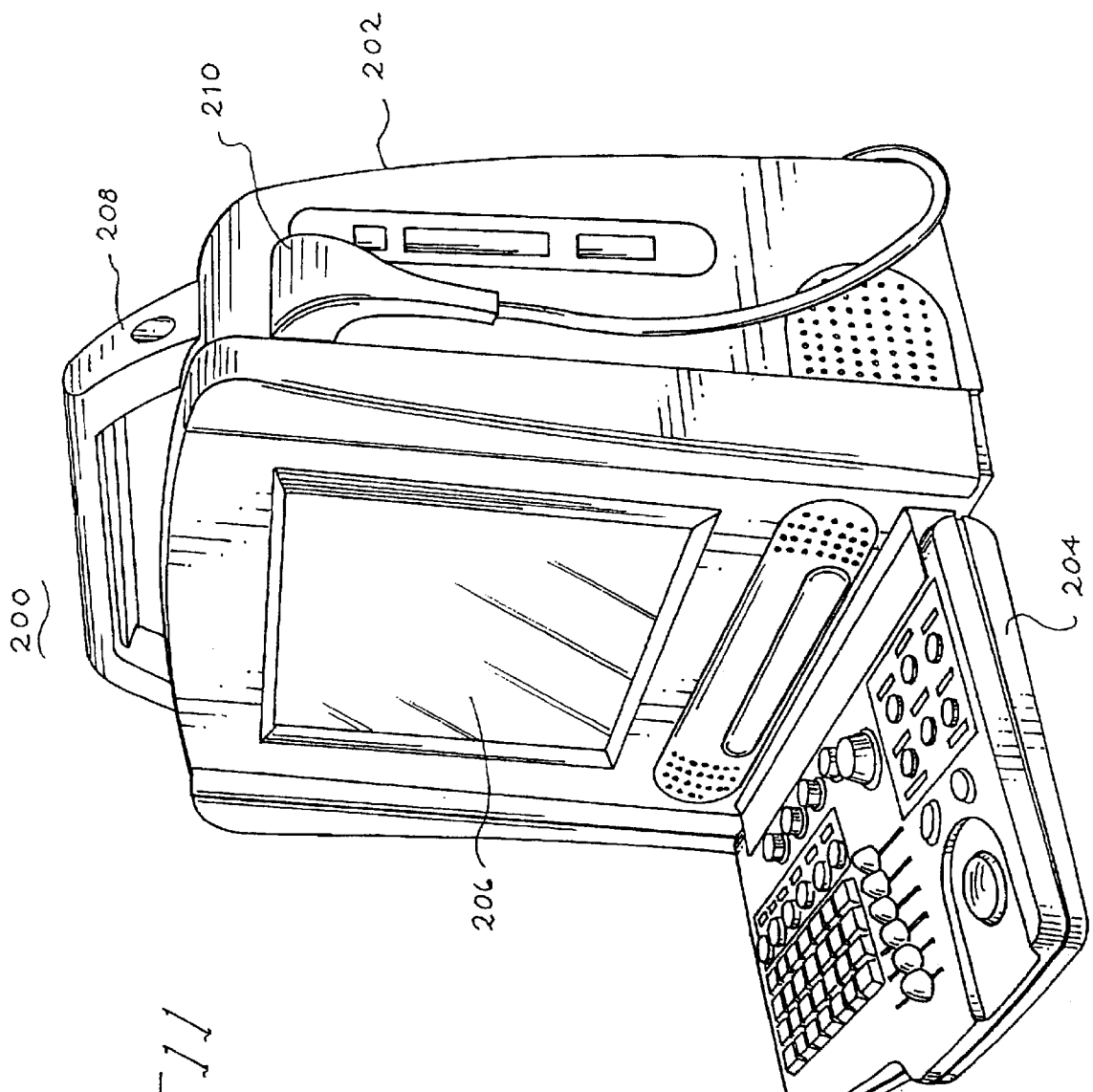
FIG. 11 is perspective view of a preferred embodiment portable ultrasound system.

Referring to the figures and in particular, FIG. 11, there is shown a perspective view of one preferred portable ultrasound system 200. This system includes a main unit 202 which further includes a hinged integrated keyboard/input device 204, a display 206 and an integrated carrying handle 208. The handle 208 is of a type with an opening that allows the person carrying the unit to grip their hand around. Further the system includes a transducer probe 210. The keyboard 204 retracts for storage and transport and deploys for use by the operator. In the retracted position, the keyboard 204 further acts to protect the display by covering the display to prevent damage. Further, in the retracted position, the keyboard 204 is itself protected from damage by facing inward towards the system when folded up/retracted. Further, such systems preferably occupy less than 1 cubic foot of space. The dimensions of the presently preferred embodiment are approximately fifteen inches wide by thirteen inches high by seven inches deep occupying 0.8 cubic feet of space. Of course, numerous combinations of physical dimensions and weight which can be used and combined to create a light and easily managed portable unit. All combinations which result in an easily carried portable ultrasound system are contemplated.

While the dimensions of the presently preferred embodiments are small, functionality is not sacrificed. The presently preferred embodiments provide at least 32 channels between the transducer and the system unit and may provide 64 channels. For the purposes of this specification a channel comprises a connection which receives data from a transducer element which the system is capable of independently delaying before summation with other elements. Providing multiple independent delays of data from a single element before summation in order to provide multiple parallel beams does not consist of multiple channels. As well, receiving data from multiple elements and summing that data before any independent time delay is applied does not consist of multiple channels.

Further, the presently preferred embodiments are capable of fundamental and harmonic B-mode imaging as well as Color Velocity (encoding the velocity of targets in motion) and Color Power (encoding the power of targets in motion) imaging and Spectral Doppler (including both PW and CW modes). The system provides a 10.4 inch display for high resolution and easy viewing as well as an integrated keyboard which hinges from a retracted position, for storage and transport, to a deployed position for use. The display provides 640×480 resolution with 262, 144 colors. In the preferred embodiment, the display is a TFT active matrix flat panel display.

In addition, the presently preferred embodiments can be used with a variety of transducer probes which utilize various transducer arrays including sector and wide view arrays. The ultrasound system can also be used with probes with other types of arrays such as linear, phased linear and curved linear arrays. Such transducer probes provide greater imaging capabilities, such as through electrically directional scanning of a region, and are preferred over other types of transducer probes such as annular transducers which are more difficult to use. It will be further appreciated by those skilled in the art that all implementations of portable ultrasound systems which retain some or all of the full ultrasound functionality of larger systems, including now or later developed functionality, are contemplated. Application specific ultrasound systems capable of limited application may also be made as a portable system while retaining the capabilities to perform specific applications.

CIRCUIT BOARD INTERCONNECTION EMBODIMENTS

As noted above, not only is the weight of the system an issue in making a system portable but also the physical size of the system. Large, wheeled ultrasound systems can be bulky and difficult to move, transport and store. Further, where space in the examination room is at a premium, it may be very advantageous to have a compact ultrasound system.

Typically, the circuit boards of an ultrasound system are arranged in a modular fashion utilizing a backplane or a motherboard. In this arrangement, the circuitry which makes up the ultrasound system is located on multiple cards which are then plugged into a common board or backplane (also known as a motherboard). This arrangement is not compact. Communications from board to board pass through the backplane, resulting in increased signal path lengths and additional board to board connectors. For digital signals, additional board to board interconnections, among other problems, create impedance matching difficulties, and for analog signals, board to board interconnections introduce electrical noise.

In the presently preferred embodiments, the circuitry of the ultrasound system is distributed over several circuit boards without utilizing a common interconnecting board, backplane or motherboard. The circuit boards are connected directly to one another in a vertically stacked arrangement such that the boards are oriented parallel to each other.

Figure 2:
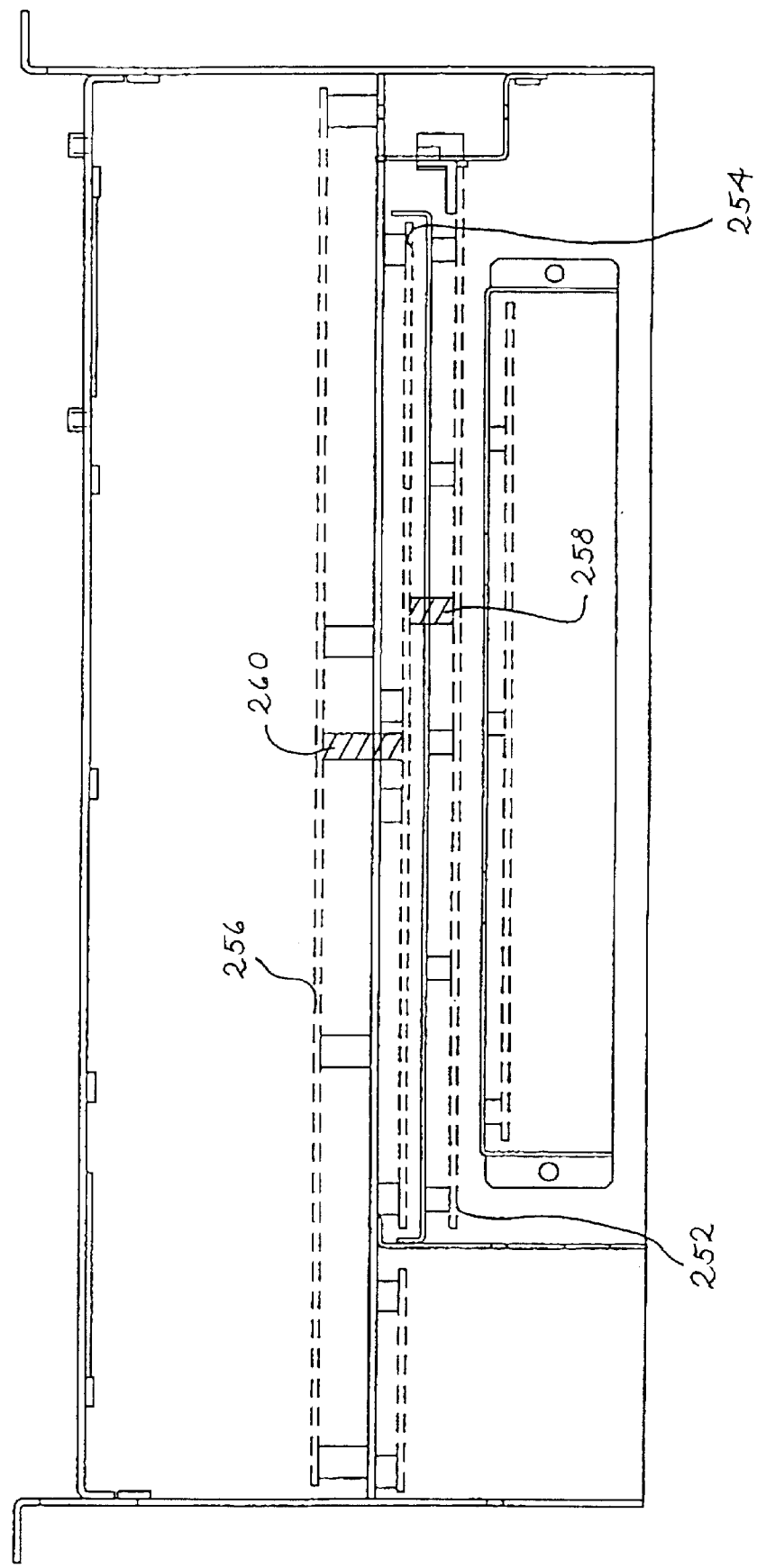
FIG. 2 is a schematic top view of a preferred embodiment depicting the circuit boards and their interconnection.

FIG. 2, shows a schematic top view of a preferred embodiment of the arrangement and interconnection of the circuit boards. The preferred embodiment includes a transmit/receive circuit board 252, a beamformer circuit board 254 and a signal processing board 256. The circuitry of an ultrasound system may be partitioned in numerous ways among the boards 252, 254 and 256. Systems with more or fewer circuit boards may be used. Boards which connect to each other have mating connectors 258 and 260 on the face of the board. The transmit/receive board 252 connects directly to the beamformer board 254 via the connectors 258. The beamformer board 254 connects directly to the signal processing board 256 via connectors 260. In systems with more or fewer circuit boards, the arrangement of boards may be different but are preferably stacked on one another to achieve interconnection. The interconnections comprise fixed pin/receptacle connectors, ribbon cables, or other forms of electrical interconnects, and/or optical interconnects. When connected, the circuit boards 252, 254 and 256 are preferably oriented parallel to each other although with other types of connectors, the boards could be arranged in any orientation. Fewer connectors may be needed and an extra common interconnecting board may be avoided. This arrangement is more compact and requires less volume than a backplane implementation where the circuit boards extend perpendicular to the interconnecting board. Fewer interconnections allows shorter signal paths to enhance timing and signal speed. Reliability is also improved because there are fewer components and fewer mechanical connections between boards. In some applications, a backplane interconnecting board is used to route signals from one circuit board to another. In this arrangement, a signal path then comprises at least two board to board transitions as the signal moves from the first board through a board to board connector to the backplane, through the backplane and through another board to board connector to the second board. By directly connecting the circuit boards together without the backplane, there is only one board to board connector in the signal path.

Directly connecting boards to one another allows for a more flexible design since the connector may be placed at any location on the board. A backplane implementation requires that the board to board connectors be mounted on the edge of the board. This necessitates routing all of the board to board signals to the edge of the board. By placing the connector anywhere on the face of the board, signal routing can be easier to implement and optimize. For example, analog input and output signals can be spaced apart to prevent electrical interference between them.

Vertically stacked/parallel oriented circuit boards dissipate heat efficiently. A heat sink is placed between boards such that when two boards are interconnected, their components contact the heat sink to dissipate heat. In the case of the preferred embodiments, the electromagnetic shielding (as described below) placed between the boards also functions to dissipate heat. Thermal pads may be disposed on the components of the circuit boards such that when the boards are interconnected, the pads contact the shield and conduct heat from the component to the shield.

ELECTRICAL SHIELDING EMBODIMENTS

In one particular embodiment of the ultrasound system, internal circuit components are shielded from electromagnetic interference ("EMI"). This EMI shielding can be implemented in a compartmentalized fashion which isolates noisy components. In addition, the shielding can provide structural integrity and heat dissipating capability.

FIGS. 4A–4G show schematic and perspective views of the shielding of the one presently preferred embodiment. Referring to FIGS. 4A–4G, in this preferred embodiment a metal support structure 402 shields the components. The structure 402 is preferably fabricated from aluminum sheet metal, although other types of materials which provide EMI shielding and/or structural rigidity may be used. The support structure 402 forms one or more, such as four, main compartments into which the various components of the ultrasound system 400 are located. The first compartment 404 contains the system power supply 406. The power supply 406 is mounted to a slide out sheet metal frame 408 which closes off the compartment 404 and allows manufacture, removal and repair of the power supply 406. A second compartment 410 is provided for the input/output ("I/O") circuit board 420. This compartment 410 isolates the boards so that electromagnetic interference ("EMI") neither escapes from the ultrasound system nor enters the ultrasound system through the I/O connections.

The support structure 402 provides two compartments 414, 416 separated by the center plate (or "firewall") 418 of the support structure 400. The center plate 418 isolates some analog components of the ultrasound system 400 from digital components. The analog compartment 414 is further subdivided into three compartments. The beamformer board 422 is mounted against the center plate 418. The beamformer board 422 is connected to the signal processing board 432 located in the front compartment 416 using board to board connections which pass through holes in the center plate 418. A metal beamformer shield 440 is positioned over the beamformer board forming another chamber 424 against the center plate 418 to isolate this component. The transmit/receive board 430 is mounted to this metal shield 440 and interconnected via board to board interconnects to the beamformer board 422 through holes provided in the beamformer shield 440. A high voltage power supply board 426 is mounted behind the transmit receive board 430 and then enclosed within another metal shield 442 to create a third chamber 428 which isolates the high voltage power supply board from the transmit receive board 430.

The support structure 402 forms a sixth chamber which contains the signal processing board 432 and hard disk. The support structure 402 is then covered by front and rear outer covers which complete each compartment and form a Faraday Cage which prevents EMI leakage. FIGS. 4C–4G show different views of the support structure 402, power supply chamber 404, I/O board 420, and I/O board chamber 410, beamformer board 422, beamformer board chamber 424, high voltage power supply board 426 and high voltage power supply chamber 428, transmit/receive board 430, transmit/receive chamber 414, signal processing board 432 and signal processing board chamber 416. The distribution and design of the various components may dictate which components are shielded from one another. Other shielding/compartmentalization arrangements may be used with more or fewer compartments.

In addition to providing EMI shielding, the shielding structure 402 forms a chassis which supports the infrastructure for the ultrasound system 400. This support structure 402 or chassis provides an internal framework to which all of the components are mounted. In addition, the support structure 402 carries the weight of the device and is integrated with a carrying handle to maintain structural integrity when the system 400 is lifted and moved. The outer plastic shell (not shown) of the device provides some or no structural support. The outer shell may be purely decorative in nature. The support structure 402 may be decorative and replace the outer shell.

In addition to its EMI shielding and structural support, the support structure 402 dissipates heat generated by the internal components of the ultrasound system 400. The circuit boards are mounted in parallel and in close proximity to the shield support structure 402. Various components which generate heat may be fitted with thermally conductive pads to conduct heat to the support structure 402. Heat is dissipated from the support structure by various methods including convection and conduction. The support structure 402 provides a large surface area over which heat can be distributed and dissipated efficiently.

TRANSDUCER CONNECTOR EMBODIMENTS

In one particular embodiment, the ultrasound system is connected with different types of transducers. Transducers may be frequently changed. The transducer is disconnected to ease movement or storage and to prevent breakage of the transducer. The transducer connector should provide the user with a sense of a solid connection. The size is such that it can be easily manipulated when being connected and disconnected. As the number of transducer channels and associated connections increases, it is important that neither the ergonomic nor electrical requirements of the connector is sacrificed.

FIGS. 4H–4K show an exemplary transducer connector 450. The connector 450 includes a housing 452, an I/O cable 454, a circuit board 456 and a plug electrical connector 458. The plug electrical connector 458 mates with a matching receptacle connector on the system unit. The housing 452 encloses the other components and provides for electromagnetic shielding which isolates the connector wiring from EMI. In the preferred embodiment, the housing 452 is constructed from a 2 piece aluminum clamshell housing 460 and 462. The housing 452 can be manufactured in many ways known in the art including die casting using the same or different materials.

The connector 450 also includes an I/O cable 454 which connects to the transducer (not shown). The I/O cable 454 connects to the circuit board 456. The circuit board 456 provides the termination and connection with the plug portion of the electrical connector 458. The exemplary connector 450 is small in size but provides a high density of signal connections. In addition, the connector preferably does not use a zero-insertion force socket. In the exemplary connector 450, the plug signal pins contact the receptacle contacts immediately upon insertion. This has the effect of cleaning the area of contact every time a connection or disconnection is made. Wear and tear of the pins is negated by increasing the plating thickness on the pins and contacts.

In the preferred embodiment, the electrical connector is preferably the Micropax™ High-Density Board-to-Board System, plated with 60 GXT™ plating, manufactured by Berg Electronics, located in St. Louis, Mo. and available as part numbers 90794-403 (plug 458 system side), 90793-401 (receptacle probe side). This connector provides 60 microinches of plating to increase the number of connection and disconnection cycles. Further, this connector provides for 160 pins at a 0.025 inch contact pitch yielding 30 contacts per cubic inch per mated connector pair. In addition, where the connector is mounted to the circuit boards, the termination density is preferably approximately 130 contacts per square inch. In the preferred connector 450, this results in approximately 10 contacts per cubic inch per assembled connector mated pair, although lower contact densities such as 5 contacts per cubic inch may be useful. Further this connector is rated at 10,000 connection/disconnection cycles. Other connectors with the same or different characteristics may be used. Referring to FIG. 4J there is shown the pin configuration for the preferred embodiment transducer connector 450.

In addition, in the preferred embodiment, the circuit board 456 in the connector 450 also provides a location to mount other probe specific circuitry in addition to the cable termination circuits such as tuning inductors, ID EPROM, temperature sensing circuitry, element multiplexing circuitry, motor drive circuitry and transducer position circuitry. It will be appreciated that other probe specific circuitry may also be located in the probe connector 450.

IMPROVED DOPPLER PERFORMANCE EMBODIMENTS

Figure 14:
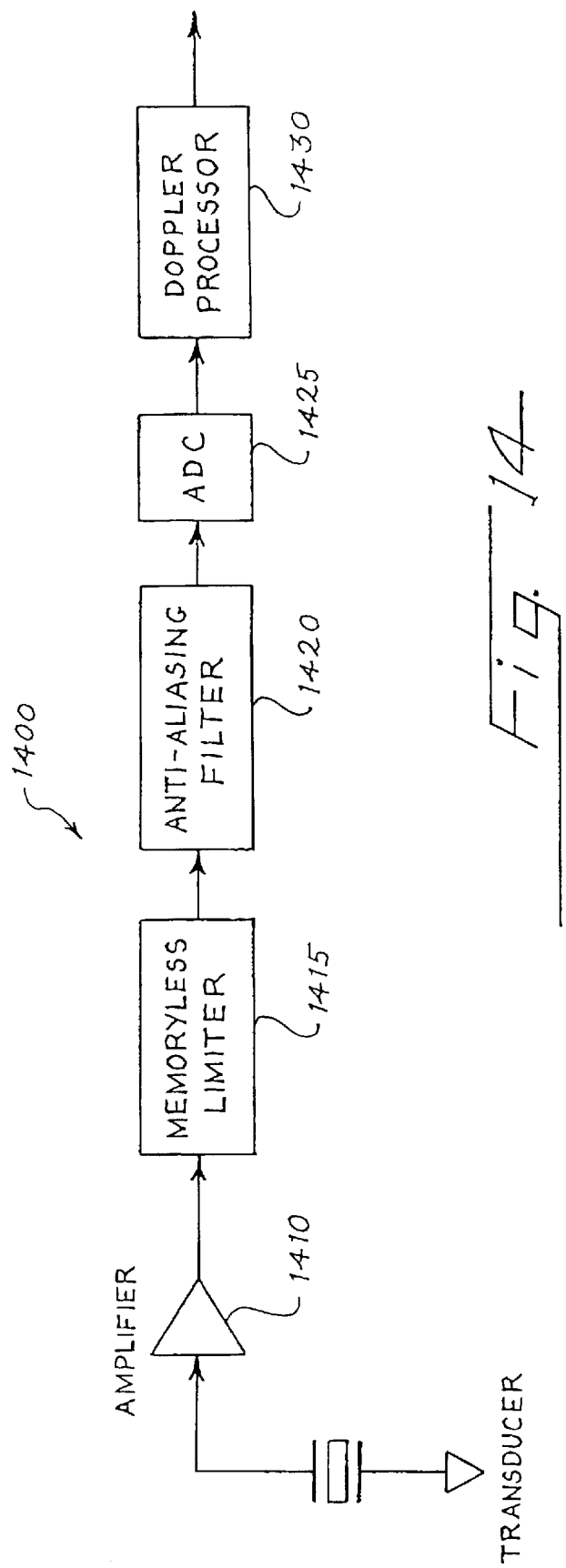
FIG. 14 is a block diagram of a receiver channel of an ultrasound system digital beamformer of another preferred embodiment.

Turning again to the drawings, FIG. 14 is a block diagram of a receiver channel 1400 of an ultrasound system digital beamformer of another presently preferred embodiment. As shown in FIG. 14, the receiver channel 1400 comprises an amplifier 1410, a memoryless limiter 1415, an anti-aliasing filter 1420, an analog-to-digital converter (ADC) 1425, and a Doppler processor 1430 (e.g., color and/or spectral). The amplifier 1410 can be a variable gain amplifier, the gain of which can be varied as a function of time, which corresponds to the depth of a reflecting object. The anti-aliasing filter 1420 can be a lowpass filter which bandlimits the signal applied to the ADC 1425 to keep the highest frequency component of the signal less than one-half the ADC sampling rate (to meet the Nyquist criterion).

In this preferred embodiment, the memoryless limiter 1415 between the amplifier 1410 and the anti-aliasing filter 1420 limits its output signal amplitude to a precise, predetermined value and has a signal delay that is independent of the amount of input overdrive. That is, the signal delay is independent of the amount of clipping. The signal zero-crossing information is preserved in passing through the precision, memoryless limiter 1415.

The maximum output amplitude of the limiter 1415 is preferably designed for a predetermined value, which ensures that the input amplitude applied to the ADC 1425 will not exceed a predetermined optimum value. The predetermined value can be programmable. This ensures that the ADC 1425 itself will not cause a loss of zero-crossing information. The amplitude limiting occurs in the precision, memoryless limiter 1415. When the limiter output clips, its output waveform approaches a square wave. The anti-aliasing filter 1420 removes the harmonics of the square wave. The waveform out of the filter is sinusoidal and bandlimited in frequency. So long as the spectrum of the signal out of the filter is bandpassed to meet the ADC Nyquist criterion, the signal can be reconstructed from the digitized samples. The limiter prevents the signal driving the ADC from reaching a level that would cause clipping in the ADC. The limiter preserves the zero-crossing information. The anti-aliasing filter bandlimits the signal so that the ADC is presented with an essentially sinusoidal signal.

It is preferred that the anti-aliasing filter 1420 bandlimit the signal sufficiently to meet the Nyquist criterion for the ADC sampling rate. Thus, in an alternate embodiment, so long as the Nyquist criterion is met, it is possible to allow harmonic content in the signal applied to the ADC 1425 and to do further filtering on the digital data after conversion. In such an embodiment, the filtering is implemented partly in the analog anti-aliasing filter before the ADC, and partly in the digital domain after the ADC where it can be included as part of the Doppler processor 1430.

This preferred embodiment provides the advantage of overcoming the problem of clipping at the input to an ADC when large amplitude signals are present. The memoryless limiter before the anti-aliasing filter ensures that the ADC does not clip. and that anti-aliasing filter bandlimits the input to the ADC sufficiently that the ADC sample rate is adequate to get samples that preserve the zero-crossing information in the A–D conversion. Thus, estimated Doppler information is preserved when a strong signal clips someplace in the signal path before the ADC.

It is preferred that the limiter 1415 be a memoryless limiter so that clipping in a prior cycle of the signal does not effect future performance of the limiter 1415. It is preferred that the limiter 1415 have a clippling level comparable to or below the clipping level of ADC. As used herein, "comparable to" refers to zero to minus 3 dB. preferably minus 1 dB. In an alternative embodiment, the amplifier 1410 can be a limiting amplifier, which combines the functions of the amplifier 1410 and the limiter 1415 into a single element. It is also preferred that the limiter comprise an amplifier. the amplifier having a power supply, wherein the limiter's clipping level is responsive to the level of the power supply. It is preferred that the power supply reduce the amplitude so that the amplifier does not output an amplitude that is great enough to cause clipping in the ADC following the filter. Other limiters (devices for performing limiting) may be used, such as a signal clipper, a logarithmic compressor or any other device which would limit the signal to prevent clipping by the analog to digital converter. Additional filtering after the ADC can occur.

On Sep. 14, 1999, U.S. patent application Ser. Nos. 09/396,486; 09/396,912; 09/396,203; 09/396,833; 09/396,911; 09/396,493; 09/396,487; 09/396,832; 09/396,488; 09/396,353; 09/396,834; 09/396,092; and 29/110,834 were filed. Each of these patent applications is hereby incorporated by reference herein.

The attached appendix provides both the circuitry and object code for operation on the circuitry. Some of the object code is intended for operation on an attached processor or computer. The object code has therefore been printed in the appendix as a self-extracting executable file. Upon extraction, the object code may be installed on the system by executing the extracted file LYNXINSTALL.EXE. This execution will complete the installation procedure creating the necessary file structure, registry entries, and driver installation.

While the invention has been described above by reference to various embodiments, it will be understood that many changes and modifications can be made without departing from the scope of the invention.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound imaging system comprising:
    a subsystem comprising a reprogrammable logic device;
    a storage device storing configuration data; and
    a central processing unit operative to reprogram the reprogrammable logic device with the configuration data;
    wherein the subsystem comprising the reprogrammable logic device is within an ultrasound data processing path for processing ultrasound data.

2. The invention of claim 1, wherein the central processing unit is operative to reprogram the reprogrammable logic device in response to a change in a transducer probe.

3. The invention of claim 1, wherein the central processing unit is operative to reprogram the reprogrammable logic device in response to an operator control change.

4. The invention of claim 1, wherein the central processing unit is operative to reprogram the reprogrammable logic device dynamically as part of system operation.

5. The invention of claim 1, wherein the central processing unit is operative to reprogram the reprogrammable logic device between scan lines.

6. The invention of claim 1, wherein the central processing unit is operative to reprogram the reprogrammable logic device between image frames.

7. The invention of claim 1, wherein the reprogrammable logic device comprises a transmit beamformer controller field-programmable gate array.

8. The invention of claim 1, wherein the reprogrammable logic device comprises a beamformer field-programmable gate array.

9. The invention of claim 1, wherein the reprogrammable logic device comprises an RF processor field-programmable gate array.

10. The invention of claim 1, wherein the reprogrammable logic device comprises a Doppler processor field-programmable gate array.

11. The invention of claim 1, wherein the reprogrammable logic device comprises a scan converter field-programmable gate array.

12. The invention of claim 1, wherein the configuration data loader is operative to reprogram the reprogrammable logic device in response to a mode change.

13. The invention of claim 1, wherein the central processing unit is operative to reprogram the reprogrammable logic device in response to an operator control change.

14. The invention of claim 1, wherein the central processing unit is operative to reprogram the reprogrammable logic device for test purposes.

15. A medical diagnostic ultrasound imaging system comprising:
    a storage device storing configuration data;
    a memory unit;
    a central processing unit coupled with the storage device and the memory unit;
    a host interface coupled with the memory unit; and
    a subsystem comprising a reprogrammable logic device coupled with the host interface;
    wherein the central processing unit is operative to send configuration information from the storage device to the memory unit and wherein the host interface is operative to reprogram the reprogrammable logic device with the configuration information in the memory unit;
    wherein the subsystem comprising the reprogrammable logic device is within an ultrasound data processing path for processing ultrasound data.

16. The invention of claim 15, wherein the host interface comprises a DMA controller and a field-programmable gate array.

17. The invention of claim 15, wherein the host interface is operative to reprogram the reprogrammable logic device in response to a change in a transducer probe.

18. The invention of claim 15, wherein the host interface is operative to reprogram the reprogrammable logic device in response to a mode change.

19. The invention of claim 15, wherein the host interface is operative to reprogram the reprogrammable logic device between scan lines.

20. The invention of claim 15, wherein the host interface is operative to reprogram the reprogrammable logic device between image frames.

21. The invention of claim 15, wherein the host interface is operative to reprogram the reprogrammable logic device for test purposes.

22. The invention of claim 15, wherein the reprogrammable logic device comprises a transmit beamformer controller field-programmable gate array.

23. The invention of claim 15, wherein the reprogrammable logic device comprises a beamformer field-programmable gate array.

24. The invention of claim 15, wherein the reprogrammable logic device comprises an RF processor field-programmable gate array.

25. The invention of claim 15, wherein the reprogrammable logic device comprises a Doppler processor field-programmable gate array.

26. The invention of claim 15, wherein the reprogrammable logic device comprises a scan converter field-programmable gate array.

27. A medical diagnostic ultrasound system, comprising at least one reprogrammable logic device having a plurality of gates that are reconfigured for different ultrasound processing modalities during the course of an ultrasound exam; wherein the at least one reprogrammable logic device is part of a subsystem within an ultrasound data processing path for processing ultrasound data.

28. The ultrasound system of claim 27 wherein the at least one reprogrammable logic device includes circuitry for beam formation.

29. The ultrasound system of claim 27 wherein the at least one reprogrammable logic device includes circuitry for scan conversion.

30. The invention of claims 27, 28, or 29 wherein the ultrasound system weighs less than 40 pounds.

31. The invention of claim 30, wherein the ultrasound system comprises at least 32 electrical channels.

32. The invention of claims 27, 28, or 29, wherein the ultrasound system comprises at least 32 electrical channels.

33. A medical diagnostic ultrasound system, comprising at least one reprogrammable logic device having a plurality of gates that are reconfigured for processing signals resulting from ultrasound echoes during the course of interrogating a field of view with said system.

34. The ultrasound system of claim 33, wherein the at least one reprogrammable logic device is capable of being reconfigured on a scan line by scan line basis.

35. The invention of claims 33 or 34 wherein the ultrasound system comprises at least 32 electrical channels.

36. The invention of claim 35, wherein the ultrasound system weighs less than 40 pounds.

37. The invention of claims 35, wherein the at least one reprogrammable logic device includes circuitry for scan conversion.

38. The invention of claim 33 or 34, wherein the ultrasound system weighs less than 40 pounds.

39. The invention of claim 38, wherein the at least one reprogrammable logic device includes circuitry for scan conversion.

40. The invention of claims 33 or 34, wherein the at least one reprogrammable logic device includes circuitry for scan conversion.

41. A medical diagnostic ultrasound imaging system comprising:

a subsystem comprising a reprogrammable logic device;

a storage device storing configuration data; and a configuration data loader operative to reprogram the reprogrammable logic device with the configuration data;

wherein the subsystem comprising the reprogrammable logic device is within an ultrasound data processing path for processing ultrasound data.

42. The invention of claim 41, wherein the configuration data loader is operative to reprogram the reprogrammable logic device in response to a change in a transducer probe.

43. The invention of claim 41, wherein the configuration data loader is operative to reprogram the reprogrammable logic device between scan lines.

44. The invention of claim 41, wherein the configuration data loader is operative to reprogram the reprogrammable logic device between image frames.

45. The invention of claim 41, wherein the configuration data loader is operative to reprogram the reprogrammable logic device for test purposes.

46. The invention of claim 41, wherein the reprogrammable logic device comprises a transmit beamformer controller field-programmable gate array.

47. The invention of claim 41, wherein the reprogrammable logic device comprises a beamformer field-programmable gate array.

48. The invention of claim 41, wherein the reprogrammable logic device comprises an RF processor field-programmable gate array.

49. The invention of claim 41, wherein the reprogrammable logic device comprises a Doppler processor field-programmable gate array.

50. The invention of claim 41, wherein the reprogrammable logic device comprises a scan converter field-programmable gate array.

51. The invention of claim 41, wherein the configuration data loader comprises a device selected from the group consisting of a central processing unit, a state machine, a DSP, a microprocessor, an ASIC.

52. The invention of claim 1, 15, 27, 33, or 41, wherein the diagnostic ultrasound system is portable.

53. The invention of claim 1, 15, 27, 33, or 41, wherein the reprogrammable logic device comprises a field programmable gate array.

54. The invention of claim 1, 15, 27, 33, or 41, wherein the diagnostic ultrasound system comprises at least 32 electrical channels.

* * * * *